(12) United States Patent
Hartz et al.

(10) Patent No.: US 10,774,086 B2
(45) Date of Patent: Sep. 15, 2020

(54) GSK-3 INHIBITORS

(71) Applicant: BRISTOL-MYERS SQUIBB COMPANY, Princeton, NJ (US)

(72) Inventors: Richard A. Hartz, Ewing, NJ (US); Vijay T. Ahuja, Princeton, NJ (US); Prasanna Sivaprakasam, Lawrenceville, NJ (US); Gene M. Dubowchik, Middlefield, CT (US); John E. Macor, Washington Crossing, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/463,451

(22) PCT Filed: Nov. 27, 2017

(86) PCT No.: PCT/US2017/063230
§ 371 (c)(1),
(2) Date: May 23, 2019

(87) PCT Pub. No.: WO2018/098411
PCT Pub. Date: May 31, 2018

(65) Prior Publication Data
US 2019/0276463 A1 Sep. 12, 2019

Related U.S. Application Data

(60) Provisional application No. 62/426,630, filed on Nov. 28, 2016.

(51) Int. Cl.
*A61K 31/5025* (2006.01)
*C07D 487/04* (2006.01)

(52) U.S. Cl.
CPC ........ *C07D 487/04* (2013.01); *A61K 31/5025* (2013.01)

(58) Field of Classification Search
CPC ................. A61K 31/5025; C07D 487/04
USPC ........................................ 514/248; 544/236
See application file for complete search history.

(56) References Cited

FOREIGN PATENT DOCUMENTS

WO   WO2012136776 A1   10/2012
WO   WO2013059594 A1   4/2013

OTHER PUBLICATIONS

Li, X., et al. Mol Neurobiol (2013) 48: 490.

*Primary Examiner* — Jeffrey H Murray
(74) *Attorney, Agent, or Firm* — Elliott Korsen

(57) ABSTRACT

The disclosure generally relates to compounds of formula (I), including their salts, as well as compositions and methods of using the compounds to treat disorders associated with GSK-3.

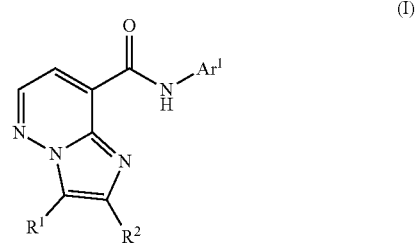

7 Claims, No Drawings

GSK-3 INHIBITORS

CROSS REFERENCE TO RELATED APPLICATION

This application claims the priority of U.S. provisional Ser. No. 62/426,630 filed Nov. 28, 2016 which is herein incorporated by reference.

BACKGROUND OF THE INVENTION

The disclosure generally relates to compounds of formula I, including their salts, as well as compositions and methods of using the compounds. The compounds inhibit GSK-3 and may be useful for the treatment of various disorders of the central nervous system.

GSK-3 is a proline directed serine/threonine kinase that carries out the phosphorylation of multiple protein substrates. Many of these proteins are involved in the regulation of numerous diverse cellular functions, including metabolism, differentiation, proliferation and apoptosis. GSK-3 is constitutively active, with its base level of activity being positively modulated by phosphorylation on Tyr216/219, depending on isoform. GSK-3 has a unique substrate selectivity profile that is distinguished by the strong preference for the presence of a phosphorylated residue optimally located four amino acids C-terminal to the site of GSK-3 phosphorylation. Most commonly, GSK-3 activity is associated with inducing a loss of substrate function, such that GSK-3 inhibition will frequently result in increased downstream substrate activity.

GSK-3 exists in two isoforms, GSK-3α (51 kDa) and GSK-3β (47 kDa), that share 84% overall identity and greater than 98% identity within their respective catalytic domains. Both primary isoforms are ubiquitously expressed, with high levels observed in the brain, particularly in the cortex and hippocampus. In most brain areas, GSK-3β is the predominant isoform. However, some studies suggest that GKS-3α and GSK-3β share very similar, if not entirely redundant functions in a number of cellular processes. The activity of GSK-3β is significantly reduced by phosphorylation at Ser9 in the N-terminal domain, most notably by protein kinase B (PKB or AKT). This inhibitory pathway has been proposed to result in neuroprotection, neurogenesis, and favorable outcomes following pharmacological treatment in various mood disorders.

Alzheimer's disease (AD) pathology is prominently associated with the formation of beta-amyloid (Aβ) plaques, soluble forms of Aβ such as Aβ1-42 that are associated with increased neuronal toxicity, and neurofibrillary tangles (NFTs). There is evidence to suggest that certain pathological mechanisms in AD, such as Aβ1-42, cause increases in GSK-3 activity in the brain. A principal consequence of this dysregulation is the hyperphosphorylation of the microtubule associated protein tau. This function of GSK-3 has been demonstrated both in cell culture, and in in vivo studies looking at tau and NFT formation. Hyper-phosphorylated tau disengages from microtubules resulting in structural destabilization of microtubules with concomitant negative effects on intracellular structures and transport mechanisms. In addition, the uncomplexed hyperphosphorylated tau assembles into paired helical filaments (PHFs) that aggregate to produce the stereotypic intracellular NFTs associated with AD. Other potential pathological consequences of over-activation of GSK-3 include neuroinflammation and neuronal apoptosis. In addition, GSK-3 has been demonstrated to be involved in mechanisms underlying memory and learning, and dysregulation of GSK-3 function may explain some of the early cognitive deficits observed in AD.

GSK-3 is also known to play a key role in glucose metabolism, and was first identified as the enzyme responsible for effecting the inhibitory phosphorylation of glycogen synthase, the result of which is to reduce the rate of conversion of glucose to glycogen, giving rise to elevated blood glucose levels. This function of GSK-3 is controlled by insulin. Binding of insulin to its receptor leads indirectly to the activation of AKT and subsequent inhibitory Ser9 phosphorylation of GSK-3.

These results and observations suggest that modulation of GSK-3 activity may be useful in the treatment of both the neuropathologic and symptomatic aspects of Alzheimer's disease, as well as other neurodegenerative diseases. These include, but are not limited to, tauopathies (for example, frontotemporal dementia, progressive supranuclear palsy, argyophilic grain disease, corticobasal degeneration, Pick's disease), Parkinson's disease, amyotrophic lateral schlerosis, stroke, Huntington's disease, peripheral neuropathies, traumatic brain injury, spinal cord trauma, and vascular dementias.

Compounds that inhibit GSK-3 may also have utility in the treatment of diabetes, inflammatory diseases such as rheumatoid arthritis and osteoarthritis, treatment-resistant depression, schizophrenia, bipolar disorder, manic depression, osteoporosis, cardioprotection, and various cancers such as gliomas, non-small cell lung cancer, pancreatic cancer, breast cancer, T- or B-cell leukemia, and multiple myeloma. Inhibition of GSK-3 has also been shown to downregulate PD-1 in T-reg cells, enhancing viral clearance in vivo (Immunity, Volume 44, Issue 2, 16 Feb. 2016).

Recent reviews on the functions of GSK-3, potential therapeutic applications, and other compounds that inhibit the enzyme are listed below: Kaidanovich-Beilin O and Woodgett J R (2011) GSK-3: functional insights from cell biology and animal models. *Front. Mol. Neurosci.* 4:40. doi: 10.3389/fnmol.2011.00040; "Glycogen Synthase Kinase 3 (GSK-3) and Its Inhibitors", Martinez, Ana/Castro, Ana/Medina, Miguel (eds.), John Wiley and Sons (2006); and Gentles, R G, Hu, S. and Dubowchik, G M (2009) Recent Advances in the Discovery of GSK-3 Inhibitors and a Perspective on their Utility for the Treatment of Alzheimer's Disease. *Annual Reports in Medicinal Chemistry* 44, 3-26.

The invention provides technical advantages, for example, the compounds are novel inhibitors of GSK-3 and may be useful for the treatment of various disorders of the central nervous system. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, pharmaceutical compositions, and their use in treating disorders associated with GSK-3.

One aspect of the invention is a compound of formula I

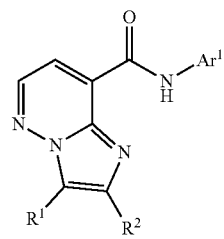

where:
R¹ is hydrogen or N(R³)(R⁴);
R² is hydrogen, alkyl, cycloalkyl, or cycloalkenyl;
or R² is pyridinyl or phenyl and is substituted with 0-3 substituents selected from cyano, halo, alkyl, haloalkyl, alkoxy, and haloalkoxy;
R³ is hydrogen, alkyl, (cycloalkyl)alkyl, cycloalkyl, alkylcarbonyl, or cycloalkylcarbonyl;
R⁴ is hydrogen;
Ar¹ is 3-pyridinyl, 3-pyridazinyl, 4-pyridazinyl, 5-pyrimidinyl, or 2-pyrazinyl, and is substituted with 0-3 substituents selected from halo, alkyl, haloalkyl, alkoxy, haloalkoxy, alkylsulfonyl, N(R³)(R⁴), or Ar²; and
Ar² is phenyl substituted with 0-3 substituents selected from cyano, halo, alkyl, haloalkyl, alkoxy, haloalkoxy;
or a pharmaceutically acceptable salt thereof.

Another aspect of the invention is a compound of formula I where R¹ is N(R³)(R⁴) and R² is hydrogen.

Another aspect of the invention is a compound of formula I where R¹ is hydrogen and R² is not hydrogen.

Another aspect of the invention is a compound of formula I where Ar¹ is 3-pyridinyl substituted with 0-3 substituents selected from the group consisting of cyano, halo, alkyl, haloalkyl, (R²)alkyl, alkoxy, haloalkoxy, and R².

Another aspect of the invention is a compound of formula I where Ar¹ is 5-pyrimidinyl substituted with 0-3 substituents selected from the group consisting of cyano, halo, alkyl, haloalkyl, (R²)alkyl, alkoxy, haloalkoxy, and R².

Another aspect of the invention is a compound of formula I where Ar² is phenyl substituted with 0-3 substituents selected from the group consisting of cyano, halo, alkyl, haloalkyl, alkoxy, haloalkoxy, alkylsulfinyl, and alkylsulfonyl.

For a compound of formula I, the scope of any instance of a variable substituent, including R¹, R², R³, R⁴, Ar¹, and Ar², can be used independently with the scope of any other instance of a variable substituent. As such, the invention includes combinations of the different aspects.

Unless specified otherwise, these terms have the following meanings. "Halo" includes fluoro, chloro, bromo, and iodo. "Alkyl" means a straight or branched alkyl group composed of 1 to 6 carbons. "Alkenyl" means a straight or branched alkyl group composed of 2 to 6 carbons with at least one double bond. "Alkynyl" means a straight or branched alkyl group composed of 2 to 6 carbons with at least one triple bond. "Cycloalkyl" means a monocyclic ring system composed of 3 to 7 carbons. "Haloalkyl" and "haloalkoxy" include all halogenated isomers from monohalo to perhalo. Terms with a hydrocarbon moiety (e.g. alkoxy) include straight and branched isomers for the hydrocarbon portion. "Aryl" means a monocyclic or bicyclic aromatic hydrocarbon groups having 6 to 12 carbon atoms, or a bicyclic fused ring system wherein one or both of the rings is a phenyl group. Bicyclic fused ring systems consist of a phenyl group fused to a four- to six-membered aromatic or non-aromatic carbocyclic ring. Representative examples of aryl groups include, but are not limited to, indanyl, indenyl, naphthyl, phenyl, and tetrahydronaphthyl. "Heteroaryl" means a 5 to 7 membered monocyclic or 8 to 11 membered bicyclic aromatic ring system with 1-5 heteroatoms independently selected from nitrogen, oxygen, and sulfur. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some Formula I compounds contain at least one asymmetric carbon atom. The invention includes all stereoisomeric forms of the compounds, both mixtures and separated isomers. Mixtures of stereoisomers can be separated into individual isomers by methods known in the art.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include ¹³C and ¹⁴C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

The kinase assay was performed in V-bottom 384-well plates. The final assay volume was 30 µl prepared from 15 µl additions of enzyme, substrates (fluoresceinated peptide FL-KRREILSRRP[ps]ERYR-NH2 and ATP) and test compounds in assay buffer (100 mM HEPES pH 7.4, 10 mM MgCl₂, 25 mM Beta-Glycerolphosphate, 0.015% Brij35 and 0.25 mM DTT). The reaction was incubated at room temperature for 20 hours and terminated by adding 45 µl of 35 mM EDTA to each sample. The reaction mixture was analyzed on the Caliper LabChip3000 (Caliper, Hopkinton, Mass.) by electrophoretic separation of the unphosphorylated substrate and phosphorylated product. Inhibition data were calculated by comparison of the no enzyme control reactions for 100% inhibition and vehicle-only reactions for 0% inhibition. The final concentration of reagents in the assay were 250 pM GSK3u or GSK3O, 20 uM ATP, 1.5 uM FL-KRREILSRRP[ps]ERYR-NH2, and 1.6% DMSO. Dose response curves were generated to determine the concentration required to inhibit 50% of the kinase activity ($IC_{50}$). Compounds were dissolved at 10 mM in dimethylsulfoxide (DMSO) and evaluated at eleven concentrations. $IC_{50}$ values were derived by non-linear regression analysis.

| Example | GSK3β/GSK3α (nM) | pTau (nM) |
|---|---|---|
| 1 | 17.1/5.3 | 660 |
| 2 | 3.5/0.8 | 250 |
| 3 | 0.7/0.4 | 83 |
| 4 | 0.3/0.1 | 22 |
| 5 | 1.5/0.4 | 120 |
| 6 | 3.6/1.1 | 900 |
| 7 | 1.6/0.6 | — |
| 8 | 1.1/0.3 | 160 |
| 9 | 1.1/0.2 | — |
| 10 | 0.2/0.1 | — |
| 11 | 0.3/0.2 | 24 |
| 12 | 0.4/0.2 | 30 |
| 13 | 0.4/0.2 | 36 |
| 14 | 0.75/0.4 | 58 |
| 15 | 0.2/0.09 | 9.2 |
| 16 | 0.8/0.3 | 86 |
| 17 | 3.4/1.0 | 180 |
| 18 | 0.3/0.3 | 5.7 |
| 19 | 37/7/5 | 3,200 |
| 20 | 2.3/0.6 | 160 |
| 21 | 0.6/0.2 | 140 |
| 22 | 14/2.9 | 2,000 |
| 23 | 0.8/0.6 | 110 |
| 24 | 0.6/0.4 | 79 |
| 25 | 0.8/0.2 | 49 |
| 26 | 1.4/0.6 | 120 |
| 27 | 19.8/11.4 | 760 |
| 28 | 4.6/2.0 | 140 |
| 29 | 3.8/3.2 | 250 |
| 30 | 1.9/0.4 | 380 |
| 31 | 0.4/0.2 | 120 |
| 32 | 2.6/0.8 | 60 |
| 33 | 6.1/1.2 | 820 |
| 34 | 0.4/0.1 | 28 |
| 35 | 1.6/1.0 | 160 |
| 36 | 1.3/0.4 | — |
| 37 | 5.3/1.0 | 620 |
| 38 | 3.6/1.0 | 330 |
| 39 | 220/900 | >10,000 |
| 40 | 63/30 | 3,900 |
| 41 | 6.6/3.4 | 290 |
| 42 | 3.4/3.2 | 320 |
| 43 | 1.1/2.0 | 41 |
| 44 | 9.0/1.4 | 65 |
| 45 | 5.2/1.6 | 140 |
| 46 | 6.0/51 | 5,100 |
| 47 | 140/110 | 6,800 |

Pharmaceutical Compositions and Methods of Treatment

Compounds of formula I can be useful in treating neurological or psychiatric disorders. Therefore, another aspect of the invention is a composition comprising a compound of formula I or a pharmaceutically acceptable salt thereof, and a pharmaceutically acceptable carrier.

Another aspect of the invention is a method for the treatment for modulation of GSK-3 activity may be useful in the treatment of both the neuropathologic and symptomatic aspects of Alzheimer's disease, as well as other neurodegenerative diseases. These include, but are not limited to, tauopathies (for example, frontotemporal dementia, progressive supranuclear palsy, argyophilic grain disease, corticobasal degeneration, Pick's disease), Parkinson's disease, amyotrophic lateral sclerosis, stroke, Huntington's disease, peripheral neuropathies, traumatic brain injury, spinal cord trauma, and vascular dementias, which comprises administering to a patient a therapeutically affective amount of a compound of formula I.

Another aspect of the invention is a method for the treatment for diabetes, inflammatory diseases such as rheumatoid arthritis and osteoarthritis, treatment-resistant depression, schizophrenia, bipolar disorder, manic depression, osteoporosis, cardioprotection, and various cancers such as gliomas, non-small cell lung cancer, pancreatic cancer, breast cancer, T- or B-cell leukemia, and multiple myeloma, which comprises administering to a patient a therapeutically affective amount of a compound of formula I.

Another aspect of the invention is a method for the treatment of Alzheimer's disease which comprises administering to a patient a therapeutically affective amount of a compound of formula I.

Another aspect of the invention is the use of a compound of formula I in the manufacture of a medicament for the treatment of Alzheimer's disease.

"Patient" means a person suitable for therapy as understood by practitioners in the field of affective disorders, neurodegenerative disorders, psychiatric disorders, cancer, metabolic disorders, or inflammatory disorders.

"Treatment," "therapy," and related terms are used as understood by practitioners in the field of neurological and psychiatric disorders.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

Synthetic Methods

Compounds of Formula I may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention. The schemes encompass reasonable variations known in the art.

The abbreviations used in the present application, including particularly in the illustrative schemes and examples which follow, are well-known to those skilled in the art. Some of the abbreviations used are as follows: BOC or Boc for tert-butoxycarbonyl; RT or rt or r.t. for room temperature or retention time (context will dictate); $t_R$ for retention time; HATU for O-(7-azabenzotriazol-1-yl)-N,N,N',N'-tetramethyluronium hexafluorophosphate; BOP for benzotriazol-1-yloxytris(dimethylamino)phosphonium hexafluorophosphate; EDC or EDCI for 1-(3-dimethylaminopropyl)-3-ethylcarbodiimide hydrochloride; TBTU for O-benzotriazol-1-yl-N,N,N',N'-tetramethyluronium tetrafluoroborate; SPhos for 2-dicyclohexylphosphino-2',6'-dimethoxybiphenyl; XPhos for 2-dicyclohexylphosphino-2',4',6'-triisopropylbiphenyl; i-Pr or iPr for isopropyl; THF for tetrahydrofuran; EtOH for ethanol; Ac for acetyl; DMAP for N,N-dimethylaminopyridine; TEA or $Et_3N$ for triethylamine; DIEA or i-$Pr_2$NEt for N,N-diisopropylethylamine; Me for methyl; TFA for trifluoroacetic acid; Ph for phenyl; DMF for N,N-dimethylformamide; DMSO for dimethylsulfoxide; NMP for N-methylpyrrolidine; MeCN for acetonitrile; HOBt for 1-hydroxybenzotriazole; dppf for 1,1'-bis(diphenylphosphanyl) ferrocene; Et for ethyl; h or hr or hrs for hours; min or mins for minutes; EtOAc for ethyl acetate; DCM for dichloromethane; MeOH for methanol; AcOH for acetic acid; and MeOD for $CD_3OD$.

Preparation of Compounds of Formula I General Chemistry Scheme:

Compounds of Formula I can be prepared as described in Scheme 1. Compound 2 is prepared by formation of the ethyl ester of 1. The reaction can be carried out using standard coupling reagents such as HATU, BOP, EDC, T3P or TBTU in the presence of DMAP and a solvent such as dichloromethane, dichloroethane, DMF, or THF at temperatures ranging from 20° C. to 80° C. to form compound 2. Treatment of 2 with 4-methoxybenzylamine in the presence of a base such as N,N-diisopropylethylamine in a solvent such as dioxane or THF affords compound 3. Removal of the protecting group in 3 can be accomplished by heating 3 in the presence of trifluoroacetic acid to furnish 4. Preparation of 5 can be conducted by heating 4 in the presence of substituted 2-bromoketones in a solvent such as dioxane, THF, or DMF at temperatures ranging from 25° C. to 120° C. Removal of the chloro substituent in 5 can then be carried out by a hydrogenation reaction in the presence of 10% palladium on carbon to afford 6. Hydrolysis of the ester in 6 is completed using lithium hydroxide, sodium hydroxide or potassium hydroxide in a mixture of THF or dioxane and water to form 7. Compounds of formula I are prepared by a coupling reaction between 7 and various amines. The coupling reaction can be carried out using standard peptide coupling reagents such as HATU, BOP, EDC, T3P or TBTU in the presence of a base such as N,N-diisopropylethylamine and a solvent such as dichloromethane, dichloroethane, DMF, or THF at temperatures ranging from 20° C. to 80° C. to form compounds of formula I.

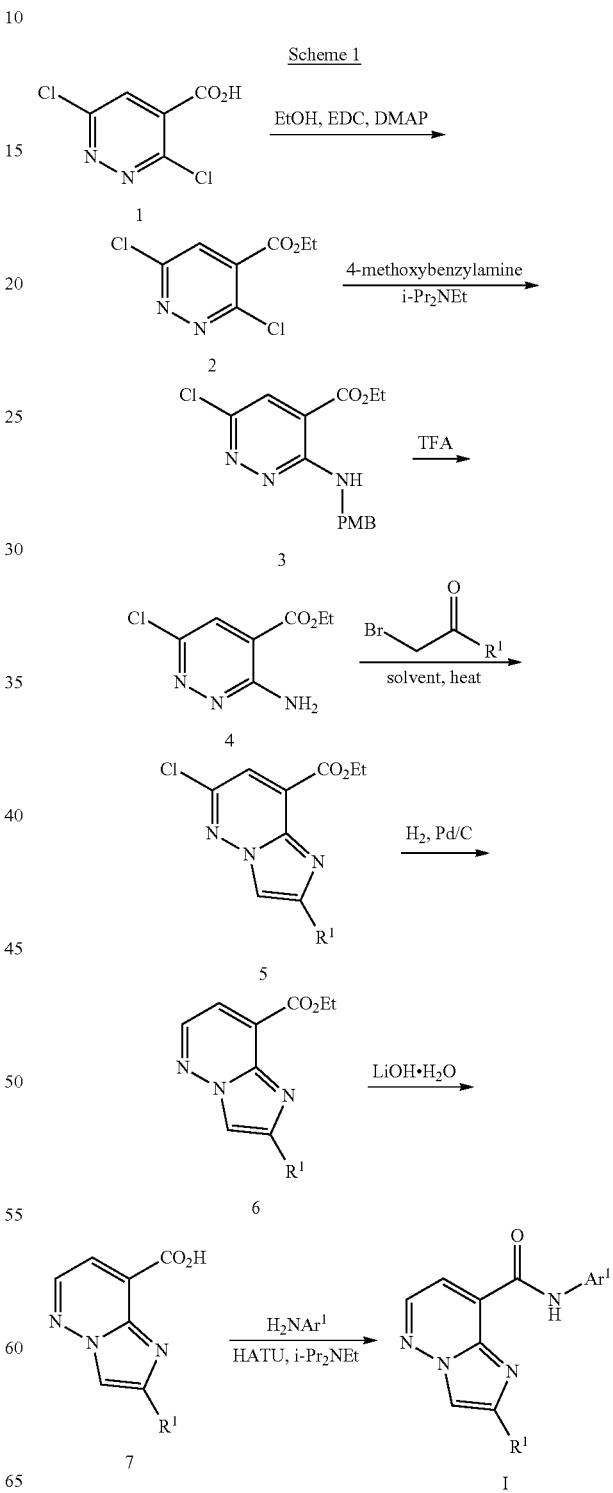

Alternate Route for the Preparation of Compounds of Formula I General Chemistry Scheme:

Alternatively, compounds of Formula I can be prepared by the route shown in Scheme 2. Compound 3 from Scheme 1 is treated with bis(pinacolato)diboron, $PdCl_2(dppf)$, and potassium acetate in a solvent such as dioxane to furnish 8. Removal of the protecting group in 8 can be accomplished by heating 8 in the presence of trifluoroacetic acid to furnish 9. Preparation of 6 can be conducted by heating 9 in the presence of substituted 2-bromoketones in a solvent such as dioxane, THF, or DMF at temperatures ranging from 25° C. to 120° C. Hydrolysis of the ester in 6 is completed using lithium hydroxide, sodium hydroxide or potassium hydroxide in a mixture of THF or dioxane and water to form 7. Compounds of formula I are prepared by a coupling reaction between 7 and various amines. The coupling reaction can be carried out using standard peptide coupling reagents such as HATU, BOP, EDC, T3P or TBTU in the presence of a base such as N,N-diisopropylethylamine and a solvent such as dichloromethane, dichloroethane, DMF, or THF at temperatures ranging from 20° C. to 80° C. to form compounds of formula I.

Preparation of Compounds of Formula II General Chemistry Scheme:

Compounds of Formula II can be prepared as described in Scheme 3. Preparation of 10 can be carried out by heating 4 in the presence of chloroacetaldehyde in a solvent such as isopropanol, dioxane, THF, or DMF at temperatures ranging from 25° C. to 120° C. Nitration of 10 in the presence of fuming nitric acid/sulfuric acid then furnishes compound 11. Removal of the chloro substituent in 11 is then carried out by a hydrogenation reaction in the presence of 10% palladium on carbon to afford 12. Compound 13 was then prepared by a reductive amination reaction with 12 and an aldehyde in the presence of a reducing agent such as sodium cyanoborohydride or sodium triacetoxyborohydride in acetic acid and methanol. Hydrolysis of the ester in 13 is completed using lithium hydroxide, sodium hydroxide or potassium hydroxide in a mixture of THF or dioxane and water to form 14. Compounds of formula II are prepared by a coupling reaction between 14 and various amines. The coupling reaction can be carried out using standard peptide coupling reagents such as HATU, BOP, EDC, T3P or TBTU in the presence of a base such as N,N-diisopropylethylamine and a solvent such as dichloromethane, dichloroethane, DMF, or THF at temperatures ranging from 20° C. to 80° C. to form compounds of formula II.

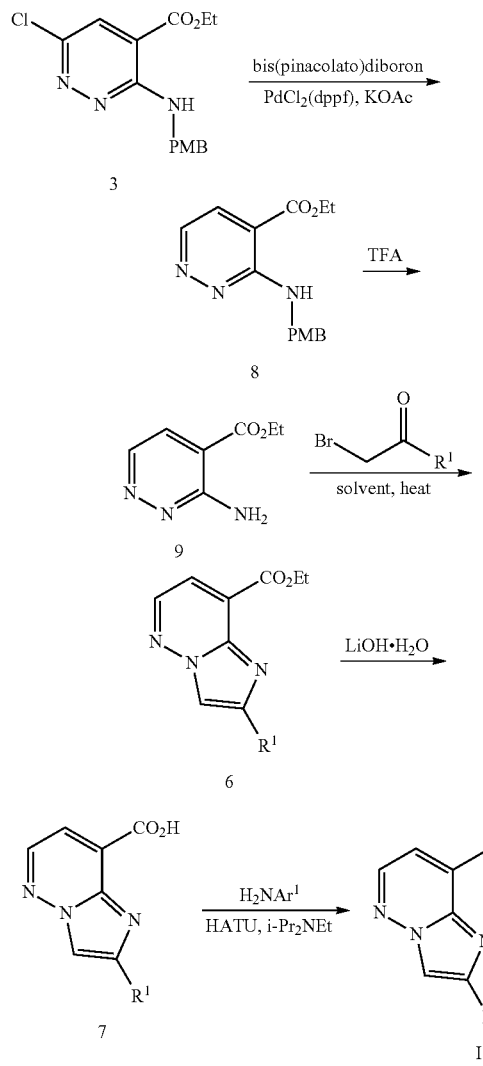

Scheme 2

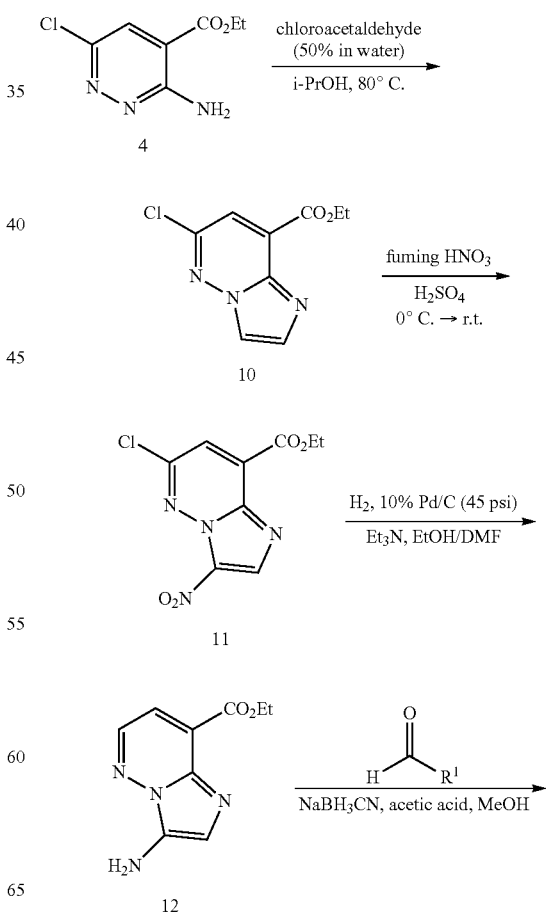

Scheme 3

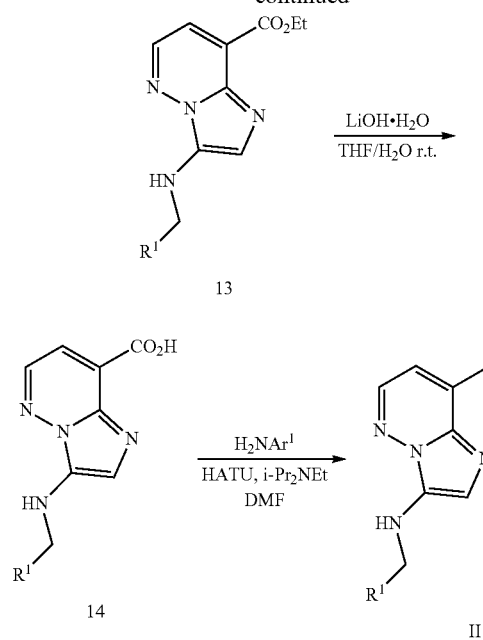

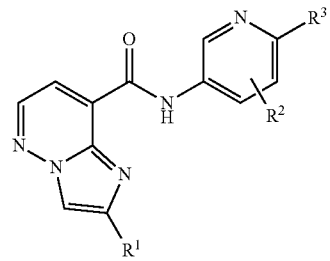

Various analogs synthesized using Schemes 1-2 are listed in Table 1.

TABLE 1

| Example | R¹ | R² | R³ |
|---|---|---|---|
| 1 | Ph | H | H |
| 2 | Ph | 4-Me | H |
| 3 | Ph | 4-OCH(CH₃)₂ | H |
| 4 | Ph | 4-OCH₂CF₃ | H |
| 5 | Ph | 4-SO₂Me | H |
| 6 | Ph | 4-Ph | H |
| 7 | Ph | 4-(4-F—Ph) | H |
| 8 | Ph | 4-(4-CN—Ph) | H |
| 9 | Ph | 4-N-piperidine | H |
| 10 | Ph | 4-(4-CN—N-piperidine) | H |
| 11 | Ph | 4-(4-F—N-piperidine) | H |
| 12 | Ph | 4-(4,4-difluoro-N-piperidine) | H |
| 13 | Ph | 4-(4-morpholine) | H |
| 14 | Ph | 4-(2-methyl-4-morpholine) | H |
| 15 | Ph | 4-(2-methyl-4-morpholine) | H |
| 16 | Ph | 4-(2-methyl-4-morpholine) | H |
| 17 | Ph | 4-((R)-3-methyl-4-morpholine) | H |
| 18 | Ph | 4-((S)-3-methyl-4-morpholine) | H |
| 19 | Ph | 5-OMe | H |
| 20 | Ph | 4-(4,4-difluoro-N-piperidine) | F |
| 21 | Ph | 4-(2-methyl-4-morpholine) | F |

TABLE 1-continued

| Example | R¹ | R² | R³ |
|---|---|---|---|
| 22 | Ph | 4-(4,4-difluoro-N-piperidine) | Cl |
| 23 | 2-OMe—Ph | 4-(4,4-difluoro-N-piperidine) | H |
| 24 | 2-OMe—Ph | 4-(2-methyl-4-morpholine) | H |
| 25 | 4-CF₃—Ph | 4-(4-morpholine) | H |
| 26 | 4-CF₃—Ph | 4-(2-methyl-4-morpholine) | H |
| 27 | H | 4-N-piperidine | H |
| 28 | H | 4-(4,4-difluoro-N-piperidine) | H |
| 29 | H | 4-(2-methyl-4-morpholine) | H |
| 30 | cPr | 4-(4-F—Ph) | H |
| 31 | cPr | 4-(4,4-difluoro-N-piperidine) | H |
| 32 | cPr | 4-(2-methyl-4-morpholine) | H |
| 33 | 1-cyclohexene | 4-(4-F—Ph) | H |
| 34 | 1-cyclohexene | 4-(4,4-difluoro-N-piperidine) | H |
| 35 | 1-cyclohexene | 4-(2-methyl-4-morpholine) | H |
| 36 | Pyridin-3-yl | 4-(4-morpholine) | H |

Various analogs synthesized using Schemes 1-2 are listed in Table 2.

TABLE 2

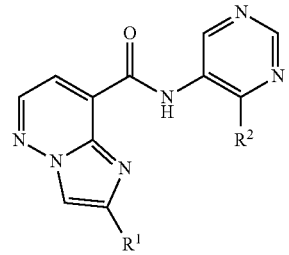

| Example | R¹ | R² |
|---|---|---|
| 37 | Ph | OEt |
| 38 | Ph | OCH₂CF₃ |

Various analogs synthesized using Scheme 3 are listed in Table 3.

TABLE 3

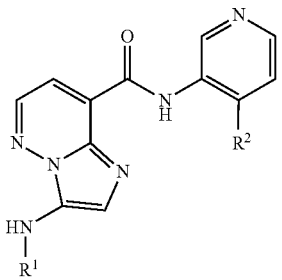

| Example | R¹ | R² |
|---|---|---|
| 39 | CH₂—cPr | H |
| 40 | CH₂—cPr | Me |
| 41 | CH₂—cPr | OCH(CH₃)₂ |
| 42 | CH₂—cPr | Ph |
| 43 | CH₂—cPr | 4,4-difluoro-N-piperidine |
| 44 | CH₂—cPr | 4-morpholine |
| 45 | CH₂—cPr | 2-methyl-4-morpholine |
| 46 | C(O)cPr | OCH(CH₃)₂ |
| 47 | C(O)cBu | OCH(CH₃)₂ |

In the following examples, proton NMR spectra were recorded on either a Bruker 400 or 500 MHz NMR spectrometer. Chemical shifts are reported in δ values relative to tetramethylsilane. Liquid chromatography (LC)/mass spectra were run on a Shimadzu LC coupled to a Waters Micromass ZQ.

Preparative HPLC Method
Method A
Column: Waters Sunfire 30×150 mm, 5 um
Mobile Phase A: 5% acetonitrile/95% water, 0.1% TFA
Mobile Phase B: 95% acetonitrile/5% water 0.1% TFA
Gradient: 10% B to 100% B over 20 minute gradient; hold at 100% B for 5 min
Flow Rate: 40 mL/min
Detector Wavelength: 254 nm Analytical HPLC Methods
Method A
Column: Waters Sunfire C18, 4.6×150 mm, 3.5 m
Mobile Phase A: water with 0.1% TFA
Mobile Phase B: acetonitrile with 0.1% TFA
Gradient: 10% B to 95% B over 15 min gradient; hold at 100% B for 5 min
Flow Rate: 1 mL/min
Detector Wavelength: 254 nm Method B
Column: Waters Xbridge Phenyl, 4.6×150 mm, 3.5 m
Mobile Phase A: water with 0.1% TFA
Mobile Phase B: acetonitrile with 0.1% TFA
Gradient: 10% B to 95% B over 15 min gradient; hold at 100% B for 5 min
Flow Rate: 1 mL/min
Detector Wavelength: 254 nm Method C
Column: Waters XTERRA C18 4.6×30 mm, 3.5 m
Mobile Phase A: 10% methanol/90% water with 0.1% TFA
Mobile Phase B: 90% methanol/10% water with 0.1% TFA
Gradient: 0% B to 100% B over 12 min gradient; hold at 100% B for 10 min
Flow Rate: 1 mL/min
Detector Wavelength: 254 nm Method D
Column: Phenomenex LUNA Phenyl-Hex 4.6×150 mm, 3.5 m
Mobile Phase A: 10% methanol/90% water with 0.1% TFA
Mobile Phase B: 90% methanol/10% water with 0.1% TFA
Gradient: 0% B to 100% B over 12 min gradient; hold at 100% B for 10 min
Flow Rate: 1 mL/min
Detector Wavelength: 254 nm The following abbreviations are used: THF (tetrahydrofuran), MeOH (methanol), DMF (N,N-dimethylformamide), EtOH (ethanol), MeCN (acetonitrile), DCE (dichloroethane), DCM (dichloromethane), TFA (trifluoroacetic acid), HCl (hydrochloric acid), DMAP (dimethylaminopyridine), n-BuLi (n-butyllithium), DIPEA (N,N-diisopropylethylamine), HATU (O-(7-azabenzotriazol-1-yl)-N,N,N',N'-tetramethyluronium hexafluorophosphate), TBTU (N,N,N',N'-tetramethyl-O-(benzotriazol-1-yl)uronium tetrafluoroborate), TLC (thin layer chromatography), NMR (nuclear magnetic resonance), LC/MS or LCMS (liquid chromatography/mass spectrometry), HPLC (high pressure liquid chromatography).

Preparation of 2-phenylimidazo[1,2-b]pyridazine-8-carboxylic acid Via Scheme 1

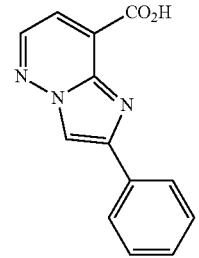

Part A. Ethyl 3,6-dichloropyridazine-4-carboxylate

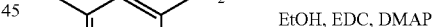

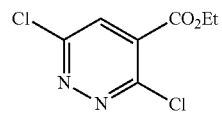

To a mixture of 3,6-dichloropyridazine-4-carboxylic acid (15.0 g, 78 mmol) in THF (150 mL) was added ethanol (18.15 mL, 311 mmol) and DMAP (0.950 g, 7.77 mmol). EDC (16.39 g, 85 mmol) was then added in portions over 1 min. The reaction was mildly exothermic. The reaction was stirred at room temperature for 16 h. The reaction mixture was transferred to a separatory funnel containing saturated aqueous NaHCO₃ solution (150 mL). The aqueous layer was extracted with ether (3×250 mL). The combined organic layers were washed with brine (100 mL), dried over MgSO₄, filtered, and concentrated. The residue was purified by column chromatography on silica gel (20%→40% ethyl acetate in hexanes; 300 g column) to afford ethyl 3,6-dichloropyridazine-4-carboxylate (13.2 g, 59.7 mmol, 77% yield) as a colorless oil: ¹H NMR (400 MHz, CDCl₃) δ 7.88 (s, 1H), 4.50 (q, J=7.0 Hz, 2H), 1.46 (t, J=7.2 Hz, 3H); LCMS (ESI) m/e 221.1 [(M+H)⁺, calcd for C₇H₇C₁₂N₂O₂ 221.0].

Part B. Ethyl 6-chloro-3-((4-methoxybenzyl)amino)pyridazine-4-carboxylate

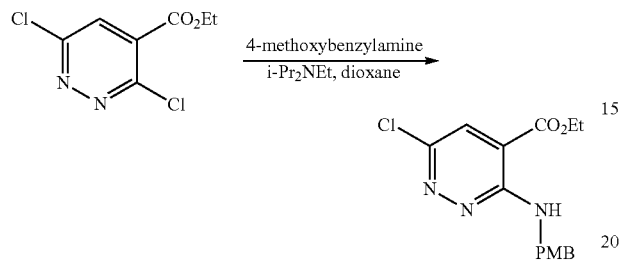

To a solution of ethyl 3,6-dichloropyridazine-4-carboxylate (10.0 g, 45.2 mmol) and (4-methoxyphenyl)methanamine (7.09 mL, 54.3 mmol) in dioxane (200 mL) was added N,N-diisopropylethylamine (23.70 mL, 136 mmol). The reaction mixture was heated at 70° C. for 1 h. The mixture was cooled to room temperature and was concentrated. The residue was purified by column chromatography on silica gel (20%→30% ethyl acetate in hexanes) to afford ethyl 6-chloro-3-((4-methoxybenzyl)amino)pyridazine-4-carboxylate (6.00 g, 18.65 mmol, 41% yield) as pale-yellow solid: ¹H NMR (400 MHz, CDCl₃) δ 7.86 (br. s., 1H), 7.76 (s, 1H), 7.36 (d, J=8.8 Hz, 2H), 6.90 (d, J=8.8 Hz, 2H), 4.80 (d, J=5.3 Hz, 2H), 4.39 (q, J=7.1 Hz, 2H), 3.82 (s, 3H), 1.41 (t, J=7.0 Hz, 3H); LC/MS (ESI) m/e 322.1 [(M+H)⁺, calcd for C₁₅H₁₇C₁N₃O₃ 322.1].

Part C. Ethyl 3-amino-6-chloropyridazine-4-carboxylate

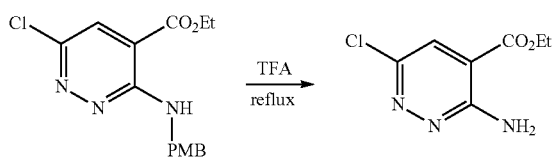

A mixture of ethyl 6-chloro-3-((4-methoxybenzyl)amino)pyridazine-4-carboxylate (1.2 g, 3.73 mmol) and TFA (5.75 ml, 74.6 mmol) was heated at reflux for 3 h. The reaction mixture was concentrated and transferred to a separatory funnel containing saturated aqueous NaHCO₃ solution (15 mL). The aqueous layer was extracted with ethyl acetate (3×20 mL). The combined organic layers were washed with brine (15 mL), dried over MgSO₄, filtered, and concentrated. The residue was purified by column chromatography on silica gel (60%→80% ethyl acetate in hexanes; 12 g column) to afford ethyl 3-amino-6-chloropyridazine-4-carboxylate (700 mg, 3.47 mmol, 93% yield) as a green solid: ¹H NMR (400 MHz, CHLOROFORM-d) δ 7.77 (s, 1H), 7.00 (s br, 2H), 4.40 (q, J=7.0 Hz, 2H), 1.40 (t, J=7.2 Hz, 3H); LCMS (ESI) m/e 202.0 [(M+H)⁺, calcd for C₇H₉N₃O₂Cl 202.6)].

Part D. Ethyl 6-chloro-2-phenylimidazo[1,2-b]pyridazine-8-carboxylate

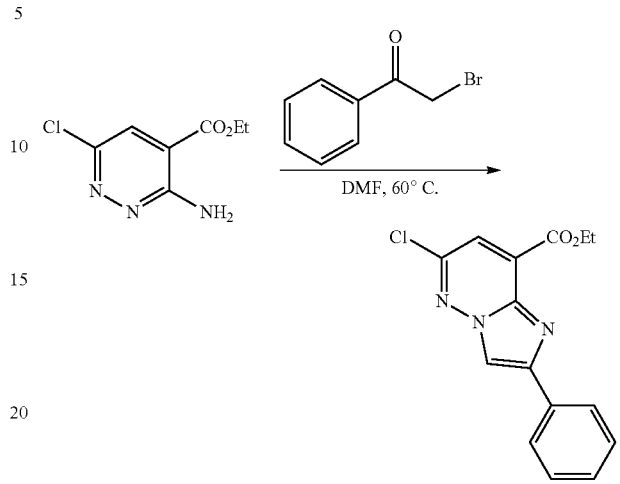

Ethyl 3-amino-6-chloropyridazine-4-carboxylate (600 mg, 2.98 mmol) was added to 2-bromo-1-phenylethanone (711 mg, 3.57 mmol) in DMF (10 mL). The solution was heated at 60° C. for 4 h. The reaction mixture was partitioned between ether (30 mL) and saturated aq. NaHCO₃ solution (20 mL). The organic layer was washed with water (20 mL) and saturated aq. NaCl solution (20 mL), dried over MgSO₄, filtered, and concentrated. The residue was purified by column chromatography on silica gel (5→20% ethyl acetate in hexanes; 40 g column) to afford ethyl 6-chloro-2-phenylimidazo[1,2-b]pyridazine-8-carboxylate (600 mg, 1.989 mmol, 67% yield) as a yellow solid: ¹H NMR (400 MHz, DMSO-d₆) δ 9.08 (s, 1H), 8.12-8.08 (m, 2H), 7.74 (s, 1H), 7.55-7.49 (m, 2H), 7.45-7.40 (m, 1H), 4.49 (q, J=7.2 Hz, 2H), 1.42 (t, J=7.0 Hz, 3H); LCMS (ESI) m/e 302.0 [(M+H)⁺, calcd for C₁₅H₁₃N₃O₂Cl 302.1].

Part E. Ethyl 2-phenylimidazo[1,2-b]pyridazine-8-carboxylate

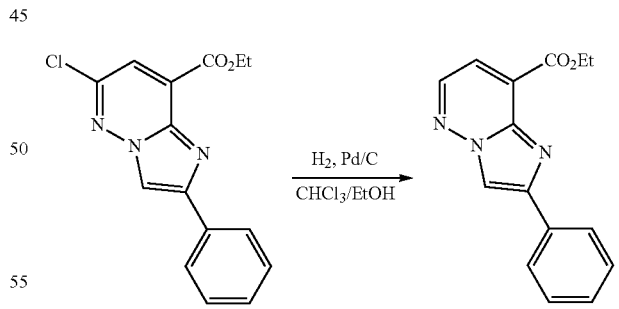

A mixture of ethyl 6-chloro-2-phenylimidazo[1,2-b]pyridazine-8-carboxylate (1.30 g, 4.31 mmol) and 10% palladium on carbon (0.459 g, 0.215 mmol) in chloroform (15 mL) and ethanol (15 mL) was stirred in a 50 mL round bottom flask under a H₂ atmosphere (balloon) for 14 h. The catalyst was removed by filtration through a pad of Celite and the filtrate was concentrated to afford ethyl 2-phenylimidazo[1,2-b]pyridazine-8-carboxylate (500 mg, 43% yield). The crude product was used directly in the next step. LCMS (ESI) m/e 268.1 [(M+H)+, calcd for C₁₅H₁₄N₃O₂ 268.1].

Part F. 2-Phenylimidazo[1,2-b]pyridazine-8-carboxylic acid

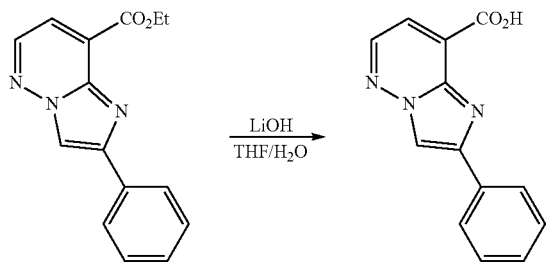 [SMILES: CCOC(=O)c1ccnn2cc(-c3ccccc3)nc12 ; "LiOH" ; O=C(O)c1ccnn2cc(-c3ccccc3)nc12]

A mixture of ethyl 2-phenylimidazo[1,2-b]pyridazine-8-carboxylate (235 mg, 0.879 mmol) and lithium hydroxide monohydrate (111 mg, 2.64 mmol) in water (0.500 mL) and THF (10 mL) was stirred at room temperature for 2 h. The solvent was concentrated to furnish 2-phenylimidazo[1,2-b]pyridazine-8-carboxylic acid (220 mg, 99% yield), which was used directly in the next step: LCMS (ESI) m/e 240.1 [(M+H)$^+$, calcd for $C_{13}H_{10}N_3O_2$ 240.1].

Preparation of 2-phenylimidazo[1,2-b]pyridazine-8-carboxylic acid via Scheme 2

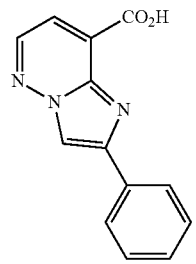 [SMILES: O=C(O)c1ccnn2cc(-c3ccccc3)nc12]

Part A. Ethyl 3,6-dichloropyridazine-4-carboxylate

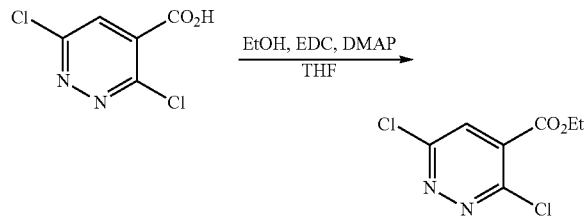

To a mixture of 3,6-dichloropyridazine-4-carboxylic acid (15.0 g, 78 mmol) in THF (150 mL) was added ethanol (18.15 mL, 311 mmol) and DMAP (0.950 g, 7.77 mmol). EDC (16.39 g, 85 mmol) was then added in portions over 1 min. The reaction was mildly exothermic. The reaction was stirred at room temperature for 16 h. The reaction mixture was transferred to a separatory funnel containing saturated aqueous NaHCO$_3$ solution (150 mL). The aqueous layer was extracted with ether (3×250 mL). The combined organic layers were washed with brine (100 mL), dried over MgSO$_4$, filtered, and concentrated. The residue was purified by column chromatography on silica gel (20%→40% ethyl acetate in hexanes; 300 g column) to afford ethyl 3,6-dichloropyridazine-4-carboxylate (13.2 g, 59.7 mmol, 77% yield) as a colorless oil: $^1$H NMR (400 MHz, CDCl$_3$) δ 7.88 (s, 1H), 4.50 (q, J=7.0 Hz, 2H), 1.46 (t, J=7.2 Hz, 3H); LCMS (ESI) m/e 221.1 [(M+H)$^+$, calcd for $C_7H_7Cl_2N_2O_2$ 221.0].

Part B. Ethyl 6-chloro-3-((4-methoxybenzyl)amino)pyridazine-4-carboxylate

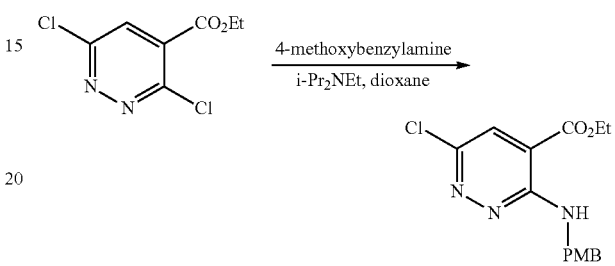

To a solution of ethyl 3,6-dichloropyridazine-4-carboxylate (10.0 g, 45.2 mmol) and (4-methoxyphenyl)methanamine (7.09 mL, 54.3 mmol) in dioxane (200 mL) was added N,N-diisopropylethylamine (23.70 mL, 136 mmol). The reaction mixture was heated at 70° C. for 1 h. The mixture was cooled to room temperature and was concentrated. The residue was purified by column chromatography on silica gel (20%→30% ethyl acetate in hexanes) to afford ethyl 6-chloro-3-((4-methoxybenzyl)amino)pyridazine-4-carboxylate (6.00 g, 18.65 mmol, 41% yield) as pale-yellow solid: $^1$H NMR (400 MHz, CDCl$_3$) δ 7.86 (br. s., 1H), 7.76 (s, 1H), 7.36 (d, J=8.8 Hz, 2H), 6.90 (d, J=8.8 Hz, 2H), 4.80 (d, J=5.3 Hz, 2H), 4.39 (q, J=7.1 Hz, 2H), 3.82 (s, 3H), 1.41 (t, J=7.0 Hz, 3H); LC/MS (ESI) m/e 322.1 [(M+H)$^+$, calcd for $C_{15}H_{17}ClN_3O_3$ 322.1].

Part C. Ethyl 3-((4-methoxybenzyl)amino)pyridazine-4-carboxylate

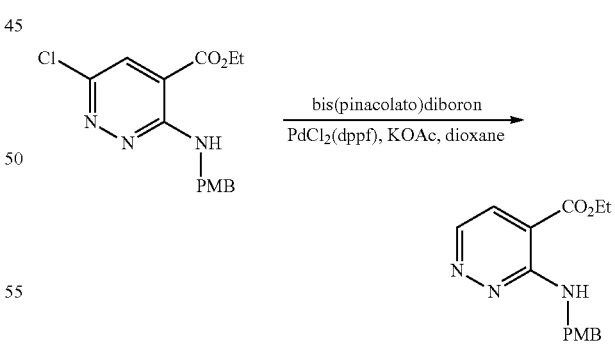

Ethyl 6-chloro-3-((4-methoxybenzyl)amino)pyridazine-4-carboxylate (3.00 g, 9.32 mmol), 4,4,4',4',5,5,5',5'-octamethyl-2,2'-bi(1,3,2-dioxaborolane) (2.60 g, 10.26 mmol), potassium acetate (2.75 g, 28.0 mmol), and dioxane (30 mL) were combined in a round bottom flask. 1,1'-bis(diphenylphosphino)ferrocenepalladium(II) dichloride. CH$_2$Cl$_2$ (0.767 g, 0.932 mmol) was added and the reaction mixture was heated at 95° C. for 6.5 h. The mixture was cooled to room temperature. The reaction mixture was filtered through a pad of Celite with ethyl acetate rinsing and was transferred to a separatory funnel containing saturated aqueous NaHCO₃ solution (50 mL) and water (50 mL). The layers were separated and the aqueous layer was extracted with ethyl acetate (2×50 mL). The combined organic layers were washed with brine (50 mL), dried over MgSO₄, filtered, and concentrated. The residue was purified by column chromatography on silica gel (40%→60% ethyl acetate in hexanes; 120 g column) to afford ethyl 3-((4-methoxybenzyl)amino)pyridazine-4-carboxylate (2.42 g, 8.42 mmol, 90% yield) as a brown oil: ¹H NMR (400 MHz, CDCl₃) δ 8.71 (d, J=5.0 Hz, 1H), 7.87 (br. s., 1H), 7.73 (d, J=4.8 Hz, 1H), 7.40-7.35 (m, 2H), 6.94-6.87 (m, 2H), 4.85 (d, J=5.3 Hz, 2H), 4.37 (q, J=7.3 Hz, 2H), 3.82 (s, 3H), 1.40 (t, J=7.2 Hz, 3H); LC/MS (ESI) m/e 288.1 [(M+H)⁺, calcd for C₁₅H₁₈N₃O₃ 288.1].

Part D. Ethyl 3-aminopyridazine-4-carboxylate

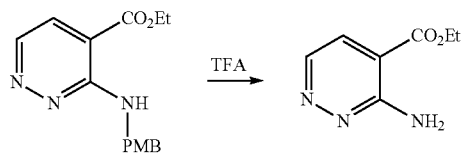

A mixture of ethyl 3-((4-methoxybenzyl)amino)pyridazine-4-carboxylate (1.5 g, 5.22 mmol) in TFA (20 mL) was heated at reflux for 3 h. The reaction mixture was concentrated and then transferred to a separatory funnel containing saturated aqueous NaHCO₃ solution (100 mL). The aqueous layer was extracted with dichloromethane (3×100 mL). The combined organic layers were washed with brine (100 mL), dried over MgSO₄, filtered, and concentrated. The residue was purified by column chromatography on silica gel (2%→10% methanol in CH₂Cl₂; 160 g column) to afford ethyl 3-aminopyridazine-4-carboxylate (752 mg, 4.50 mmol, 86% yield) as a tan solid: ¹H NMR (400 MHz, CDCl₃) δ 8.75 (d, J=5.0 Hz, 1H), 7.76 (d, J=4.8 Hz, 1H), 6.53 (br. s., 1H), 4.42 (q, J=7.1 Hz, 2H), 1.43 (t, J=7.2 Hz, 3H); LCMS (ESI) m/e 168.1 [(M+H)⁺, calcd for C₇H₁₀N₃O₂ 168.1].

Part E. Ethyl 2-phenylimidazo[1,2-b]pyridazine-8-carboxylate

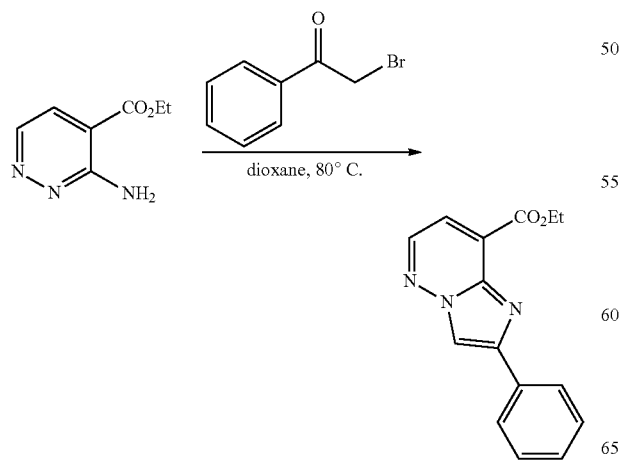

A mixture of ethyl 3-aminopyridazine-4-carboxylate (30 mg, 0.179 mmol) and 2-bromo-1-phenylethanone (107 mg, 0.538 mmol) in dioxane (1 mL) was heated at 80° C. for 3 h. The mixture was cooled to room temperature and was transferred to a separatory funnel containing saturated aqueous NaHCO₃ solution (5 mL). The aqueous layer was extracted with dichloromethane (3×10 mL). The combined organic layers were washed with brine (5 mL), dried over MgSO₄, filtered, and concentrated. The residue was purified by column chromatography on silica gel (10%→40% ethyl acetate in hexanes; 12 g column) to afford ethyl 2-phenylimidazo[1,2-b]pyridazine-8-carboxylate (9.1 mg, 0.034 mmol, 19% yield) as a yellow film: ¹H NMR (400 MHz, CDCl₃) δ 8.43 (d, J=4.8 Hz, 1H), 8.40 (s, 1H), 8.11-8.07 (m, 2H), 7.61 (d, J=4.5 Hz, 1H), 7.52-7.46 (m, 2H), 7.43-7.37 (m, 1H), 4.59 (q, J=7.0 Hz, 2H), 1.54 (t, J=7.2 Hz, 3H); LC/MS (ESI) m/e 268.1 [(M+H)⁺, calcd for C₁₅H₁₄N₃O₂ 268.1].

Part F. 2-Phenylimidazo[1,2-b]pyridazine-8-carboxylic acid

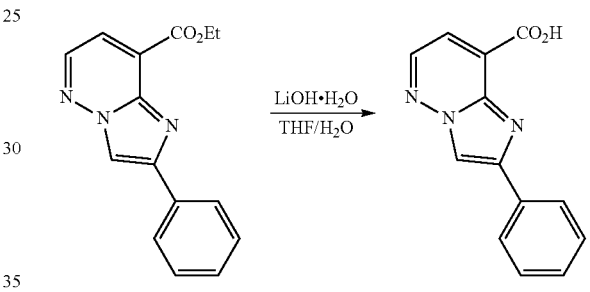

A mixture of ethyl 2-phenylimidazo[1,2-b]pyridazine-8-carboxylate (235 mg, 0.879 mmol) and lithium hydroxide monohydrate (111 mg, 2.64 mmol) in water (0.500 mL) and THF (10 mL) was stirred at room temperature for 2 h. The solvent was concentrated to furnish 2-phenylimidazo[1,2-b]pyridazine-8-carboxylic acid (220 mg, 99% yield), which was used directly in the next step: LCMS (ESI) m/e 240.1 [(M+H)⁺, calcd for C₁₃H₁₀N₃O₂ 240.1].

Example 1

2-Phenyl-N-(pyridin-3-yl)imidazo[1,2-b]pyridazine-8-carboxamide

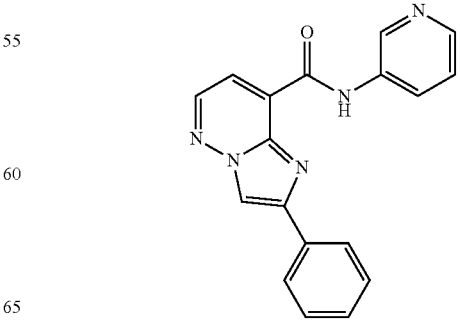

To a solution of 2-phenylimidazo[1,2-b]pyridazine-8-carboxylic acid (35 mg, 0.146 mmol) and pyridin-3-amine (6.0 mg, 0.062 mmol) in DMF (1 mL) was added N,N-diisopropylethylamine (0.036 mL, 0.210 mmol) followed by HATU (32 mg, 0.084 mmol). The reaction mixture was stirred at rt for 14 h. The reaction mixture was concentrated and the product was purified by reverse phase HPLC (Method A) to afford and 2-phenyl-N-(pyridin-3-yl)imidazo[1,2-b]pyridazine-8-carboxamide, 2 TFA (5.5 mg, 42% yield) as a yellow amorphous solid: $^1$H NMR (500 MHz, DMSO-$d_6$) δ 12.11 (s, 1H), 9.15 (s, 1H), 9.08 (d, J=2.3 Hz, 1H), 8.80 (d, J=4.6 Hz, 1H), 8.48 (dd, J=4.7, 1.4 Hz, 1H), 8.41-8.38 (m, 1H), 8.20 (dd, J=8.3, 1.1 Hz, 2H), 7.88 (d, J=4.7 Hz, 1H), 7.61-7.54 (m, 3H), 7.47-7.42 (m, 1H); LC/MS (ESI) m/e 316.1 [(M+H)$^+$, calcd for $C_{18}H_{14}N_5O$ 316.1]; HPLC (Method A): $t_R$=9.32 min; (Method B) $t_R$=9.56 min.

Example 2

N-(4-Methylpyridin-3-yl)-2-phenylimidazo[1,2-b]pyridazine-8-carboxamide

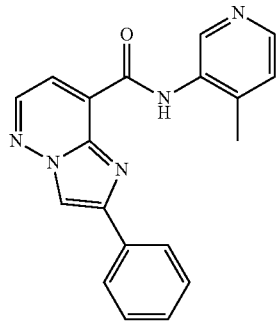 [SMILES: Cc1ccncc1NC(=O)c1ccnn2cc(-c3ccccc3)nc12]

To a solution of 2-phenylimidazo[1,2-b]pyridazine-8-carboxylic acid (30 mg, 0.125 mmol), 4-methylpyridin-3-amine (27.1 mg, 0.251 mmol), and N,N-diisopropylethylamine (0.131 mL, 0.752 mmol) in DMF (2 mL) at rt was added HATU (95 mg, 0.251 mmol).

The reaction mixture was stirred at rt for 6 h. The reaction mixture was transferred to a separatory funnel containing saturated aqueous NaHCO$_3$ solution (15 mL). The aqueous layer was extracted with ethyl acetate (3×15 mL). The combined organic layers were washed with brine (20 mL), dried over MgSO$_4$, filtered, and concentrated. The residue was purified by column chromatography on silica gel (20%→60% ethyl acetate in hexanes; 12 g column) to afford N-(4-methylpyridin-3-yl)-2-phenylimidazo[1,2-b]pyridazine-8-carboxamide (16 mg, 0.046 mmol, 37% yield) as a yellow solid: $^1$H NMR (400 MHz, DMSO-$d_6$) δ 11.75 (s, 1H), 9.35 (s, 1H), 9.16 (s, 1H), 8.82 (d, J=4.8 Hz, 1H), 8.35 (d, J=4.8 Hz, 1H), 8.21-8.11 (m, 2H), 7.94 (d, J=4.8 Hz, 1H), 7.60-7.51 (m, 2H), 7.48-7.40 (m, 2H), 2.61 (s, 3H); LCMS (ESI) m/e 330.2 [(M+H)$^+$, calcd for $C_{19}H_{16}N_5O$ 330.1]; HPLC (Method A): $t_R$=8.96 min; (Method B) $t_R$=10.00 min.

Example 3

N-(4-Isopropoxypyridin-3-yl)-2-phenylimidazo[1,2-b]pyridazine-8-carboxamide

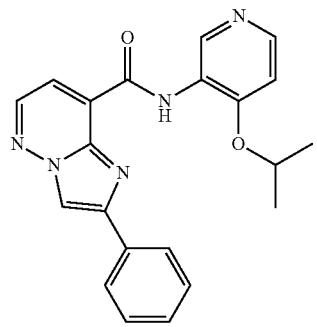 [SMILES: CC(C)Oc1ccncc1NC(=O)c1ccnn2cc(-c3ccccc3)nc12]

Part A. 6-Chloro-N-(4-isopropoxypyridin-3-yl)-2-phenylimidazo[1,2-b]pyridazine-8-carboxamide

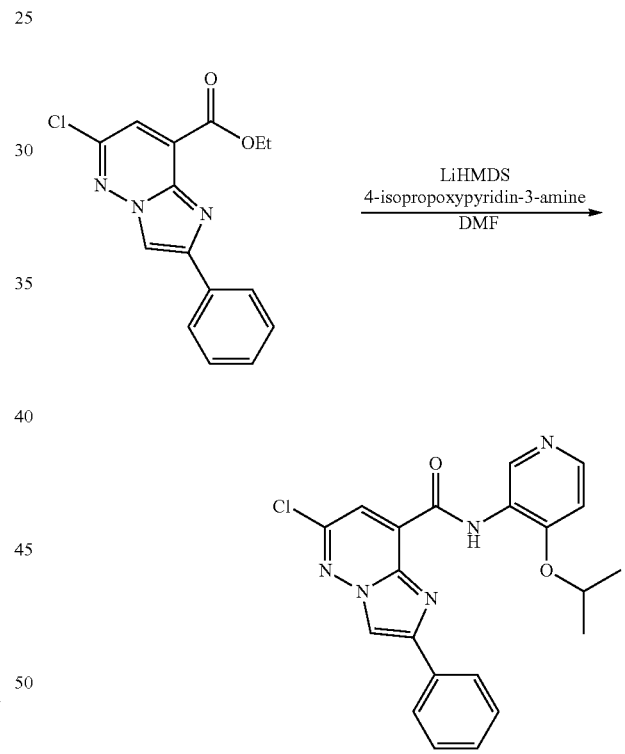

To a mixture of ethyl 6-chloro-2-phenylimidazo[1,2-b]pyridazine-8-carboxylate (50 mg, 0.166 mmol), 4-isopropoxypyridin-3-amine, 2 HCl (74.6 mg, 0.331 mmol) in DMF (1 mL) was added LiHMDS (1M in THF) (0.679 mL, 0.679 mmol) and the reaction mixture was stirred at rt for 2 h. The reaction mixture was transferred to a separatory funnel containing saturated aqueous NaHCO$_3$ solution (15 mL). The aqueous layer was extracted with ethyl acetate (3×15 mL). The combined organic layers were washed with brine (15 mL), dried over MgSO$_4$, filtered, and concentrated.

The residue was purified by column chromatography on silica gel (40%→60% ethyl acetate in hexanes; 12 g column) to afford 6-chloro-N-(4-isopropoxypyridin-3-yl)-2-phenylimidazo[1,2-b]pyridazine-8-carboxamide (25 mg, 0.056 mmol, 34% yield) as a green solid: ¹H NMR (400 MHz, CHLOROFORM-d) δ 11.84 (s, 1H), 9.64 (s, 1H), 8.37 (d, J=5.8 Hz, 1H), 8.34 (s, 1H), 8.08-8.03 (m, 2H), 8.00 (s, 1H), 7.55-7.41 (m, 3H), 6.92 (d, J=5.8 Hz, 1H), 4.77 (dt, J=12.2, 6.2 Hz, 1H), 1.39 (d, J=6.0 Hz, 6H); LCMS (ESI) m/e 408.2 [(M+H)+, calcd for $C_{21}H_{19}N_5O_2Cl$ 408.1].

Part B. N-(4-Isopropoxypyridin-3-yl)-2-phenylimidazo[1,2-b]pyridazine-8-carboxamide

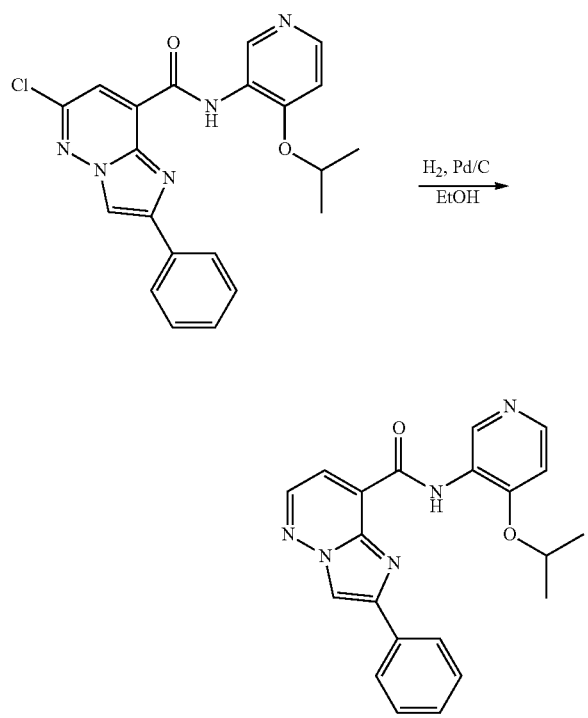 [SMILES: "EtOH" ; CC(C)Oc1ccncc1NC(=O)c1cc(Cl)nn2cc(-c3ccccc3)nc12 ; CC(C)Oc1ccncc1NC(=O)c1ccnn2cc(-c3ccccc3)nc12]

A mixture of 6-chloro-N-(4-isopropoxypyridin-3-yl)-2-phenylimidazo[1,2-b]pyridazine-8-carboxamide (30 mg, 0.074 mmol) and 10% palladium on carbon (15.66 mg, 0.015 mmol) in EtOH (2 mL) was placed under hydrogen at 45 psi in parr shaker for 6 h. The mixture was filtered through a pad of Celite and was concentrated. The residue was purified by reverse phase HPLC (Method A) to afford N-(4-isopropoxypyridin-3-yl)-2-phenylimidazo[1,2-b]pyridazine-8-carboxamide, 2 TFA (12 mg, 0.020 mmol, 27% yield) as a yellow solid: ¹H NMR (400 MHz, DMSO-d₆) δ 12.12 (s, 1H), 9.65 (s, 1H), 9.18 (s, 1H), 8.83 (d, J=4.8 Hz, 1H), 8.66 (d, J=6.5 Hz, 1H), 8.23-8.18 (m, 2H), 7.96 (d, J=4.5 Hz, 1H), 7.78 (d, J=6.8 Hz, 1H), 7.59-7.53 (m, 2H), 7.52-7.44 (m, 1H), 5.19 (quin, J=6.1 Hz, 1H), 1.42 (d, J=6.0 Hz, 6H); LCMS (ESI) m/e 374.2 [(M+H)⁺, calcd for $C_{21}H_{20}N_5O_2$ 374.2]; HPLC (Method A): $t_R$=10.13 min; (Method B) $t_R$=10.62 min.

Example 4

2-Phenyl-N-(4-(2,2,2-trifluoroethoxy)pyridin-3-yl)imidazo[1,2-b]pyridazine-8-carboxamide

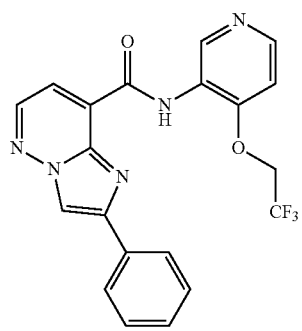 [SMILES: O=C(Nc1cnccc1OCC(F)(F)F)c1ccnn2cc(-c3ccccc3)nc12]

To a solution of 2-phenylimidazo[1,2-b]pyridazine-8-carboxylic acid (20 mg, 0.084 mmol), 4-(2,2,2-trifluoroethoxy)pyridin-3-amine (32.1 mg, 0.167 mmol), and N,N-diisopropylethylamine (0.088 mL, 0.502 mmol) in DMF (2 mL) at rt was added HATU (63.6 mg, 0.167 mmol). The reaction mixture was stirred at rt for 2 h. The mixture was transferred to a separatory funnel containing saturated aqueous NaHCO₃ solution (15 mL). The aqueous layer was extracted with ethyl acetate (3×15 mL). The combined organic layers were washed with brine (20 mL), dried over MgSO₄, filtered, and concentrated. The residue was purified by column chromatography on silica gel (30%→80% ethyl acetate in hexanes; 12 g column) to afford 2-phenyl-N-(4-(2,2,2-trifluoroethoxy)pyridin-3-yl)imidazo[1,2-b]pyridazine-8-carboxamide (15 mg, 0.034 mmol, 41% yield) as a yellow solid: ¹H NMR (400 MHz, DMSO-d₆) δ 11.95 (s, 1H), 9.52 (s, 1H), 9.14 (s, 1H), 8.80 (d, J=4.8 Hz, 1H), 8.43 (d, J=5.8 Hz, 1H), 8.17 (d, J=7.3 Hz, 2H), 7.93 (d, J=4.8 Hz, 1H), 7.60-7.49 (m, 3H), 7.47-7.38 (m, 1H), 5.21 (q, J=8.8 Hz, 2H); LCMS (ESI) m/e 414.0 [(M+H)⁺, calcd for $C_{20}H_{15}N_5O_2F_3$ 414.1]; HPLC (Method C): $t_R$=10.95 min; (Method D) $t_R$=11.90 min.

Example 5

N-(4-(Methylsulfonyl)pyridin-3-yl)-2-phenylimidazo[1,2-b]pyridazine-8-carboxamide

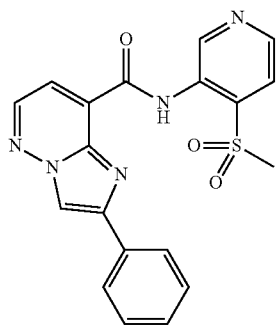 [SMILES: CS(=O)(=O)c1ccncc1NC(=O)c1ccnn2cc(-c3ccccc3)nc12]

To a suspension of 2-phenylimidazo[1,2-b]pyridazine-8-carboxylic acid (10 mg, 0.042 mmol) in dichloromethane (1 mL) at 0° C. was added DMF (0.647 μl, 8.36 μmol) and oxalyl chloride (10.98 μl, 0.125 mmol). The mixture was stirred at room temperature for 1 hour. The mixture was concentrated and the residue was dried under vacuum for 1 hour. The residue was suspended in dichloromethane (1 mL) followed by the addition of triethylamine (0.023 mL, 0.167 mmol), DMAP (10.21 mg, 0.084 mmol), and 4-(methylsulfonyl)pyridin-3-amine (7.92 mg, 0.046 mmol) at 0° C. The cooling bath was removed and the reaction was stirred at room temperature for 4 h. The reaction mixture was transferred to a separatory funnel containing saturated aqueous NaHCO$_3$ solution (15 mL). The aqueous layer was extracted with CH$_2$Cl$_2$ (3×15 mL). The combined organic layers were washed with brine (15 mL), dried over MgSO$_4$, filtered, and concentrated. The residue was purified by reverse phase HPLC (Method A) followed by prep TLC (5% methanol in dichloromethane) to afford N-(4-(methylsulfonyl)pyridin-3-yl)-2-phenylimidazo[1,2-b]pyridazine-8-carboxamide (2.0 mg, 5.03 μmol, 12% yield) as a yellow solid: $^1$H NMR (400 MHz, METHANOL-d$_4$) δ 9.53 (s, 1H), 8.76 (s, 1H), 8.74 (d, J=5.3 Hz, 1H), 8.67 (d, J=4.8 Hz, 1H), 8.29 (d, J=1.5 Hz, 1H), 8.27 (s, 1H), 8.06 (d, J=5.0 Hz, 1H), 7.99 (d, J=4.5 Hz, 1H), 7.50-7.43 (m, 3H), 3.29 (s, 3H); LCMS (ESI) m/e 394.1 [(M+H)$^+$, calcd for C$_{19}$H$_{16}$N$_5$O$_3$S 394.1]; HPLC (Method A): t$_R$=16.74 min; (Method B) t$_R$=17.89 min.

Example 6

2-Phenyl-N-(4-phenylpyridin-3-yl)imidazo[1,2-b]pyridazine-8-carboxamide

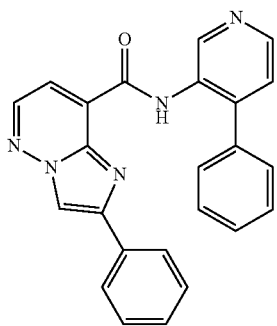 [SMILES: O=C(Nc1cnccc1-c1ccccc1)c1ccnn2cc(-c3ccccc3)nc12]

To a solution of 2-phenylimidazo[1,2-b]pyridazine-8-carboxylic acid (50 mg, 0.209 mmol), 4-phenylpyridin-3-amine (71.1 mg, 0.418 mmol), and N,N-diisopropylethylamine (0.219 mL, 1.254 mmol) in DMF (1 mL) was added HATU (159 mg, 0.418 mmol). The reaction mixture was stirred at rt for 2 h. The mixture was concentrated and the residue was purified by column chromatography on silica gel (30%→50% ethyl acetate in hexanes; 12 g column) to afford 2-phenyl-N-(4-phenylpyridin-3-yl)imidazo[1,2-b]pyridazine-8-carboxamide (32 mg, 0.081 mmol, 39% yield) as a tan solid: $^1$H NMR (400 MHz, DMSO-d$_6$) δ 11.83 (s, 1H), 9.37 (s, 1H), 9.03 (s, 1H), 8.78 (d, J=4.8 Hz, 1H), 8.54 (d, J=5.0 Hz, 1H), 7.91 (d, J=4.8 Hz, 1H), 7.77-7.66 (m, 2H), 7.52-7.43 (m, 5H), 7.38 (dd, J=5.0, 1.8 Hz, 3H), 7.35-7.27 (m, 1H); LCMS (ESI) m/e 392.3 [(M+H)+, calcd for C$_{24}$H$_{18}$N$_5$O 392.2]; HPLC (Method A): t$_R$=8.87 min; (Method B) t$_R$=9.30 min.

Example 7

N-(4-(4-Fluorophenyl)pyridin-3-yl)-2-phenylimidazo[1,2-b]pyridazine-8-carboxamide

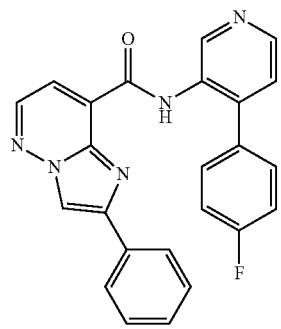 [SMILES: O=C(Nc1cnccc1-c1ccc(F)cc1)c1ccnn2cc(-c3ccccc3)nc12]

To a solution of 2-phenylimidazo[1,2-b]pyridazine-8-carboxylic acid (30 mg, 0.125 mmol), 4-(4-fluorophenyl)pyridin-3-amine (47.2 mg, 0.251 mmol), and N,N-diisopropylethylamine (0.131 mL, 0.752 mmol) in DMF (1 mL) was added HATU (95 mg, 0.251 mmol). The reaction mixture was stirred at rt for 12 h. The solvent was evaporated and the residue was purified by reverse phase HPLC (Method A) to afford N-(4-(4-fluorophenyl)pyridin-3-yl)-2-phenylimidazo[1,2-b]pyridazine-8-carboxamide, 2 TFA (22 mg, 0.034 mmol, 27% yield) as a yellow solid: $^1$H NMR (400 MHz, DMSO-d$_6$) δ 11.92 (s, 1H), 9.48 (s, 1H), 9.06 (s, 1H), 8.79 (d, J=4.8 Hz, 1H), 8.59 (d, J=5.3 Hz, 1H), 7.93 (d, J=4.8 Hz, 1H), 7.86-7.80 (m, 2H), 7.62 (d, J=5.0 Hz, 1H), 7.49-7.42 (m, 2H), 7.42-7.37 (m, 3H), 7.33-7.24 (m, 2H); LCMS (ESI) m/e 410.2 [(M+H)$^+$, calcd for C$_{24}$H$_{17}$N$_5$OF 410.1]; HPLC (Method A): t$_R$=10.75 min; (Method B) t$_R$=11.06 min.

Example 8

N-(4-(4-Cyanophenyl)pyridin-3-yl)-2-phenylimidazo[1,2-b]pyridazine-8-carboxamide

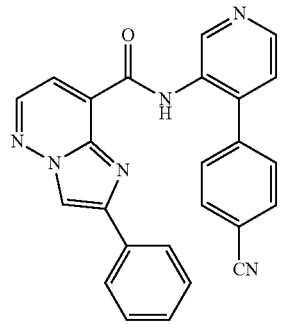 [SMILES: N#Cc1ccc(-c2ccncc2NC(=O)c2ccnn3cc(-c4ccccc4)nc23)cc1]

To a solution of 2-phenylimidazo[1,2-b]pyridazine-8-carboxylic acid (25 mg, 0.105 mmol), 4-(3-aminopyridin-4-yl)benzonitrile (40.8 mg, 0.209 mmol), and N,N-diisopropylethylamine (0.110 mL, 0.627 mmol) in DMF (1 mL) was added HATU (79 mg, 0.209 mmol). The reaction mixture was stirred at rt for 12 h. The solvent was evaporated and the residue was purified by reverse phase HPLC (Method A) to afford N-(4-(4-cyanophenyl)pyridin-3-yl)-2-phenylimidazo[1,2-b]pyridazine-8-carboxamide, 2 TFA (8 mg, 0.012 mmol, 11% yield) as a yellow solid: $^1$H NMR (400 MHz, DMSO-$d_6$) δ 11.89 (s, 1H), 9.47 (s, 1H), 9.06 (s, 1H), 8.79 (d, J=4.8 Hz, 1H), 8.61 (d, J=5.0 Hz, 1H), 8.00-7.88 (m, 5H), 7.60 (d, J=5.3 Hz, 1H), 7.46-7.38 (m, 5H); LCMS (ESI) m/e 417.2 [(M+H)+, calcd for $C_{25}H_{17}N_6O$ 417.4]; HPLC (Method A): $t_R$=10.63 min; (Method B) $t_R$=10.83 min.

Example 9

2-Phenyl-N-(4-(piperidin-1-yl)pyridin-3-yl)imidazo[1,2-b]pyridazine-8-carboxamide

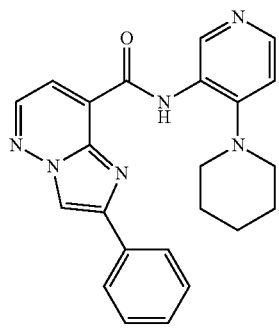

To a solution of 2-phenylimidazo[1,2-b]pyridazine-8-carboxylic acid (40 mg, 0.167 mmol), 4-(piperidin-1-yl)pyridin-3-amine, 2 HCl (84 mg, 0.334 mmol), and N,N-diisopropylethylamine (0.175 mL, 1.003 mmol) in DMF (1 mL) was added HATU (127 mg, 0.334 mmol). The reaction mixture was stirred at rt for 2 h. The solvent was evaporated and the residue was purified by reverse phase HPLC (Method A) to afford 2-phenyl-N-(4-(piperidin-1-yl)pyridin-3-yl)imidazo[1,2-b]pyridazine-8-carboxamide, 2 TFA (41 mg, 0.063 mmol, 38% yield) as a tan solid: $^1$H NMR (400 MHz, DMSO-$d_6$) δ 11.79 (s, 1H), 9.21 (s, 1H), 9.04 (d, J=0.5 Hz, 1H), 8.84 (d, J=4.5 Hz, 1H), 8.44 (dd, J=6.8, 1.0 Hz, 1H), 8.26-8.12 (m, 2H), 7.94 (d, J=4.8 Hz, 1H), 7.61-7.33 (m, 4H), 3.53-3.38 (m, 4H), 1.61 (br. s., 4H), 1.46 (d, J=4.5 Hz, 2H); LCMS (APCI) m/e 399.3 [(M+H)+, calcd for $C_{23}H_{23}N_6O$ 399.2]; HPLC (Method A): $t_R$=16.70 min; (Method B) $t_R$=18.07 min.

Example 10

N-(4-(4-Cyanopiperidin-1-yl)pyridin-3-yl)-2-phenylimidazo[1,2-b]pyridazine-8-carboxamide

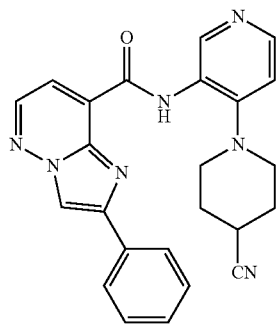 [SMILES: N#CC1CCN(c2ccncc2NC(=O)c2ccnn3cc(-c4ccccc4)nc23)CC1]

To a solution of 2-phenylimidazo[1,2-b]pyridazine-8-carboxylic acid (30 mg, 0.125 mmol), 1-(3-aminopyridin-4-yl)piperidine-4-carbonitrile (50.7 mg, 0.251 mmol), and N,N-diisopropylethylamine (0.131 mL, 0.752 mmol) in DMF (1 mL) was added HATU (95 mg, 0.251 mmol). The reaction mixture was stirred at rt for 12 h. The mixture was concentrated and the residue was purified by reverse phase HPLC (Method A) followed by prep TLC (10% methanol in methylene chloride) to afford N-(4-(4-cyanopiperidin-1-yl)pyridin-3-yl)-2-phenylimidazo[1,2-b]pyridazine-8-carboxamide (10 mg, 0.022 mmol, 18% yield) as a yellow solid: $^1$H NMR (400 MHz, CHLOROFORM-d) δ 11.83 (br. s., 1H), 9.45 (s, 1H), 8.59 (d, J=4.8 Hz, 1H), 8.41 (s, 2H), 8.07-7.95 (m, 3H), 7.56-7.45 (m, 3H), 7.02 (d, J=5.3 Hz, 1H), 3.30-3.18 (m, 2H), 3.13-3.00 (m, 2H), 2.55-2.44 (m, 1H), 2.04-1.92 (m, 2H), 1.91-1.80 (m, 2H); LCMS (ESI) m/e 424.2 [(M+H)+, calcd for $C_{24}H_{22}N_7O$ 424.3]; HPLC (Method A): $t_R$=8.91 min; (Method B) $t_R$=9.57 min.

Example 11

N-(4-(4-Fluoropiperidin-1-yl)pyridin-3-yl)-2-phenylimidazo[1,2-b]pyridazine-8-carboxamide

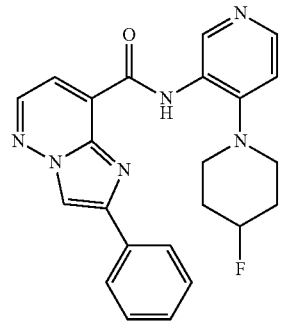 [SMILES: O=C(Nc1cnccc1N1CCC(F)CC1)c1ccnn2cc(-c3ccccc3)nc12]

To a solution of 2-phenylimidazo[1,2-b]pyridazine-8-carboxylic acid (30 mg, 0.125 mmol), 4-(4-fluoropiperidin-1-yl)pyridin-3-amine (49.0 mg, 0.251 mmol), and N,N-diisopropylethylamine (0.131 mL, 0.752 mmol) in DMF (2 mL) was added HATU (95 mg, 0.251 mmol). The reaction mixture was stirred at rt for 6 h. The reaction mixture was transferred to a separatory funnel containing saturated aqueous NaHCO$_3$ solution (15 mL). The aqueous layer was extracted with ethyl acetate (3×15 mL). The combined organic layers were washed with brine (20 mL), dried over MgSO$_4$, filtered, and concentrated. The residue was purified by column chromatography on silica gel (20%→60% ethyl acetate in hexanes; 12 g column) to afford N-(4-(4-fluoropiperidin-1-yl)pyridin-3-yl)-2-phenylimidazo[1,2-b]pyridazine-8-carboxamide (16 mg, 0.038 mmol, 31% yield) as a yellow solid: $^1$H NMR (400 MHz, DMSO-$d_6$) δ 11.74 (s, 1H), 9.18 (s, 2H), 8.82 (d, J=4.5 Hz, 1H), 8.33 (d, J=5.5 Hz, 1H), 8.22-8.16 (m, 2H), 7.96 (d, J=4.5 Hz, 1H), 7.56-7.50 (m, 2H), 7.48-7.41 (m, 1H), 4.68-4.46 (m, 1H), 3.26-3.15 (m, 2H), 3.12-3.03 (m, 2H), 2.00-1.86 (m, 2H), 1.79 (d, J=13.8 Hz, 2H); LCMS (ESI) m/e 417.1 [(M+H)+, calcd for $C_{23}H_{22}N_6OF$ 417.2]; HPLC (Method A): $t_R$=9.96 min; (Method B) $t_R$=10.56 min.

Example 12

N-(4-(4,4-Difluoropiperidin-1-yl)pyridin-3-yl)-2-phenylimidazo[1,2-b]pyridazine-8-carboxamide

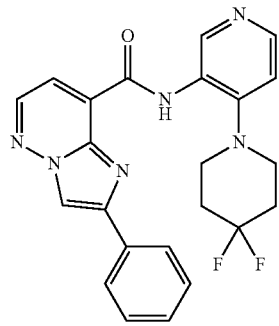 [SMILES: O=C(Nc1cnccc1N1CCC(F)(F)CC1)c1ccnn2cc(-c3ccccc3)nc12]

To a solution of 2-phenylimidazo[1,2-b]pyridazine-8-carboxylic acid, TFA (100 mg, 0.283 mmol) and 4-(4,4-difluoropiperidin-1-yl)pyridin-3-amine (72.4 mg, 0.340 mmol) in DMF (2 mL) was added N,N-diisopropylethylamine (0.247 mL, 1.415 mmol) followed by HATU (129 mg, 0.340 mmol). The reaction mixture was stirred at rt for 18 h. The mixture was concentrated and the product was purified by reverse phase HPLC (Method A) to afford N-(4-(4,4-difluoropiperidin-1-yl)pyridin-3-yl)-2-phenylimidazo[1,2-b]pyridazine-8-carboxamide (58 mg, 0.125 mmol, 44% yield) as a yellow amorphous solid: $^1$H NMR (400 MHz, DMSO-$d_6$) δ 11.77 (s, 1H), 9.21 (s, 1H), 9.17 (s, 1H), 8.83 (d, J=4.8 Hz, 1H), 8.35 (d, J=5.5 Hz, 1H), 8.17 (d, J=7.0 Hz, 2H), 7.97 (d, J=4.8 Hz, 1H), 7.58-7.50 (m, 2H), 7.48-7.42 (m, 1H), 7.27 (d, J=5.5 Hz, 1H), 3.22 (t, J=5.0 Hz, 4H), 2.10-1.95 (m, 4H); LC/MS (ESI) m/e 435.1 [(M+H)$^+$, calcd for $C_{23}H_{21}F_2N_6O$ 435.2]; HPLC (Method A): $t_R$=10.26 min; (Method B) $t_R$=10.24 min.

Example 13

N-(4-Morpholinopyridin-3-yl)-2-phenylimidazo[1,2-b]pyridazine-8-carboxamide

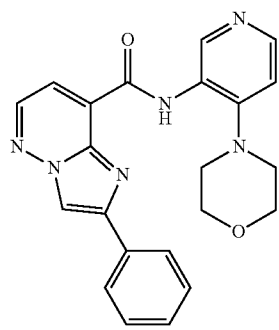

Part A. 6-Chloro-2-phenylimidazo[1,2-b]pyridazine-8-carboxylic acid

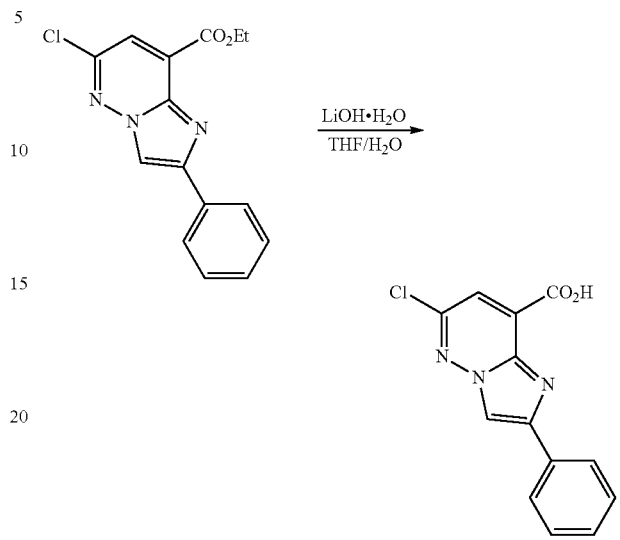

A mixture of ethyl 6-chloro-2-phenylimidazo[1,2-b]pyridazine-8-carboxylate (55 mg, 0.182 mmol) and lithium hydroxide monohydrate (22.95 mg, 0.547 mmol) in water (0.150 mL) and THF (3 mL) was stirred at room temperature for 2 h. The solvent was concentrated to afford 6-chloro-2-phenylimidazo[1,2-b]pyridazine-8-carboxylic acid (50 mg, 100% yield). The product was used directly in the next step. LCMS (ESI) m/e 274.1 [(M+H)$^+$, calcd for $C_{13}H_9N_3O_2Cl$ 274.0].

Part B. 6-Chloro-N-(4-morpholinopyridin-3-yl)-2-phenylimidazo[1,2-b]pyridazine-8-carboxamide

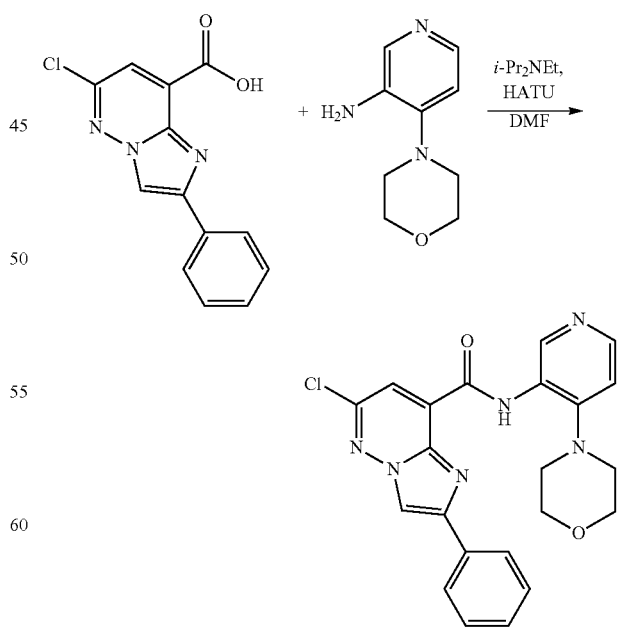

To a solution of 6-chloro-2-phenylimidazo[1,2-b]pyridazine-8-carboxylic acid (50 mg, 0.183 mmol), 4-morpholinopyridin-3-amine (65.5 mg, 0.365 mmol), and N,N-diisopropylethylamine (0.128 mL, 0.731 mmol) in DMF (3 mL) was added HATU (139 mg, 0.365 mmol). The reaction mixture was stirred at rt for 4 h. The mixture was concentrated and the residue was purified by silica gel chromatography (30→40% ethyl acetate in hexanes, 12 g column) to afford 6-chloro-N-(4-morpholinopyridin-3-yl)-2-phenylimidazo[1,2-b]pyridazine-8-carboxamide (32 mg, 0.074 mmol, 40% yield): $^1$H NMR (400 MHz, CHLOROFORM-d) δ 11.79 (s, 1H), 9.37 (s, 1H), 8.42 (d, J=5.5 Hz, 1H), 8.36 (s, 1H), 8.11-8.04 (m, 2H), 8.02 (s, 1H), 7.56-7.41 (m, 3H), 7.02 (d, J=5.5 Hz, 1H), 3.75-3.66 (m, 4H), 3.16-3.06 (m, 4H); LCMS (ESI) m/e 435.2 [(M+H)$^+$, calcd for $C_{22}H_{20}ClN_6O_2$ 435.1].

Part C. N-(4-Morpholinopyridin-3-yl)-2-phenylimidazo[1,2-b]pyridazine-8-carboxamide

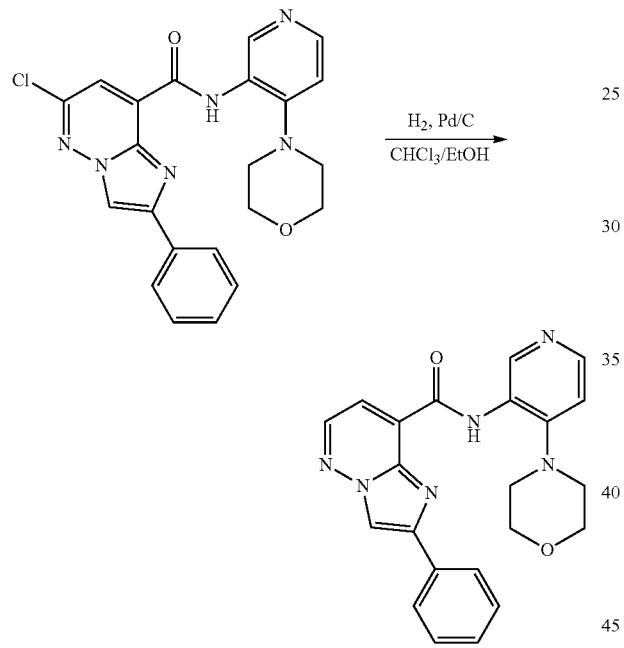

A mixture of 6-chloro-N-(4-morpholinopyridin-3-yl)-2-phenylimidazo[1,2-b]pyridazine-8-carboxamide (30 mg, 0.069 mmol) and 10% palladium on carbon (14.68 mg, 0.014 mmol) in CHCl$_3$ (5 mL) and MeOH (5.00 mL) was placed under hydrogen at 45 psi and was shaken on the Parr shaker for 3 h. The mixture was filtered through a pad of Celite and the filtrate was concentrated. The residue was purified by reverse phase HPLC (Method A) to afford N-(4-morpholinopyridin-3-yl)-2-phenylimidazo[1,2-b]pyridazine-8-carboxamide, 2 TFA (13 mg, 0.020 mmol, 30% yield) as a yellow amorphous solid: $^1$H NMR (400 MHz, DMSO-d$_6$) δ 11.92 (s, 1H), 9.21 (s, 1H), 9.14 (s, 1H), 8.84 (d, J=4.8 Hz, 1H), 8.51 (d, J=6.3 Hz, 1H), 8.24 (d, J=7.3 Hz, 2H), 7.95 (d, J=4.8 Hz, 1H), 7.60-7.53 (m, 3H), 7.50-7.43 (m, 1H), 3.65 (d, J=4.8 Hz, 4H) (4H obscured by water peak at 3.54 ppm); LCMS (ESI) m/e 401.3 [(M+H)$^+$, calcd for $C_{22}H_{21}N_6O_2$ 401.2]; HPLC (Method A): t$_R$=9.18 min; (Method B) t$_R$=9.79 min.

Example 14

N-(4-(2-Methylmorpholino)pyridin-3-yl)-2-phenylimidazo[1,2-b]pyridazine-8-carboxamide

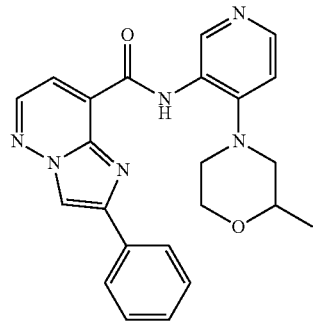 [SMILES: CC1CN(c2ccncc2NC(=O)c2ccnn3cc(-c4ccccc4)nc23)CCO1]

To a solution of 2-phenylimidazo[1,2-b]pyridazine-8-carboxylic acid (30 mg, 0.125 mmol), 4-(2-methylmorpholino)pyridin-3-amine (48.5 mg, 0.251 mmol) and N,N-diisopropylethylamine (0.131 mL, 0.752 mmol) in DMF (1 mL) was added HATU (95 mg, 0.251 mmol). The reaction mixture was stirred at rt for 2 h. The solvent was evaporated and the residue was purified by column chromatography on silica gel (30% 50% ethyl acetate in hexanes; 12 g column) to afford N-(4-(2-methylmorpholino)pyridin-3-yl)-2-phenylimidazo[1,2-b]pyridazine-8-carboxamide (22 mg, 0.053 mmol, 42% yield) as a yellow solid: $^1$H NMR (400 MHz, DMSO-d$_6$) δ 11.83 (s, 1H), 9.19 (d, J=3.3 Hz, 2H), 8.82 (d, J=4.8 Hz, 1H), 8.35 (d, J=5.5 Hz, 1H), 8.27-8.22 (m, 2H), 7.95 (d, J=4.8 Hz, 1H), 7.54 (t, J=7.4 Hz, 2H), 7.49-7.44 (m, 1H), 7.21 (d, J=5.3 Hz, 1H), 3.77-3.52 (m, 3H), 2.92-2.89 (m, 2H), 2.76-2.73 (m, 2H), 0.95 (d, J=6.3 Hz, 3H); LCMS (ESI) m/e 415.2 [(M+H)+, calcd for $C_{23}H_{23}N_6O_2$ 415.2]; HPLC (Method A): t$_R$=10.04 min; (Method B) t$_R$=10.15 min.

Example 15

N-(4-(2-Methylmorpholino)pyridin-3-yl)-2-phenylimidazo[1,2-b]pyridazine-8-carboxamide

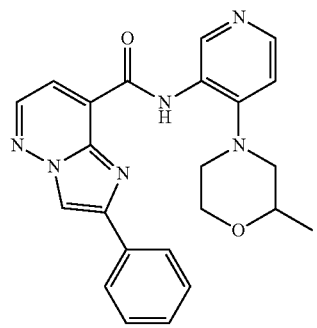 [SMILES: CC1CN(c2ccncc2NC(=O)c2ccnn3cc(-c4ccccc4)nc23)CCO1]

Racemic N-(4-(2-Methylmorpholino)pyridin-3-yl)-2-phenylimidazo[1,2-b]pyridazine-8-carboxamide was subjected to chiral separation (Column: ChiralPak AS-H, 30×250 mm, 5 μm; Mobile Phase: 15% EtOH (ww 0.1% DEA)/85% C02; 120 bar; 35° C.; 70 mL/min; 370 nm). Analytical data for Peak 1 (Enantiomer 1): $^1$H NMR (400 MHz, DMSO-d$_6$) δ 11.83 (s, 1H), 9.19 (d, J=3.3 Hz, 2H), 8.82 (d, J=4.8 Hz, 1H), 8.35 (d, J=5.5 Hz, 1H), 8.27-8.22 (m, 2H), 7.95 (d, J=4.8 Hz, 1H), 7.54 (t, J=7.4 Hz, 2H), 7.49-7.44 (m, 1H), 7.21 (d, J=5.3 Hz, 1H), 3.77-3.52 (m, 3H), 2.92-2.89 (m, 2H), 2.76-2.73 (m, 2H), 0.95 (d, J=6.3 Hz, 3H); LCMS (ESI) m/e 415.2 [(M+H)$^+$, calcd for C$_{23}$H$_{23}$N$_6$O$_2$ 415.2]; Analytical chiral HPLC (Column: ChiralPak AS-H, 4.6×250 mm, 5 μm; Mobile Phase: 15% EtOH (ww 0.1% DEA)/85% C02; 120 bar; 35° C.; 3 mL/min; 370 nm), t$_R$=8.38 min; HPLC (Method A): t$_R$=8.55 min; (Method B) t$_R$=9.76 min.

Example 16

N-(4-(2-Methylmorpholino)pyridin-3-yl)-2-phenylimidazo[1,2-b]pyridazine-8-carboxamide

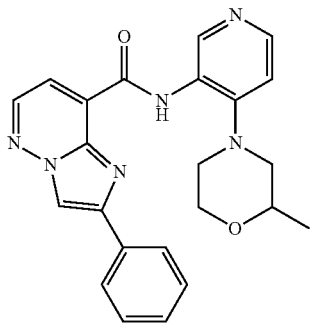 [SMILES: CC1CN(c2ccncc2NC(=O)c2ccnn3cc(-c4ccccc4)nc23)CCO1]

Racemic N-(4-(2-Methylmorpholino)pyridin-3-yl)-2-phenylimidazo[1,2-b]pyridazine-8-carboxamide was subjected to chiral separation (Column: ChiralPak AS-H, 30×250 mm, 5 μm; Mobile Phase: 15% EtOH (ww 0.1% DEA)/85% C02; 120 bar; 35° C.; 70 mL/min; 370 nm). Analytical data for Peak 2 (Enantiomer 2): $^1$H NMR (400 MHz, DMSO-d$_6$) δ 11.83 (s, 1H), 9.19 (d, J=3.3 Hz, 2H), 8.82 (d, J=4.8 Hz, 1H), 8.35 (d, J=5.5 Hz, 1H), 8.27-8.22 (m, 2H), 7.95 (d, J=4.8 Hz, 1H), 7.54 (t, J=7.4 Hz, 2H), 7.49-7.44 (m, 1H), 7.21 (d, J=5.3 Hz, 1H), 3.77-3.52 (m, 3H), 2.92-2.89 (m, 2H), 2.76-2.73 (m, 2H), 0.95 (d, J=6.3 Hz, 3H); LCMS (ESI) m/e 415.2 [(M+H)$^+$, calcd for C$_{23}$H$_{23}$N$_6$O$_2$ 415.2]; Analytical chiral HPLC (Column: ChiralPak AS-H, 4.6×250 mm, 5 μm; Mobile Phase: 15% EtOH (ww 0.1% DEA)/85% CO$_2$; 120 bar; 35° C.; 3 mL/min; 370 nm), t$_R$=10.10 min; HPLC (Method A): t$_R$=9.42 min; (Method B) t$_R$=9.89 min.

Example 17

(R)—N-(4-(3-Methylmorpholino)pyridin-3-yl)-2-phenylimidazo[1,2-b]pyridazine-8-carboxamide

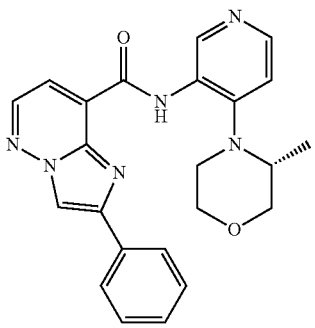 [SMILES: C[C@@H]1COCCN1c1ccncc1NC(=O)c1ccnn2cc(-c3ccccc3)nc12]

To a solution of 2-phenylimidazo[1,2-b]pyridazine-8-carboxylic acid (40 mg, 0.167 mmol), (R)-4-(3-methylmorpholino)pyridin-3-amine (64.6 mg, 0.334 mmol), and N,N-diisopropylethylamine (0.175 mL, 1.003 mmol) in DMF (1 mL) was added HATU (127 mg, 0.334 mmol). The reaction mixture was stirred at rt for 12 h. The mixture was concentrated and the residue was purified by reverse phase HPLC (Method A) to afford (R)—N-(4-(3-methylmorpholino)pyridin-3-yl)-2-phenylimidazo[1,2-b]pyridazine-8-carboxamide, 2 TFA (33 mg, 0.051 mmol, 30% yield) as a yellow solid: $^1$H NMR (400 MHz, DMSO-d$_6$) δ 11.86 (s, 1H), 9.28 (s, 1H), 9.17 (s, 1H), 8.81 (d, J=4.8 Hz, 1H), 8.38 (d, J=5.3 Hz, 1H), 8.27-8.21 (m, 2H), 7.94 (d, J=4.8 Hz, 1H), 7.57-7.50 (m, 2H), 7.50-7.42 (m, 1H), 7.30 (d, J=5.3 Hz, 1H), 3.66 (dd, J=11.2, 3.1 Hz, 1H), 3.61-3.50 (m, 2H), 3.50-3.40 (m, 1H), 3.27-3.17 (m, 2H), 2.73-2.64 (m, 1H), 0.98 (d, J=6.3 Hz, 3H); LCMS (ESI) m/e 415.1 [(M+H)+, calcd for C$_{23}$H$_{23}$N$_6$O$_2$ 415.2]; HPLC (Method A): t$_R$=12.77 min; (Method B) t$_R$=14.12 min.

Example 18

(S)—N-(4-(3-Methylmorpholino)pyridin-3-yl)-2-phenylimidazo[1,2-b]pyridazine-8-carboxamide

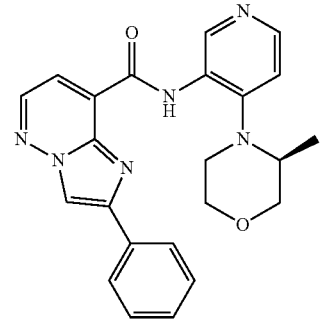 [SMILES: C[C@H]1COCCN1c1ccncc1NC(=O)c1ccnn2cc(-c3ccccc3)nc12]

To a solution of 2-phenylimidazo[1,2-b]pyridazine-8-carboxylic acid (40 mg, 0.167 mmol), (S)-4-(3-methylmorpholino)pyridin-3-amine (64.6 mg, 0.334 mmol), and N,N-diisopropylethylamine (0.175 mL, 1.003 mmol) in DMF (1 mL) was added HATU (127 mg, 0.334 mmol). The reaction mixture was stirred at rt for 2 h. The mixture was concentrated and the residue was purified by reverse phase HPLC (Method A) to afford (S)—N-(4-(3-methylmorpholino)pyridin-3-yl)-2-phenylimidazo[1,2-b]pyridazine-8-carboxamide, 2 TFA (36 mg, 0.055 mmol, 33% yield) as a yellow solid: $^1$H NMR (400 MHz, DMSO-d$_6$) δ 11.86 (s, 1H), 9.28 (s, 1H), 9.17 (s, 1H), 8.81 (d, J=4.8 Hz, 1H), 8.38 (d, J=5.5 Hz, 1H), 8.27-8.21 (m, 2H), 7.94 (d, J=4.5 Hz, 1H), 7.57-7.50 (m, 2H), 7.50-7.42 (m, 1H), 7.30 (d, J=5.5 Hz, 1H), 3.66 (dd, J=11.2, 3.1 Hz, 1H), 3.61-3.51 (m, 2H), 3.50-3.43 (m, 1H), 3.27-3.19 (m, 2H), 2.68 (td, J=7.8, 3.8 Hz, 1H), 0.98 (d, J=6.3 Hz, 3H); LCMS (ESI) m/e 415.2 [(M+H)$^+$, calcd for C$_{23}$H$_{23}$N$_6$O$_2$ 415.2]; HPLC (Method A): t$_R$=14.27 min; (Method B) t$_R$=14.37 min.

Example 19

N-(5-Methoxypyridin-3-yl)-2-phenylimidazo[1,2-b]pyridazine-8-carboxamide

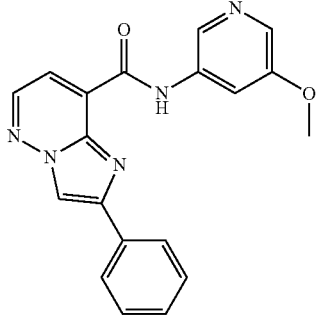 [SMILES: COc1cncc(NC(=O)c2ccnn3cc(-c4ccccc4)nc23)c1]

To a solution of 2-phenylimidazo[1,2-b]pyridazine-8-carboxylic acid (30 mg, 0.125 mmol) and 5-methoxypyridin-3-amine (31.1 mg, 0.251 mmol) in DMF (1 mL) was added N,N-diisopropylethylamine (0.131 mL, 0.752 mmol) and HATU (95 mg, 0.251 mmol).

The reaction mixture was stirred at rt for 12 h. The mixture was concentrated and the residue was purified by column chromatography on silica gel (5% methanol in methylene chloride; 12 g column) to afford N-(5-methoxypyridin-3-yl)-2-phenylimidazo[1,2-b]pyridazine-8-carboxamide (21 mg, 0.060 mmol, 48% yield) as a yellow solid: $^1$H NMR (400 MHz, DMSO-$d_6$) δ 12.13 (br. s., 1H), 9.15 (s, 1H), 8.79 (d, J=4.8 Hz, 1H), 8.54 (s, 1H), 8.23-8.16 (m, 3H), 8.06 (br. s., 1H), 7.86 (d, J=4.5 Hz, 1H), 7.57 (t, J=7.5 Hz, 2H), 7.48-7.42 (m, 1H), 3.92 (s, 3H); LCMS (ESI) m/e 346.1 [(M+H)$^+$, calcd for $C_{19}H_{16}N_5O_2$ 346.2]; HPLC (Method A): $t_R$=10.50 min; (Method B) $t_R$=10.52 min.

Example 20

N-(4-(4,4-Difluoropiperidin-1-yl)-6-fluoropyridin-3-yl)-2-phenylimidazo[1,2-b]pyridazine-8-carboxamide

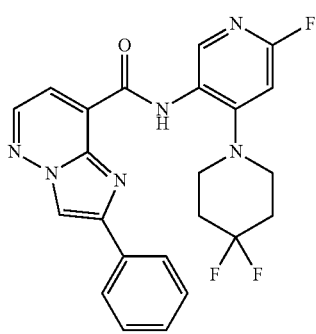 [SMILES: O=C(Nc1cnc(F)cc1N1CCC(F)(F)CC1)c1ccnn2cc(-c3ccccc3)nc12]

To a solution of 2-phenylimidazo[1,2-b]pyridazine-8-carboxylic acid (10 mg, 0.042 mmol), 4-(4,4-difluoropiperidin-1-yl)-6-fluoropyridin-3-amine (9.67 mg, 0.042 mmol) and N,N-diisopropylethylamine (0.029 mL, 0.167 mmol) in DMF (1 mL) was added HATU (19.07 mg, 0.050 mmol). The reaction mixture was stirred at rt for 12 h. The reaction mixture was transferred to a separatory funnel containing saturated aqueous NaHCO$_3$ solution (15 mL). The aqueous layer was extracted with ethyl acetate (3×15 mL). The combined organic layers were washed with brine (20 mL), dried over MgSO$_4$, filtered, and concentrated. The residue was purified by reverse phase HPLC (Method A) to afford N-(4-(4,4-difluoropiperidin-1-yl)-6-fluoropyridin-3-yl)-2-phenylimidazo[1,2-b]pyridazine-8-carboxamide, 2 TFA (8 mg, 0.012 mmol, 28% yield) as a yellow solid: $^1$H NMR (400 MHz, DMSO-$d_6$) δ 11.72 (s, 1H), 9.17 (s, 1H), 8.85-8.77 (m, 2H), 8.16 (d, J=7.0 Hz, 2H), 7.96 (d, J=4.8 Hz, 1H), 7.59-7.50 (m, 2H), 7.48-7.38 (m, 1H), 3.28 (br. s., 4H), 2.08-1.95 (m, 4H); LCMS (APCI) m/e 453.2 [(M+H)+, calcd for $C_{23}H_{20}F_3N_6O$ 453.2]; HPLC (Method A): $t_R$=16.05 min; (Method B) $t_R$=15.05 min.

Example 21

N-(6-Fluoro-4-morpholinopyridin-3-yl)-2-phenylimidazo[1,2-b]pyridazine-8-carboxamide

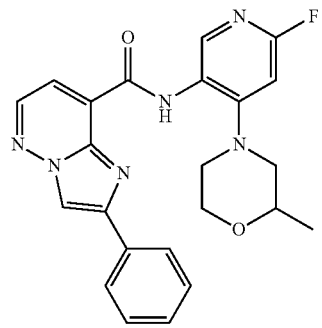 [SMILES: CC1CN(c2cc(F)ncc2NC(=O)c2ccnn3cc(-c4ccccc4)nc23)CCO1]

To a solution of 2-phenylimidazo[1,2-b]pyridazine-8-carboxylic acid (30 mg, 0.094 mmol) and 6-fluoro-4-(2-methylmorpholino)pyridin-3-amine (19.87 mg, 0.094 mmol) in DMF (0.7 mL) was added N,N-diisopropylethylamine (0.082 mL, 0.470 mmol) followed by HATU (42.9 mg, 0.113 mmol). The reaction mixture was stirred at rt for 2.5 h. The mixture was concentrated and the product was purified by reverse phase HPLC (Method A) to afford N-(6-fluoro-4-(2-methylmorpholino)pyridin-3-yl)-2-phenylimidazo[1,2-b]pyridazine-8-carboxamide, 2 TFA (18.5 mg, 0.028 mmol, 30% yield) as a yellow amorphous solid: $^1$H NMR (400 MHz, DMSO-$d_6$) δ 11.75 (s, 1H), 9.18 (s, 1H), 8.82 (d, J=4.8 Hz, 1H), 8.77 (s, 1H), 8.26-8.19 (m, 2H), 7.93 (d, J=4.8 Hz, 1H), 7.60-7.51 (m, 2H), 7.50-7.42 (m, 1H), 6.95 (s, 1H), 3.76-3.53 (m, 3H), 3.49-3.39 (m, 2H), 2.77 (td, J=11.7, 3.6 Hz, 1H), 2.64-2.55 (m, 1H), 0.94 (d, J=6.3 Hz, 3H); LC/MS (ESI) m/e 433.1 [(M+H)+, calcd for $C_{23}H_{22}FN_6O_2$ 433.2]; HPLC (Method A): $t_R$=15.85 min; (Method B) $t_R$=14.22 min.

Example 22

N-(6-Chloro-4-(4,4-difluoropiperidin-1-yl)pyridin-3-yl)-2-phenylimidazo[1,2-b]pyridazine-8-carboxamide

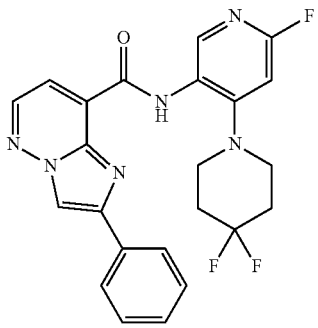 [SMILES: O=C(Nc1cnc(F)cc1N1CCC(F)(F)CC1)c1ccnn2cc(-c3ccccc3)nc12]

To a solution of 2-phenylimidazo[1,2-b]pyridazine-8-carboxylic acid (10 mg, 0.042 mmol), 6-chloro-4-(4,4-difluoropiperidin-1-yl)pyridin-3-amine (10.35 mg, 0.042 mmol) and N,N-diisopropylethylamine (0.029 mL, 0.167 mmol) in DMF (1 mL) was added HATU (19.07 mg, 0.050 mmol). The reaction mixture was stirred at rt for 12 h. The reaction mixture was transferred to a separatory funnel containing saturated aqueous NaHCO$_3$ solution (15 mL). The aqueous layer was extracted with ethyl acetate (3×15 mL). The combined organic layers were washed with brine (20 mL), dried over MgSO$_4$, filtered, and concentrated. The residue was purified by reverse phase HPLC (Method A) to afford N-(6-chloro-4-(4,4-difluoropiperidin-1-yl)pyridin-3-yl)-2-phenylimidazo[1,2-b]pyridazine-8-carboxamide, 2 TFA (10 mg, 0.014 mmol, 34% yield) as a yellow solid: $^1$H NMR (400 MHz, DMSO-d$_6$) δ 11.76 (s, 1H), 9.17 (s, 1H), 9.01 (s, 1H), 8.83 (d, J=4.5 Hz, 1H), 8.19-8.10 (m, 2H), 7.96 (d, J=4.8 Hz, 1H), 7.57-7.50 (m, 2H), 7.48-7.40 (m, 1H), 3.27 (br. s., 4H), 2.01 (t, J=13.8 Hz, 4H); LCMS (ESI) m/e 469.2 [(M+H)$^+$, calcd for C$_{23}$H$_{20}$F$_2$N$_6$OCl 469.2]; HPLC (Method A): t$_R$=17.06 min; (Method B) t$_R$=15.53 min.

Preparation of 2-(2-methoxyphenyl)imidazo[1,2-b]pyridazine-8-carboxylic acid

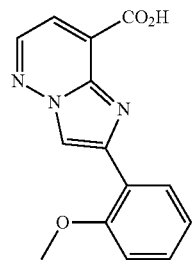 [SMILES: COc1ccccc1-c1cn2nccc(C(=O)O)c2n1]

Part A. Ethyl 6-chloro-2-(2-methoxyphenyl)imidazo[1,2-b]pyridazine-8-carboxylate

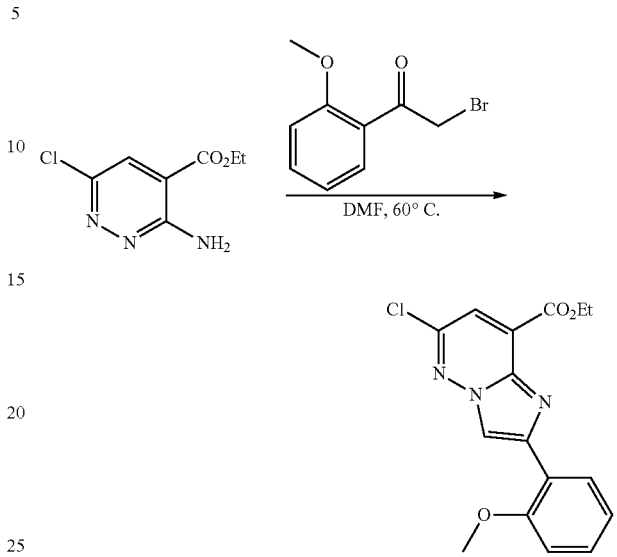

Ethyl 3-amino-6-chloropyridazine-4-carboxylate (200 mg, 0.992 mmol) was added to 2-bromo-1-(2-methoxyphenyl)ethanone (227 mg, 0.992 mmol) in DMF (3 mL). The solution was heated to 60° C. for 4 h. Additional 2-bromo-1-(2-methoxyphenyl)ethanone (227 mg, 0.992 mmol) was added and the reaction was heated to 60° C. for 12 h. The reaction mixture was partitioned between ether (30 mL) and saturated aq. NaHCO$_3$ solution (20 mL). The organic layer was washed with water (20 mL) and saturated aq. NaCl solution (20 mL), dried over MgSO$_4$, filtered and concentrated. The residue was purified by column chromatography on silica gel (5-20% ethyl acetate in hexanes; 25 g column) to afford ethyl 6-chloro-2-(2-methoxyphenyl)imidazo[1,2-b]pyridazine-8-carboxylate (200 mg, 0.603 mmol, 61% yield) as a yellow solid: $^1$H NMR (400 MHz, DMSO-d$_6$) δ 8.78 (s, 1H), 8.34 (dd, J=7.8, 1.8 Hz, 1H), 7.73 (s, 1H), 7.45-7.39 (m, 1H), 7.19 (d, J=7.8 Hz, 1H), 7.13 (td, J=7.5, 1.0 Hz, 1H), 4.49 (q, J=7.0 Hz, 2H), 4.01 (s, 3H), 1.42 (t, J=7.2 Hz, 3H).

Part B. Ethyl 2-(2-methoxyphenyl)imidazo[1,2-b]pyridazine-8-carboxylate

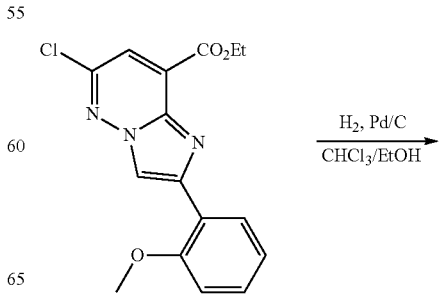

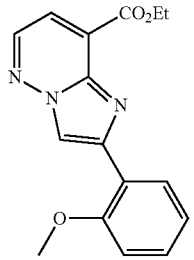

A mixture of ethyl 6-chloro-2-(2-methoxyphenyl)imidazo[1,2-b]pyridazine-8-carboxylate (150 mg, 0.452 mmol) and 10% palladium on carbon (72.2 mg, 0.034 mmol) in chloroform (2 mL) and ethanol (5 mL) was stirred under hydrogen in a 50 mL round bottom flask at atmospheric pressure for 14 h. The catalyst was removed by filtration through a pad of Celite. The filtrate was concentrated and the residue was purified by column chromatography on silica gel (20%→50% ethyl acetate in hexanes; 12 g column) to afford ethyl 2-(2-methoxyphenyl)imidazo[1,2-b]pyridazine-8-carboxylate (65 mg, 0.219 mmol, 48% yield) as a yellow solid: $^1$H NMR (400 MHz, DMSO-d$_6$) δ 8.75 (s, 1H), 8.66 (d, J=4.8 Hz, 1H), 8.37 (dd, J=7.8, 1.8 Hz, 1H), 7.64 (d, J=4.5 Hz, 1H), 7.44-7.38 (m, 1H), 7.19 (d, J=8.3 Hz, 1H), 7.13 (td, J=7.5, 1.0 Hz, 1H), 4.48 (q, J=7.0 Hz, 2H), 4.02 (s, 3H), 1.42 (t, J=7.0 Hz, 3H); LCMS (ESI) m/e 298.1 [(M+H)$^+$, calcd for C$_{16}$H$_{16}$N$_3$O$_3$ 298.1].

Part C. 2-(2-Methoxyphenyl)imidazo[1,2-b]pyridazine-8-carboxylic acid

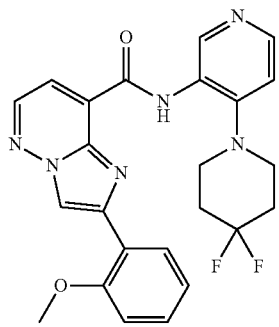

A mixture of ethyl 2-(2-methoxyphenyl)imidazo[1,2-b]pyridazine-8-carboxylate (65 mg, 0.219 mmol) and lithium hydroxide monohydrate (10.47 mg, 0.437 mmol) in THF (5 mL) and water (0.250 mL) was stirred at rt for 12 h. The reaction mixture was concentrated to afford 2-(2-methoxyphenyl)imidazo[1,2-b]pyridazine-8-carboxylic acid (60 mg, 0.223 mmol, 100% yield) as a yellow solid. The product was used directly in the next step. $^1$H NMR (400 MHz, METHANOL-d$_4$) δ 6.95 (s, 1H), 6.86 (d, J=4.3 Hz, 1H), 6.57 (d, J=7.0 Hz, 1H), 6.00 (d, J=4.0 Hz, 1H), 5.72 (t, J=7.9 Hz, 1H), 5.48 (d, J=8.3 Hz, 1H), 5.41 (t, J=7.3 Hz, 1H), 2.36 (s, 3H); LCMS (ESI) m/e 270.1 [(M+H)$^+$, calcd for C$_{14}$H$_{12}$N$_3$O$_3$ 270.1].

Example 23

N-(4-(4,4-Difluoropiperidin-1-yl)pyridin-3-yl)-2-(2-methoxyphenyl)imidazo[1,2-b]pyridazine-8-carboxamide

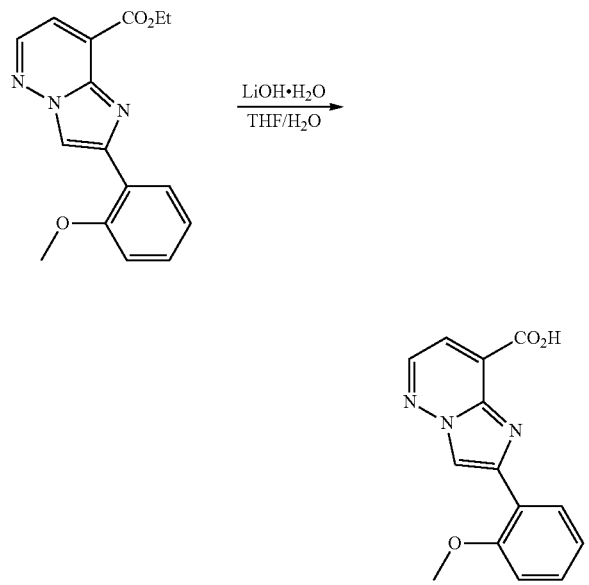 [SMILES: CCOC(=O)c1ccnn2cc(-c3ccccc3OC)nc12 ; "LiOH·H2O" ; COc1ccccc1-c1cn2nccc(C(=O)O)c2n1]

To a solution of 2-(2-methoxyphenyl)imidazo[1,2-b]pyridazine-8-carboxylic acid (15 mg, 0.056 mmol), 4-(4,4-difluoropiperidin-1-yl)pyridin-3-amine (23.76 mg, 0.111 mmol), and N,N-diisopropylethylamine (0.058 mL, 0.334 mmol) in DMF (1 mL) was added and HATU (42.4 mg, 0.111 mmol). The reaction mixture was stirred at rt for 12 h. The reaction mixture was transferred to a separatory funnel containing saturated aqueous NaHCO$_3$ solution (15 mL). The aqueous layer was extracted with ethyl acetate (3×15 mL). The combined organic layers were washed with brine (20 mL), dried over MgSO$_4$, filtered, and concentrated. The residue was purified by column chromatography on silica gel (20%→80% ethyl acetate in hexanes; 12 g column) to afford N-(4-(4,4-difluoropiperidin-1-yl)pyridin-3-yl)-2-(2-methoxyphenyl)imidazo[1,2-b]pyridazine-8-carboxamide (10 mg, 0.020 mmol, 37% yield) as a yellow solid: $^1$H NMR (400 MHz, CHLOROFORM-d) δ 11.98 (s, 1H), 9.40 (s, 1H), 8.74 (s, 1H), 8.58 (d, J=4.5 Hz, 1H), 8.41 (d, J=5.3 Hz, 1H), 8.38 (dd, J=7.9, 1.6 Hz, 1H), 8.01 (d, J=4.8 Hz, 1H), 7.45-7.40 (m, 1H), 7.13-7.06 (m, 2H), 7.06-7.02 (m, 1H), 4.06 (s, 3H), 3.27-3.21 (m, 4H), 2.10-1.96 (m, 4H); LCMS (ESI) m/e 465.2 [(M+H)$^+$, calcd for C$_{24}$H$_{23}$N$_6$O$_2$F$_2$ 465.2]; HPLC (Method A): t$_R$=10.45 min; (Method B) t$_R$=11.07 min.

Example 24

2-(2-Methoxyphenyl)-N-(4-(2-methylmorpholino)pyridin-3-yl)imidazo[1,2-b]pyridazine-8-carboxamide

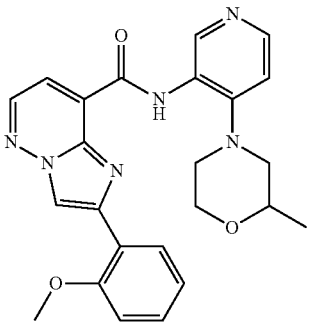 [SMILES: COc1ccccc1-c1cn2nccc(C(=O)Nc3cnccc3N3CCOC(C)C3)c2n1]

To a solution of 2-(2-methoxyphenyl)imidazo[1,2-b]pyridazine-8-carboxylic acid (15 mg, 0.056 mmol), 4-(2-methylmorpholino)pyridin-3-amine (21.53 mg, 0.111 mmol), and N,N-diisopropylethylamine (0.058 mL, 0.334 mmol) in DMF (1 mL) was added HATU (42.4 mg, 0.111 mmol). The reaction mixture was stirred at rt for 2 h. The reaction mixture was transferred to a separatory funnel containing saturated aqueous NaHCO$_3$ solution (15 mL). The aqueous layer was extracted with ethyl acetate (3×15 mL). The combined organic layers were washed with brine (20 mL), dried over MgSO$_4$, filtered, and concentrated. The residue was purified by column chromatography on silica gel (20%→80% ethyl acetate in hexanes; 12 g column) to afford 2-(2-methoxyphenyl)-N-(4-(2-methylmorpholino)pyridin-3-yl)imidazo[1,2-b]pyridazine-8-carboxamide (10 mg, 0.022 mmol, 40% yield) as a yellow solid: $^1$H NMR (400 MHz, CHLOROFORM-d) δ 12.03 (s, 1H), 9.40-9.31 (m, 1H), 8.75 (s, 1H), 8.56 (d, J=4.5 Hz, 1H), 8.51 (dd, J=7.8, 1.8 Hz, 1H), 8.41 (d, J=5.5 Hz, 1H), 7.99 (d, J=4.8 Hz, 1H), 7.44-7.39 (m, 1H), 7.10-7.04 (m, 2H), 7.02 (d, J=5.5 Hz, 1H), 4.07 (s, 3H), 3.82-3.76 (m, 1H), 3.76-3.70 (m, 2H), 3.34-3.27 (m, 2H), 2.87 (ddd, J=12.2, 10.2, 4.6 Hz, 1H), 2.64 (dd, J=11.8, 10.3 Hz, 1H), 1.04 (d, J=6.3 Hz, 3H); LCMS (ESI) m/e 445.1 [(M+H)$^+$, calcd for C$_{24}$H$_{25}$N$_6$O$_3$ 445.2]; HPLC (Method A): $t_R$=9.76 min; (Method B) $t_R$=10.19 min.

Preparation of 2-(4-(trifluoromethyl)phenyl)imidazo[1,2-b]pyridazine-8-carboxylic acid

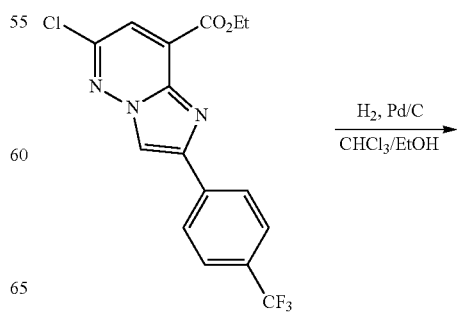

Part A. Ethyl 6-chloro-2-(4-(trifluoromethyl)phenyl)imidazo[1,2-b]pyridazine-8-carboxylate

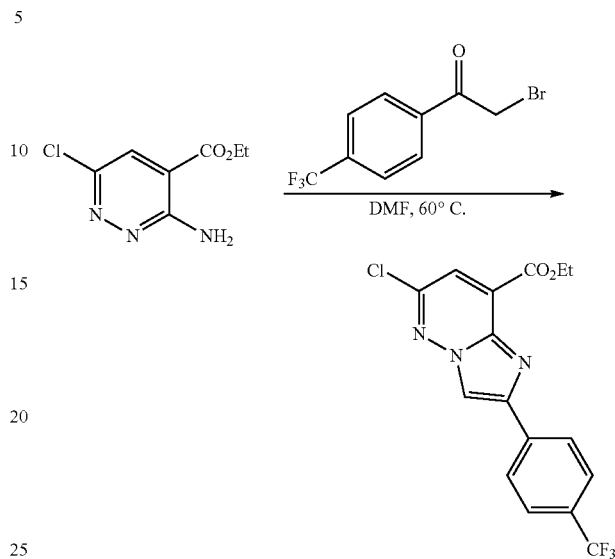

Ethyl 3-amino-6-chloropyridazine-4-carboxylate (270 mg, 1.339 mmol) was added to 2-bromo-1-(4-(trifluoromethyl)phenyl)ethanone (358 mg, 1.339 mmol) in DMF (6 mL). The solution was heated at 60° C. for 4 h. The resulting orange liquid was partitioned between ether (30 mL) and saturated aq. NaHCO$_3$ solution (20 mL). The organic layer was washed with water (20 mL) and saturated aq. NaCl solution (20 mL), dried over MgSO$_4$, filtered and concentrated. The residue was purified by column chromatography on silica gel (5-20% ethyl acetate in hexanes; 40 g column) to afford ethyl 6-chloro-2-(4-(trifluoromethyl)phenyl)imidazo[1,2-b]pyridazine-8-carboxylate (190 mg, 0.514 mmol, 38% yield) as a yellow solid: $^1$H NMR (400 MHz, DMSO-d$_6$) δ 9.23 (s, 1H), 8.31 (d, J=8.0 Hz, 2H), 7.89 (d, J=8.0 Hz, 2H), 7.79 (s, 1H), 4.49 (q, J=7.1 Hz, 2H), 1.42 (t, J=7.2 Hz, 3H); LCMS (ESI) m/e 370.0 [(M+H)$^+$, calcd for C$_{16}$H$_{12}$N$_3$O$_2$F$_3$Cl 370.1].

Part B. Ethyl 6-chloro-2-(4-(trifluoromethyl)phenyl)imidazo[1,2-b]pyridazine-8-carboxylate

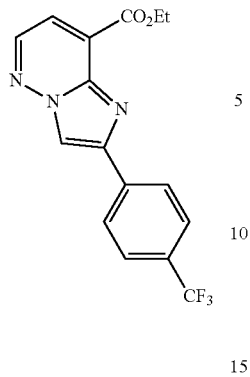

A mixture of ethyl 6-chloro-2-(4-(trifluoromethyl)phenyl)imidazo[1,2-b]pyridazine-8-carboxylate (190 mg, 0.514 mmol) and 10% palladium on carbon (82 mg, 0.039 mmol) in chloroform (2 mL) and ethanol (5 mL) was stirred under hydrogen in a 50 mL round bottom flask at atmospheric pressure for 6 h. The catalyst was removed by filtration through a pad of Celite. The filtrate was concentrated and the residue was purified by column chromatography on silica gel (20%→50% ethyl acetate in hexanes; 12 g column) to afford ethyl 2-(4-(trifluoromethyl)phenyl)imidazo[1,2-b]pyridazine-8-carboxylate (90 mg, 0.268 mmol, 52% yield) as a yellow solid: $^1$H NMR (400 MHz, DMSO-d$_6$) δ 9.21 (s, 1H), 8.71 (d, J=4.5 Hz, 1H), 8.33 (d, J=8.0 Hz, 2H), 7.88 (d, J=8.3 Hz, 2H), 7.69 (d, J=4.5 Hz, 1H), 4.48 (q, J=7.0 Hz, 2H), 1.42 (t, J=7.0 Hz, 3H); LCMS (ESI) m/e 336.1 [(M+H)$^+$, calcd for C$_{16}$H$_{13}$N$_3$O$_2$F$_3$ 336.1].

Part C. 2-(4-(Trifluoromethyl)phenyl)imidazo[1,2-b]pyridazine-8-carboxylic acid

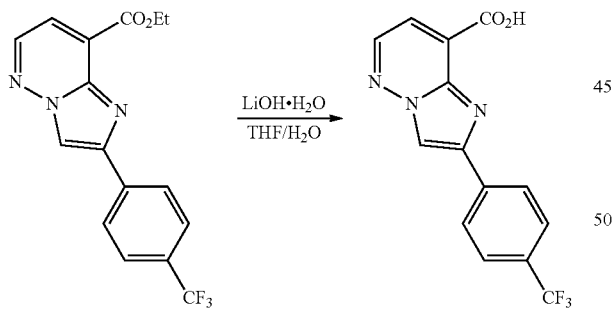

A mixture of ethyl 2-(4-(trifluoromethyl)phenyl)imidazo[1,2-b]pyridazine-8-carboxylate (90 mg, 0.268 mmol) and lithium hydroxide monohydrate (19.29 mg, 0.805 mmol) in THF (5 mL) and water was stirred at rt for 2 h. The reaction mixture was concentrated to afford 2-(4-(trifluoromethyl)phenyl)imidazo[1,2-b]pyridazine-8-carboxylic acid (80 mg, 0.260 mmol, 97% yield) as a yellow solid. The product was used directly in the next step. $^1$H NMR (400 MHz, DMSO-d$_6$) δ 9.04 (s, 1H), 8.62 (d, J=4.5 Hz, 1H), 8.35 (d, J=8.0 Hz, 2H), 7.80 (d, J=8.3 Hz, 2H), 7.58 (d, J=4.5 Hz, 1H); LCMS (ESI) m/e 308.1 [(M+H)$^+$, calcd for C$_{14}$H$_9$N$_3$O$_2$F$_3$ 308.1].

Example 25

N-(4-Morpholinopyridin-3-yl)-2-(4-(trifluoromethyl)phenyl)imidazo[1,2-b]pyridazine-8-carboxamide

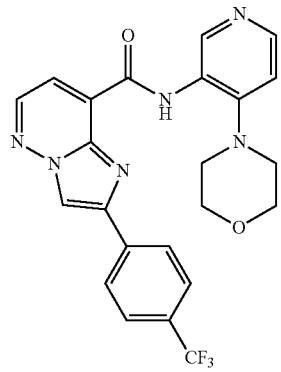 [SMILES: O=C(Nc1cnccc1N1CCOCC1)c1ccnn2cc(-c3ccc(C(F)(F)F)cc3)nc12]

To a suspension of 2-(4-(trifluoromethyl)phenyl)imidazo[1,2-b]pyridazine-8-carboxylic acid (30 mg, 0.059 mmol) in dichloromethane (4 mL) at 0° C. was added DMF (0.907 µl, 0.012 mmol) and oxalyl chloride (0.015 mL, 0.176 mmol). The mixture was stirred at room temperature for 1 hour. The mixture was concentrated and the residue was dried under vacuum for 1 hour. The residue was suspended in dichloromethane (4 mL) followed by the addition of triethylamine (0.033 mL, 0.234 mmol), DMAP (14.32 mg, 0.117 mmol) and 4-morpholinopyridin-3-amine (21.00 mg, 0.117 mmol) at 0° C. The reaction was stirred at room temperature for 4 h. The reaction mixture was transferred to a separatory funnel containing saturated aqueous NaHCO$_3$ solution (15 mL). The aqueous layer was extracted with CH$_2$Cl$_2$ (3×15 mL). The combined organic layers were washed with brine (15 mL), dried over MgSO$_4$, filtered, and concentrated. The residue was purified by reverse phase HPLC (Method A) followed by prep TLC (5% methanol in methylene chloride) to afford N-(4-morpholinopyridin-3-yl)-2-(4-(trifluoromethyl)phenyl)imidazo[1,2-b]pyridazine-8-carboxamide (7 mg, 0.014 mmol, 24% yield) as a yellow solid: LCMS (ESI) m/e 469.2 [(M+H)$^+$, calcd for C$_{23}$H$_{20}$N$_6$O$_2$F$_3$ 469.2]; HPLC retention time (Method A): t$_R$=11.23 min; HPLC (Method B): t$_R$=10.73 min.

Example 26

N-(4-(2-Methylmorpholino)pyridin-3-yl)-2-(4-(trifluoromethyl)phenyl)imidazo[1,2-b]pyridazine-8-carboxamide

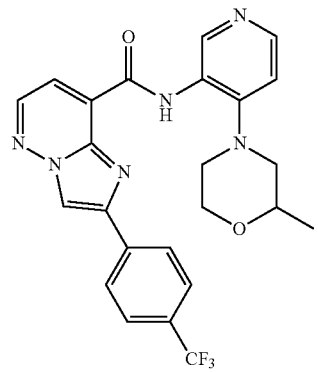 [SMILES: CC1CN(c2ccncc2NC(=O)c2ccnn3cc(-c4ccc(C(F)(F)F)cc4)nc23)CCO1]

To a suspension of 2-(4-(trifluoromethyl)phenyl)imidazo[1,2-b]pyridazine-8-carboxylic acid (50 mg, 0.098 mmol) in dichloromethane (4 mL) at 0° C. was added DMF (1.512 μl, 0.020 mmol) and oxalyl chloride (0.026 mL, 0.293 mmol). The reaction mixture was stirred at room temperature for 1 h. The solvent was evaporated and the residue was dried under vacuum for 1 h. The residue was suspended in dichloromethane (4 mL) followed by the addition of triethylamine (0.054 mL, 0.391 mmol), DMAP (23.86 mg, 0.195 mmol), and 4-(2-methylmorpholino)pyridin-3-amine (37.7 mg, 0.195 mmol) at 0° C. The cooling bath was removed and the reaction mixture was stirred at room temperature for 4 h. The reaction mixture was transferred to a separatory funnel containing saturated aqueous NaHCO₃ solution (15 mL). The aqueous layer was extracted with CH₂Cl₂ (3×15 mL). The combined organic layers were washed with brine (15 mL), dried over MgSO₄, filtered, and concentrated. The residue was purified by reverse phase HPLC (Method A) followed by prep TLC (5% methanol in methylene chloride) to afford N-(4-(2-methylmorpholino)pyridin-3-yl)-2-(4-(trifluoromethyl)phenyl)imidazo[1,2-b]pyridazine-8-carboxamide (15 mg, 0.030 mmol, 30% yield) as a yellow solid: $^1$H NMR (400 MHz, DMSO-$d_6$) δ 11.73 (s, 1H), 9.36 (s, 1H), 9.04 (br. s., 1H), 8.88 (d, J=4.5 Hz, 1H), 8.50 (br. s., 1H), 8.46-8.41 (m, J=8.0 Hz, 2H), 7.97 (d, J=4.5 Hz, 1H), 7.94-7.90 (m, J=8.3 Hz, 2H), 7.59 (br. s., 1H), 3.95 (t, J=13.8 Hz, 2H), 3.74-3.62 (m, 2H), 3.56 (t, J=10.8 Hz, 1H), 3.14 (t, J=10.9 Hz, 1H), 2.92-2.85 (m, 1H), 0.94 (d, J=6.3 Hz, 3H); LCMS (ESI) m/e 483.1 [(M+H)⁺, calcd for $C_{24}H_{22}N_6O_2F_3$ 483.2]; HPLC (Method A): $t_R$=10.63 min; (Method B) $t_R$=10.63 min.

Preparation of imidazo[1,2-b]pyridazine-8-carboxylic acid

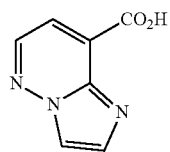

Part A. Ethyl 6-chloroimidazo[1,2-b]pyridazine-8-carboxylate

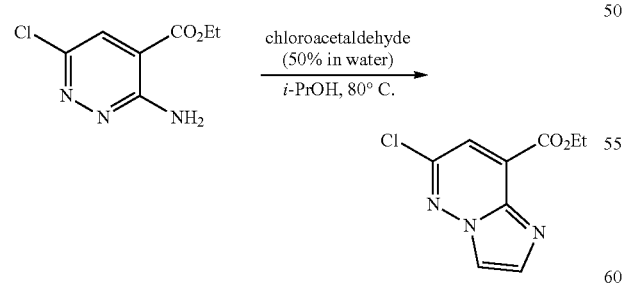

Chloroacetaldehyde (50% in H₂O) (5.04 mL, 39.7 mmol) was added to ethyl 3-amino-6-chloropyridazine-4-carboxylate (1.00 g, 4.96 mmol) in isopropanol (20 mL). The solution was heated at 80° C. for 4 h. The reaction mixture was concentrated and the resulting orange liquid was partitioned between ether (30 mL) and saturated aq. NaHCO₃ solution (20 mL). The organic layer was washed with water (20 mL) and saturated aq. NaCl solution (20 mL), dried over MgSO₄, filtered, and concentrated. The residue was purified by column chromatography on silica gel (60%→80% ethyl acetate in hexanes; 25 g column) to afford ethyl 6-chloroimidazo[1,2-b]pyridazine-8-carboxylate (750 mg, 3.32 mmol, 67% yield) as a green solid: $^1$H NMR (400 MHz, METHANOL-$d_4$) δ 8.23 (d, J=1.5 Hz, 1H), 7.88 (d, J=1.3 Hz, 1H), 7.73 (s, 1H), 4.52 (q, J=7.0 Hz, 2H), 1.45 (t, J=7.2 Hz, 3H); LCMS (ESI) m/e 226.0 [(M+H)⁺, calcd for $C_9H_9N_3O_2Cl$ 226.0].

Part B. Imidazo[1,2-b]pyridazine-8-carboxylic acid

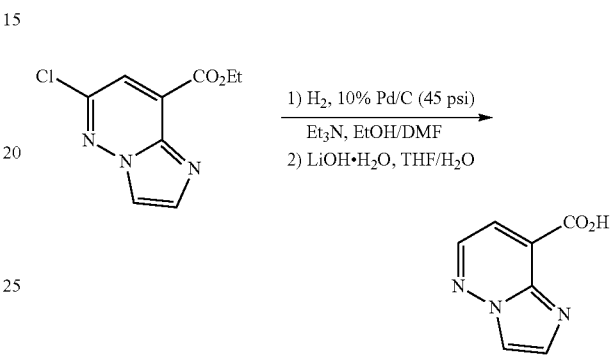

A mixture of ethyl imidazo[1,2-b]pyridazine-8-carboxylate (165 mg, 0.733 mmol), 10% palladium on carbon (130 mg, 0.122 mmol), and triethylamine (0.169 mL, 1.22 mmol) in EtOH (8 mL) and DMF (8 mL) was placed under a hydrogen atmosphere at 45 psi in a Parr shaker for 4 h. The catalyst was removed by filtration through a pad of Celite and the filtrate was concentrated. The residue was purified by column chromatography on silica gel (10% methanol in dichloromethane; 25 g column) to afford ethyl 3-aminoimidazo[1,2-b]pyridazine-8-carboxylate (100 mg, 80% yield). A mixture of ethyl imidazo[1,2-b]pyridazine-8-carboxylate (100 mg, 0.485 mmol) and lithium hydroxide monohydrate (81 mg, 1.940 mmol) in water (0.2 mL) and THF (5 mL) was stirred at room temperature for 2 h. The solvent was then concentrated to afford imidazo[1,2-b]pyridazine-8-carboxylic acid (60 mg, 76% yield). The crude product was used directly in the next step. $^1$H NMR (400 MHz, DMSO-$d_6$) δ 8.60 (d, J=4.8 Hz, 1H), 8.33 (d, J=1.3 Hz, 1H), 7.76 (d, J=1.3 Hz, 1H), 7.52 (d, J=4.3 Hz, 1H); LCMS (ESI) m/e 164.0 [(M)⁺, calcd for $C_7H_6N_3O_2$ 164.1].

Example 27

N-(4-(Piperidin-1-yl)pyridin-3-yl)imidazo[1,2-b]pyridazine-8-carboxamide

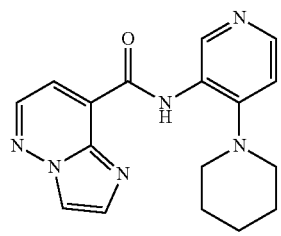 [SMILES: O=C(Nc1cnccc1N1CCCCC1)c1ccnn2ccnc12]

To a solution of imidazo[1,2-b]pyridazine-8-carboxylic acid, TFA (40 mg, 0.144 mmol) and 4-(piperidin-1-yl)pyridin-3-amine, 2 HCl (72.2 mg, 0.289 mmol) in DMF (1 mL) was added N,N-diisopropylethylamine (0.151 mL, 0.866 mmol) and HATU (110 mg, 0.289 mmol). The reaction mixture was stirred at rt for 4 h. The reaction mixture was transferred to a separatory funnel containing saturated aqueous NaHCO$_3$ solution (5 mL). The aqueous layer was extracted with ethyl acetate (3×10 mL). The combined organic layers were washed with brine (10 mL), dried over MgSO$_4$, filtered, and concentrated. The residue was purified by reverse phase HPLC (Method A) to afford N-(4-(piperidin-1-yl)pyridin-3-yl)imidazo[1,2-b]pyridazine-8-carboxamide, 2 TFA (18 mg, 0.029 mmol, 20% yield) as a red solid: $^1$H NMR (400 MHz, DMSO-d$_6$) δ 11.90 (s, 1H), 9.15 (s, 1H), 8.86 (d, J=4.5 Hz, 1H), 8.61 (d, J=1.3 Hz, 1H), 8.43 (d, J=6.5 Hz, 1H), 8.09-8.04 (m, 1H), 7.94 (d, J=4.5 Hz, 1H), 7.47 (d, J=6.5 Hz, 1H), 3.41 (d, J=5.3 Hz, 4H), 3.22-3.11 (m, 2H), 1.74-1.68 (m, 4H); LCMS (ESI) m/e 323.2 [(M+H)$^+$, calcd for C$_{17}$H$_{19}$N$_6$O 323.2]; HPLC (Method A): t$_R$=7.54 min; (Method B) t$_R$=7.83 min.

Example 28

N-(4-(4,4-Difluoropiperidin-1-yl)pyridin-3-yl)imidazo[1,2-b]pyridazine-8-carboxamide

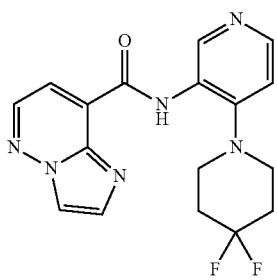 [SMILES: O=C(Nc1cnccc1N1CCC(F)(F)CC1)c1ccnn2ccnc12]

To a solution of imidazo[1,2-b]pyridazine-8-carboxylic acid, TFA (30 mg, 0.108 mmol) and 4-(4,4-difluoropiperidin-1-yl)pyridin-3-amine (46.2 mg, 0.216 mmol) in DMF (1 mL) was added N,N-diisopropylethylamine (0.113 mL, 0.649 mmol) and HATU (82 mg, 0.216 mmol). The reaction mixture was stirred at rt for 4 h. The reaction mixture was transferred to a separatory funnel containing saturated aqueous NaHCO$_3$ solution (5 mL). The aqueous layer was extracted with ethyl acetate (3×10 mL). The combined organic layers were washed with brine (10 mL), dried over MgSO$_4$, filtered, and concentrated. The residue was purified by reverse phase HPLC (Method A) to afford N-(4-(4,4-difluoropiperidin-1-yl)pyridin-3-yl)imidazo[1,2-b]pyridazine-8-carboxamide, 2 TFA (17 mg, 0.029 mmol, 27% yield) as a yellow solid: $^1$H NMR (400 MHz, DMSO-d$_6$) δ 12.02 (s, 1H), 9.32 (s, 1H), 8.87 (d, J=4.8 Hz, 1H), 8.62 (d, J=1.3 Hz, 1H), 8.53 (dd, J=6.5, 0.8 Hz, 1H), 8.03 (d, J=1.3 Hz, 1H), 7.97 (d, J=4.5 Hz, 1H), 7.62 (d, J=6.5 Hz, 1H), 3.53 (t, J=5.5 Hz, 4H), 2.31-2.19 (m, 4H); LCMS (ESI) m/e 359.2 [(M+H)+, calcd for C$_{17}$H$_{17}$N$_6$OF$_2$ 359.1]; HPLC (Method A): t$_R$=7.90 min; (Method B) t$_R$=8.48 min.

Example 29

N-(4-(2-Methylmorpholino)pyridin-3-yl)imidazo[1,2-b]pyridazine-8-carboxamide

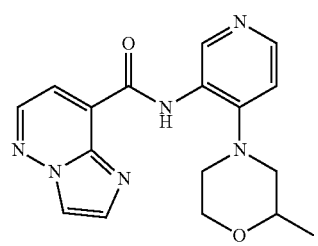 [SMILES: CC1CN(c2ccncc2NC(=O)c2ccnn3ccnc23)CCO1]

To a solution of imidazo[1,2-b]pyridazine-8-carboxylic acid, TFA (30 mg, 0.108 mmol) and 4-(2-methylmorpholino)pyridin-3-amine (41.8 mg, 0.216 mmol) in DMF (1 mL) was added N,N-diisopropylethylamine (0.113 mL, 0.649 mmol) and HATU (82 mg, 0.216 mmol). The reaction mixture was stirred at rt for 4 h. The reaction mixture was transferred to a separatory funnel containing saturated aqueous NaHCO$_3$ solution (5 mL). The aqueous layer was extracted with ethyl acetate (3×10 mL). The combined organic layers were washed with brine (10 mL), dried over MgSO$_4$, filtered, and concentrated. The residue was purified by reverse phase HPLC (Method A) to afford N-(4-(2-methylmorpholino)pyridin-3-yl)imidazo[1,2-b]pyridazine-8-carboxamide, 2 TFA (15 mg, 0.025 mmol, 23% yield) as a red solid: $^1$H NMR (400 MHz, CHLOROFORM-d) δ 12.20 (br. s., 1H), 9.69 (s, 1H), 8.65 (d, J=4.5 Hz, 1H), 8.55 (d, J=6.5 Hz, 1H), 8.19 (d, J=1.0 Hz, 1H), 8.02 (d, J=4.5 Hz, 1H), 7.89 (d, J=1.0 Hz, 1H), 7.32 (d, J=6.8 Hz, 1H), 4.17-3.96 (m, 2H), 3.62 (d, J=12.3 Hz, 2H), 3.18 (td, J=11.9, 3.3 Hz, 1H), 2.94-2.78 (m, 2H), 1.22 (d, J=6.3 Hz, 3H); LCMS (ESI) m/e 339.2 [(M+H)+, calcd for C$_{17}$H$_{19}$N$_6$O$_2$ 339.2]; HPLC (Method A): t$_R$=6.71 min; (Method B) t$_R$=7.21 min.

Preparation of 2-cyclopropylimidazo[1,2-b]pyridazine-8-carboxylic acid

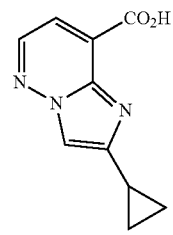

Part A. Ethyl 2-cyclopropylimidazo[1,2-b]pyridazine-8-carboxylate

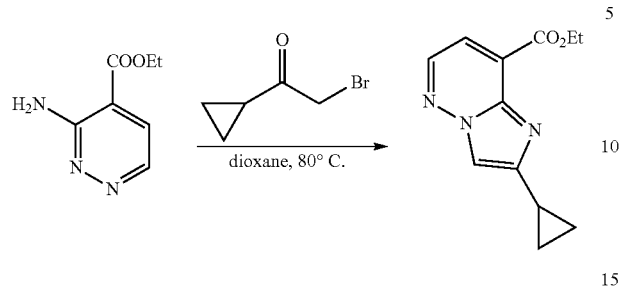

A mixture of ethyl 3-aminopyridazine-4-carboxylate (300 mg, 1.795 mmol) and 2-bromo-1-cyclopropylethanone (585 mg, 3.59 mmol) in dioxane (6 mL) was heated at 80° C. for 1 h. The mixture was cooled to room temperature and was transferred to a separatory funnel containing saturated aqueous NaHCO$_3$ solution (10 mL). The aqueous layer was extracted with dichloromethane (3×20 mL). The combined organic layers were washed with brine (10 mL), dried over MgSO$_4$, filtered, and concentrated. The residue was purified by column chromatography on silica gel (10%→40% ethyl acetate in hexanes; 12 g column) to afford ethyl 2-cyclopropylimidazo[1,2-b]pyridazine-8-carboxylate (112 mg, 0.484 mmol, 27% yield) as a dark green oil: $^1$H NMR (400 MHz, CDCl$_3$) δ 8.35 (d, J=4.8 Hz, 1H), 7.79 (s, 1H), 7.52 (d, J=4.8 Hz, 1H), 4.54 (q, J=7.0 Hz, 2H), 2.22 (tt, J=8.4, 5.1 Hz, 1H), 1.48 (t, J=7.2 Hz, 3H), 1.12-1.04 (m, 2H), 1.02-0.96 (m, 2H); LC/MS (ESI) m/e 232.1 [(M+H)$^+$, calcd for C$_{12}$H$_{14}$N$_3$O$_2$ 232.1].

Part B. 2-Cyclopropylimidazo[1,2-b]pyridazine-8-carboxylic acid

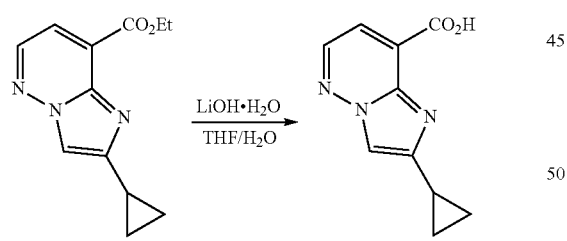

A mixture of ethyl 2-cyclopropylimidazo[1,2-b]pyridazine-8-carboxylate (110 mg, 0.476 mmol) and lithium hydroxide monohydrate (59.9 mg, 1.427 mmol) in water (0.150 mL) and THF (3 mL) was stirred at room temperature for 2 h. The solvent was concentrated to afford 2-cyclopropylimidazo[1,2-b]pyridazine-8-carboxylic acid (112 mg, 74% yield). The product was used without further purification in the next step. $^1$H NMR (400 MHz, DMSO-d$_6$) δ 8.79 (d, J=4.8 Hz, 1H), 8.41 (s, 1H), 7.80 (d, J=4.0 Hz, 1H), 2.27-2.18 (m, 1H), 1.14-1.06 (m, 2H), 0.98-0.92 (m, 2H); LC/MS (ESI) m/e 204.2 [(M+H)$^+$, calcd for C$_{10}$H$_{19}$N$_3$O$_2$ 204.1].

Example 30

2-Cyclopropyl-N-(4-(4-fluorophenyl)pyridin-3-yl)imidazo[1,2-b]pyridazine-8-carboxamide

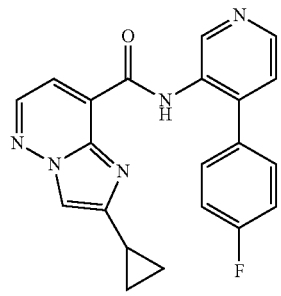 [SMILES: O=C(Nc1cnccc1-c1ccc(F)cc1)c1ccnn2cc(C3CC3)nc12]

To a solution of 2-cyclopropylimidazo[1,2-b]pyridazine-8-carboxylic acid, TFA (35 mg, 0.110 mmol) and 4-(4-fluorophenyl)pyridin-3-amine (29.1 mg, 0.154 mmol) in DMF (1 mL) was added N,N-diisopropylethylamine (0.096 mL, 0.552 mmol) followed by HATU (58.7 mg, 0.154 mmol). The reaction mixture was stirred at rt for 3 h. The reaction mixture was concentrated. The product was purified by reverse phase HPLC (Method A) to afford 2-cyclopropyl-N-(4-(4-fluorophenyl)pyridin-3-yl)imidazo[1,2-b]pyridazine-8-carboxamide, 2 TFA (43.3 mg, 0.071 mmol, 65% yield) as a yellow amorphous solid: $^1$H NMR (400 MHz, DMSO-d$_6$) δ 11.74 (s, 1H), 9.48 (s, 1H), 8.70 (d, J=4.8 Hz, 1H), 8.59 (d, J=5.3 Hz, 1H), 8.26 (s, 1H), 7.83 (d, J=4.8 Hz, 1H), 7.73-7.67 (m, 2H), 7.60 (d, J=5.3 Hz, 1H), 7.41-7.33 (m, 2H), 1.79 (tt, J=8.3, 5.0 Hz, 1H), 0.92-0.84 (m, 2H), 0.54-0.46 (m, 2H); LC/MS (ESI) m/e 374.1 [(M+H)$^+$, calcd for C$_{21}$H$_{17}$FN$_5$O 374.1]; HPLC (Method A): t$_R$=10.03 min; (Method B) t$_R$=10.50 min.

Example 31

2-Cyclopropyl-N-(4-(4,4-difluoropiperidin-1-yl)pyridin-3-yl)imidazo[1,2-b]pyridazine-8-carboxamide

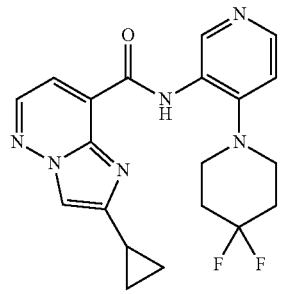 [SMILES: O=C(Nc1cnccc1N1CCC(F)(F)CC1)c1ccnn2cc(C3CC3)nc12]

To a solution of 2-cyclopropylimidazo[1,2-b]pyridazine-8-carboxylic acid, TFA (35 mg, 0.110 mmol) and 4-(4,4-difluoropiperidin-1-yl)pyridin-3-amine (32.9 mg, 0.154 mmol) in DMF (1 mL) was added N,N-diisopropylethylamine (0.096 mL, 0.552 mmol) followed by HATU (58.7 mg, 0.154 mmol). The reaction mixture was stirred at rt for 3 h. The reaction mixture was concentrated. The product was purified by reverse phase HPLC (Method A) to afford 2-cyclopropyl-N-(4-(4,4-difluoropiperidin-1-yl)pyridin-3-yl)imidazo[1,2-b]pyridazine-8-carboxamide, 2 TFA (55.7 mg, 0.088 mmol, 80% yield) as a yellow amorphous solid: $^1$H NMR (400 MHz, DMSO-$d_6$) δ 11.78 (s, 1H), 9.22 (s, 1H), 8.76 (d, J=4.8 Hz, 1H), 8.53 (dd, J=6.8, 1.0 Hz, 1H), 8.40 (s, 1H), 7.89 (d, J=4.5 Hz, 1H), 7.63 (d, J=6.5 Hz, 1H), 3.60 (t, J=5.4 Hz, 4H), 2.31-2.13 (m, 5H), 1.12-1.05 (m, 2H), 0.98-0.91 (m, 2H); LC/MS (ESI) m/e 399.1 [(M+H)$^+$, calcd for $C_{20}H_{21}F_2N_6O$ 399.2]; HPLC (Method A): $t_R$=9.36 min; (Method B) $t_R$=9.99 min.

Example 32

2-Cyclopropyl-N-(4-(2-methylmorpholino)pyridin-3-yl)imidazo[1,2-b]pyridazine-8-carboxamide

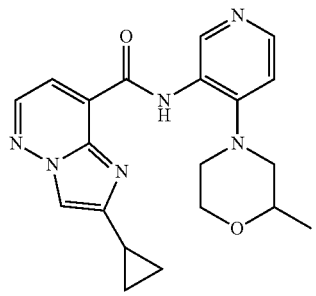 [SMILES: CC1CN(c2ccncc2NC(=O)c2ccnn3cc(C4CC4)nc23)CCO1]

To a solution of 2-cyclopropylimidazo[1,2-b]pyridazine-8-carboxylic acid, TFA (35 mg, 0.110 mmol) and 4-(2-methylmorpholino)pyridin-3-amine (29.9 mg, 0.154 mmol) in DMF (1 mL) was added N,N-diisopropylethylamine (0.096 mL, 0.552 mmol) followed by HATU (58.7 mg, 0.154 mmol). The reaction mixture was stirred at rt for 1.5 h. The reaction mixture was concentrated. The product was purified by reverse phase HPLC (Method A) to afford 2-cyclopropyl-N-(4-(2-methylmorpholino)pyridin-3-yl)imidazo[1,2-b]pyridazine-8-carboxamide, 2 TFA (62.6 mg, 0.099 mmol, 90% yield) as a yellow amorphous solid: $^1$H NMR (400 MHz, DMSO-$d_6$) δ 11.70 (s, 1H), 9.09 (s, 1H), 8.75 (d, J=4.8 Hz, 1H), 8.48 (dd, J=6.9, 0.9 Hz, 1H), 8.41 (s, 1H), 7.85 (d, J=4.8 Hz, 1H), 7.55 (d, J=7.0 Hz, 1H), 3.93-3.80 (m, 4H), 3.79-3.71 (m, 1H), 3.23-3.14 (m, 1H), 2.89 (dd, J=12.7, 10.2 Hz, 1H), 2.25-2.16 (m, 1H), 1.14-1.07 (m, 2H), 1.05 (d, J=6.3 Hz, 3H), 1.00-0.94 (m, 2H); LC/MS (ESI) m/e 379.1 [(M+H)$^+$, calcd for $C_{20}H_{23}N_6O_2$ 379.2]; HPLC (Method A): $t_R$=8.45 min; (Method B) $t_R$=8.74 min.

Preparation of 2-(cyclohex-1-en-1-yl)imidazo[1,2-b]pyridazine-8-carboxylic acid

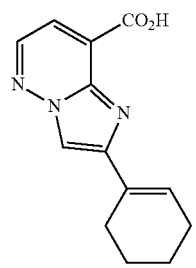 [SMILES: O=C(O)c1ccnn2cc(C3=CCCCC3)nc12]

Part A. Ethyl 2-(cyclohex-1-en-1-yl)imidazo[1,2-b]pyridazine-8-carboxylate

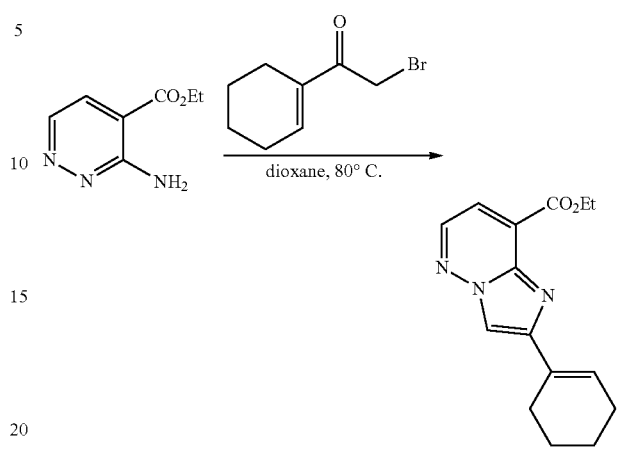

A mixture of ethyl 3-aminopyridazine-4-carboxylate (175 mg, 1.047 mmol) and 2-bromo-1-(cyclohex-1-en-1-yl)ethanone (319 mg, 1.570 mmol) in dioxane (3.5 mL) was heated at 80° C. for 1 h. The mixture was cooled to room temperature and was transferred to a separatory funnel containing saturated aqueous NaHCO$_3$ solution (10 mL). The aqueous layer was extracted with dichloromethane (3×20 mL). The combined organic layers were washed with brine (10 mL), dried over MgSO$_4$, filtered, and concentrated. The residue was purified by column chromatography on silica gel (10%→30% ethyl acetate in hexanes; 12 g column) to afford ethyl 2-(cyclohex-1-en-1-yl)imidazo[1,2-b]pyridazine-8-carboxylate (82 mg, 0.302 mmol, 29% yield) as a yellow oil: $^1$H NMR (400 MHz, CDCl$_3$) δ 8.36 (d, J=4.8 Hz, 1H), 7.97 (s, 1H), 7.56 (d, J=4.8 Hz, 1H), 6.96 (dt, J=4.0, 2.2 Hz, 1H), 4.55 (q, J=7.1 Hz, 2H), 2.54-2.45 (m, 2H), 2.35-2.25 (m, 2H), 1.89-1.79 (m, 2H), 1.77-1.68 (m, 2H), 1.51 (t, J=7.0 Hz, 3H); LC/MS (ESI) m/e 272.1 [(M+H)$^+$, calcd for $C_{15}H_{18}N_3O_2$ 272.1].

Part B. 2-(Cyclohex-1-en-1-yl)imidazo[1,2-b]pyridazine-8-carboxylic acid

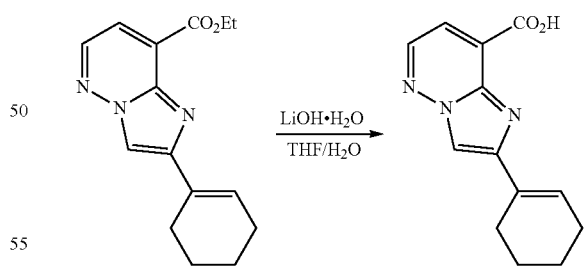

A mixture of ethyl 2-(cyclohex-1-en-1-yl)imidazo[1,2-b]pyridazine-8-carboxylate (72 mg, 0.265 mmol), lithium hydroxide monohydrate (19.07 mg, 0.796 mmol) in THF (3 mL) and water (0.15 mL) was stirred at room temperature for 2 h. Additional lithium hydroxide monohydrate (19 mg) in water (0.15 mL) was added and the reaction mixture was heated at 50° C. for 2 h. The reaction mixture was concentrated. The product was purified by reverse phase HPLC (Method A) to afford 2-(cyclohex-1-en-1-yl)imidazo[1,2-b]pyridazine-8-carboxylic acid, TFA (79.6 mg, 0.223 mmol, 84% yield) as a yellow amorphous solid: ¹H NMR (400 MHz, DMSO-$d_6$) δ 8.67 (d, J=4.5 Hz, 1H), 8.52 (s, 1H), 7.66 (d, J=4.5 Hz, 1H), 6.78 (dt, J=3.6, 2.1 Hz, 1H), 2.44 (d, J=1.8 Hz, 2H), 2.28-2.21 (m, 2H), 1.79-1.72 (m, 2H), 1.70-1.62 (m, J=5.7, 5.7, 3.6 Hz, 2H); LC/MS (ESI) m/e 244.1 [(M+H)⁺, calcd for $C_{13}H_{14}N_3O_2$ 244.1].

Example 33

2-(Cyclohex-1-en-1-yl)-N-(4-(4-fluorophenyl)pyridin-3-yl)imidazo[1,2-b]pyridazine-8-carboxamide

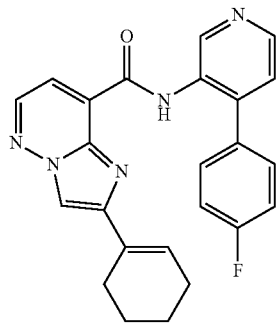 [SMILES: O=C(Nc1cnccc1-c1ccc(F)cc1)c1ccnn2cc(C3=CCCCC3)nc12]

To a solution of 2-(cyclohex-1-en-1-yl)imidazo[1,2-b]pyridazine-8-carboxylic acid, TFA (20 mg, 0.056 mmol) and 4-(4-fluorophenyl)pyridin-3-amine (10.54 mg, 0.056 mmol) in DMF (1 mL) was added N,N-diisopropylethylamine (0.049 mL, 0.280 mmol) followed by HATU (25.5 mg, 0.067 mmol). The reaction mixture was stirred at rt for 2.5 h. The mixture was concentrated. The product was purified by reverse phase HPLC (Method A) to afford 2-(cyclohex-1-en-1-yl)-N-(4-(4-fluorophenyl)pyridin-3-yl)imidazo[1,2-b]pyridazine-8-carboxamide, 2 TFA (6.4 mg, 9.68 µmol, 17% yield) as a yellow amorphous solid: ¹H NMR (500 MHz, DMSO-$d_6$) δ 11.92 (s, 1H), 9.43 (s, 1H), 8.70 (d, J=4.7 Hz, 1H), 8.55 (d, J=5.0 Hz, 1H), 8.41 (s, 1H), 7.87 (d, J=4.7 Hz, 1H), 7.75-7.70 (m, 2H), 7.55 (d, J=5.0 Hz, 1H), 7.29 (t, J=8.9 Hz, 2H), 5.83 (t, J=3.9 Hz, 1H), 5.76 (s, 1H), 2.15 (br. s., 2H), 2.08 (br. s., 2H), 1.69-1.63 (m, 2H), 1.62-1.56 (m, 2H); LC/MS (ESI) m/e 414.1 [(M+H)⁺, calcd for $C_{24}H_{21}FN_5O$ 414.2]; HPLC (Method A): $t_R$=11.72 min; (Method B) $t_R$=11.88 min.

Example 34

2-(Cyclohex-1-en-1-yl)-N-(4-(4,4-difluoropiperidin-1-yl)pyridin-3-yl)imidazo[1,2-b]pyridazine-8-carboxamide

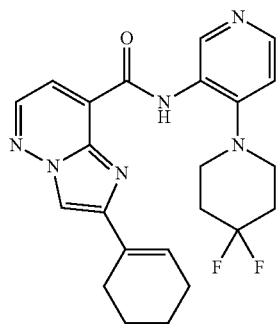 [SMILES: O=C(Nc1cnccc1N1CCC(F)(F)CC1)c1ccnn2cc(C3=CCCCC3)nc12]

To a solution of 2-(cyclohex-1-en-1-yl)imidazo[1,2-b]pyridazine-8-carboxylic acid, TFA (40 mg, 0.112 mmol) and 4-(4,4-difluoropiperidin-1-yl)pyridin-3-amine (28.6 mg, 0.134 mmol) in DMF (1 mL) was added N,N-diisopropylethylamine (0.098 mL, 0.560 mmol) followed by HATU (51.1 mg, 0.134 mmol). The reaction mixture was stirred at rt for 2.5 h. The mixture was concentrated. The product was purified by reverse phase HPLC (Method A) to afford 2-(cyclohex-1-en-1-yl)-N-(4-(4,4-difluoropiperidin-1-yl)pyridin-3-yl)imidazo[1,2-b]pyridazine-8-carboxamide, 2 TFA (55 mg, 0.081 mmol, 72% yield) as a yellow amorphous solid: ¹H NMR (500 MHz, DMSO-$d_6$) δ 11.84 (s, 1H), 9.20 (s, 1H), 8.76 (d, J=4.7 Hz, 1H), 8.57 (s, 1H), 8.47 (d, J=6.4 Hz, 1H), 7.92 (d, J=4.7 Hz, 1H), 7.52 (d, J=6.4 Hz, 1H), 6.84 (s, 1H), 3.52-3.47 (m, 4H), 2.46 (d, J=1.7 Hz, 2H), 2.24 (d, J=3.5 Hz, 2H), 2.18-2.07 (m, 4H), 1.80-1.72 (m, 2H), 1.70-1.63 (m, 2H); LC/MS (ESI) m/e 439.2 [(M+H)⁺, calcd for $C_{23}H_{25}F_2N_6O$ 439.2]; HPLC (Method A): $t_R$=11.15 min; (Method B) $t_R$=11.71 min.

Example 35

2-(Cyclohex-1-en-1-yl)-N-(4-(2-methylmorpholino)pyridin-3-yl)imidazo[1,2-b]pyridazine-8-carboxamide

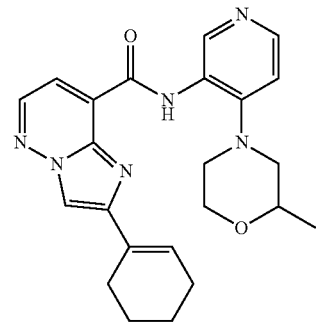 [SMILES: CC1CN(c2ccncc2NC(=O)c2ccnn3cc(C4=CCCCC4)nc23)CCO1]

To a solution of 2-(cyclohex-1-en-1-yl)imidazo[1,2-b]pyridazine-8-carboxylic acid, TFA (20 mg, 0.056 mmol) and 4-(2-methylmorpholino)pyridin-3-amine (12.98 mg, 0.067 mmol) in DMF (1 mL) was added N,N-diisopropylethylamine (0.049 mL, 0.280 mmol) followed by HATU (25.5 mg, 0.067 mmol). The reaction mixture was stirred at rt for 2.5 h. The mixture was concentrated. The product was purified by reverse phase HPLC (Method A) to afford 2-(cyclohex-1-en-1-yl)-N-(4-(2-methylmorpholino)pyridin-3-yl)imidazo[1,2-b]pyridazine-8-carboxamide, 2 TFA (3.3 mg, 5.00 µmol, 9% yield) as a yellow amorphous solid: ¹H NMR (500 MHz, DMSO-$d_6$) δ 11.83 (s, 1H), 9.11 (br. s., 1H), 8.75 (d, J=4.7 Hz, 1H), 8.56 (s, 1H), 8.42 (br. s., 1H), 7.89 (d, J=4.7 Hz, 1H), 7.42 (d, J=4.9 Hz, 1H), 6.89 (t, J=3.8 Hz, 1H), 3.78-3.59 (m, 5H), 3.04-2.96 (m, 1H), 2.77 (t, J=11.0 Hz, 1H), 2.29-2.22 (m, J=5.9, 2.9, 2.9 Hz, 2H), 1.80-1.74 (m, 2H), 1.72-1.65 (m, J=5.8 Hz, 2H), 1.28-1.22 (m, 2H), 1.02 (d, J=6.3 Hz, 3H); LC/MS (ESI) m/e 419.2 [(M+H)+, calcd for $C_{23}H_{27}N_6O_2$ 419.2]; HPLC (Method A): $t_R$=10.08 min; (Method B) $t_R$=10.47 min.

Example 36

N-(4-Morpholinopyridin-3-yl)-2-(pyridin-3-yl)imidazo[1,2-b]pyridazine-8-carboxamide

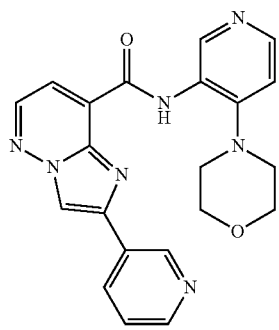 [SMILES: O=C(Nc1cnccc1N1CCOCC1)c1ccnn2cc(-c3cccnc3)nc12]

Part A. Ethyl 6-chloro-2-(pyridin-3-yl)imidazo[1,2-b]pyridazine-8-carboxylate

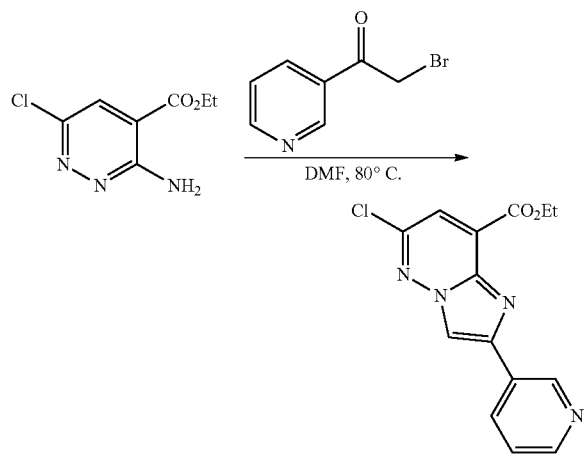

Ethyl 3-amino-6-chloropyridazine-4-carboxylate (300 mg, 1.488 mmol) was added to 2-bromo-1-(pyridin-3-yl)ethanone (357 mg, 1.786 mmol) in Ethanol (10 mL). The solution was heated to 80° C. for 4 h. Additional 2-bromo-1-(pyridin-3-yl)ethanone (200 mg, 1 mmol, 06 eq) was added and the reaction was heated to 80° C. for 12 h. LCMS showed 50% conversion of starting material to the desired product. Additional 2-bromo-1-(pyridin-3-yl)ethanone (200 mg, 1 mmol, 06 eq) was added and the reaction was heated to 80° C. for 12 h. The reaction mixture was concentrated to remove ethanol. The resulting orange liquid was partitioned between ether (30 mL) and saturated aq. NaHCO₃ solution (20 mL). The organic layer was washed with water (20 mL) and saturated aq. NaCl solution (20 mL), dried over MgSO₄, filtered and concentrated. The residue was purified by column chromatography on silica gel (50-80% ethyl acetate in hexane ethyl acetate in hexanes; 40 g column) to afford ethyl 6-chloro-2-(pyridin-3-yl)imidazo[1,2-b]pyridazine-8-carboxylate (70 mg, 0.231 mmol, 16% yield) as a red oil: $^1$H NMR (400 MHz, CHLOROFORM-d) δ 9.20 (d, J=1.8 Hz, 1H), 8.61 (dd, J=4.8, 1.5 Hz, 1H), 8.38-8.32 (m, 2H), 7.62 (s, 1H), 7.44-7.36 (m, 1H), 4.56 (q, J=7.0 Hz, 2H), 1.50 (t, J=7.2 Hz, 3H); LCMS (ESI) m/e 303.1 [(M+H)$^+$, calcd for $C_{14}H_{12}N_4O_2Cl$ 303.1].

Part B. Ethyl 2-(pyridin-3-yl)imidazo[1,2-b]pyridazine-8-carboxylate and ethyl 2-(pyridin-3-yl)-5,6-dihydroimidazo[1,2-b]pyridazine-8-carboxylate

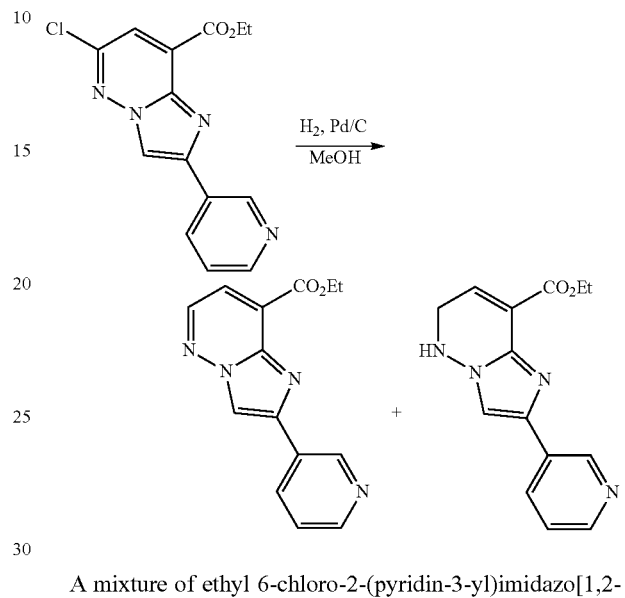

A mixture of ethyl 6-chloro-2-(pyridin-3-yl)imidazo[1,2-b]pyridazine-8-carboxylate (60 mg, 0.198 mmol) and 10% palladium on carbon (42.2 mg, 0.040 mmol) in methanol (010 mL) was shaken in Parr shaker under H₂ at 45 psi for 1.5 h. LCMS suggested the formation of the desired product along with the overreduced product. The mixture was concentrated and the residue was used as is in the next step. LCMS (ESI) m/e 269.1 [(M+H)$^+$, calcd for $C_{14}H_{13}N_4O_2$ 269.1] and LCMS (ESI) m/e 271.1 [(M+H)$^+$, calcd for $C_{14}H_{15}N_4O_2$ 271.1].

Part C. Ethyl 2-(pyridin-3-yl)imidazo[1,2-b]pyridazine-8-carboxylate

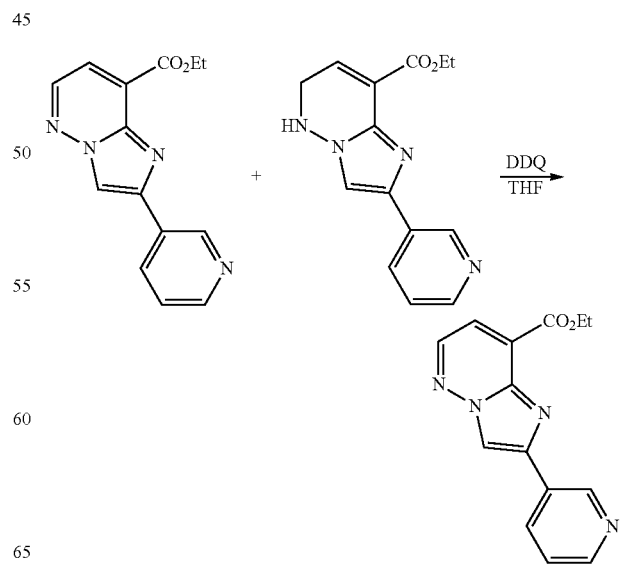

A mixture of ethyl 2-(pyridin-3-yl)imidazo[1,2-b]pyridazine-8-carboxylate (60 mg, 0.224 mmol) and ethyl 2-(pyridin-3-yl)-5,6-dihydroimidazo[1,2-b]pyridazine-8-carboxylate (0 mg), and 2,3-dichloro-5,6-dicyano-1,4-benzoquinone (55.8 mg, 0.246 mmol) in THF (5 mL) was stirred at rt for 1 h. The mixture was concentrated and the residue was purified by column chromatography on silica gel (5%→10% methanol in methylene chloride; 12 g column) to afford ethyl 2-(pyridin-3-yl)imidazo[1,2-b]pyridazine-8-carboxylate (15.00 mg, 0.056 mmol, 25% yield) as a red solid: $^1$H NMR (400 MHz, METHANOL-$d_4$) δ 9.54 (d, J=1.5 Hz, 1H), 9.09 (dt, J=8.2, 1.7 Hz, 1H), 8.99 (s, 1H), 8.78 (d, J=5.5 Hz, 1H), 8.67 (d, J=4.8 Hz, 1H), 8.05 (dd, J=8.0, 5.5 Hz, 1H), 7.82 (d, J=4.5 Hz, 1H), 4.56 (q, J=7.0 Hz, 2H), 1.49 (t, J=7.2 Hz, 3H); LCMS (ESI) m/e 269.1 [(M+H)$^+$, calcd for $C_{14}H_{13}N_4O_2$ 269.1].

Part D. 2-(Pyridin-3-yl)imidazo[1,2-b]pyridazine-8-carboxylic acid

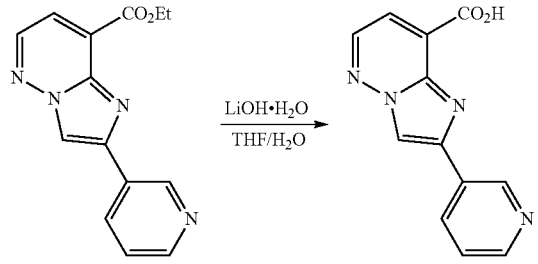 [SMILES: CCOC(=O)c1ccnn2cc(-c3cccnc3)nc12 ; "LiOH·H2O" ; O=C(O)c1ccnn2cc(-c3cccnc3)nc12]

A mixture of ethyl 2-(pyridin-3-yl)imidazo[1,2-b]pyridazine-8-carboxylate (25 mg, 0.093 mmol), lithium hydroxide monohydrate (11.73 mg, 0.280 mmol) in water (0.100 mL) and THF (2 mL) was stirred at room temperature for 2 h. The mixture was concentrated to afford 2-(pyridin-3-yl)imidazo[1,2-b]pyridazine-8-carboxylic acid (25 mg, 78% yield). The product was used directly in the next step. LCMS (ESI) m/e 241.1 [(M+H)$^+$, calcd for $C_{12}H_9N_4O_2$ 241.1].

Part E. N-(4-Morpholinopyridin-3-yl)-2-(pyridin-3-yl)imidazo[1,2-b]pyridazine-8-carboxamide

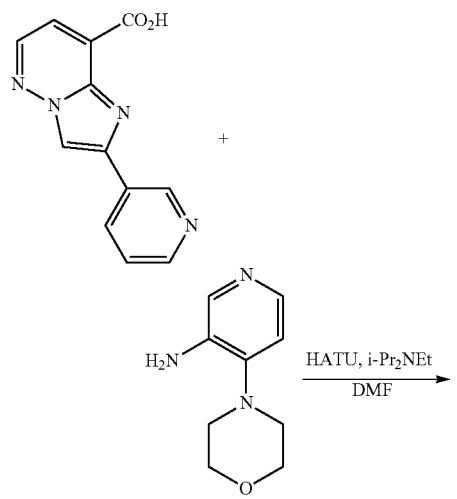

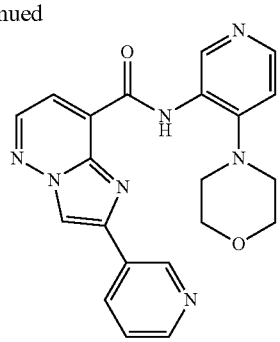

To a solution of 2-(pyridin-3-yl)imidazo[1,2-b]pyridazine-8-carboxylic acid (20 mg, 0.083 mmol) and N,N-diisopropylethylamine (0.087 mL, 0.500 mmol) in DMF (1 mL) at rt was added 4-morpholinopyridin-3-amine (29.8 mg, 0.167 mmol) and HATU (63.3 mg, 0.167 mmol). The reaction mixture was stirred at rt for 2 h. The mixture was concentrated and the residue was purified by column chromatography on silica gel (30%→50% ethyl acetate in hexanes; 12 g column) to afford N-(4-morpholinopyridin-3-yl)-2-(pyridin-3-yl)imidazo[1,2-b]pyridazine-8-carboxamide (5 mg, 0.012 mmol, 15% yield) as a tan solid. The product was purified further by reverse phase HPLC (Method A) to afford N-(4-morpholinopyridin-3-yl)-2-(pyridin-3-yl)imidazo[1,2-b]pyridazine-8-carboxamide, 2 TFA (1 mg, 1.315 μmol) as a yellow solid: $^1$H NMR (400 MHz, METHANOL-$d_4$) δ 9.46 (br. s., 1H), 9.20 (s, 1H), 9.02 (s, 1H), 8.81-8.64 (m, 3H), 8.41 (d, J=6.5 Hz, 1H), 8.06 (d, J=4.8 Hz, 1H), 7.75 (d, J=7.3 Hz, 1H), 7.59 (d, J=7.0 Hz, 1H), 3.77-3.69 (m, 4H), 3.69-3.60 (m, 4H); LCMS (ESI) m/e 402.2 [(M+H)$^+$, calcd for $C_{21}H_{20}N_7O_2$ 402.2]; HPLC (Method A): $t_R$=10.28 min; (Method B) $t_R$=10.93 min.

Example 37

N-(4-Ethoxypyrimidin-5-yl)-2-phenylimidazo[1,2-b]pyridazine-8-carboxamide

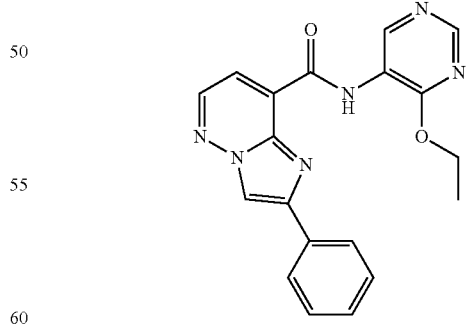

To a solution of 2-phenylimidazo[1,2-b]pyridazine-8-carboxylic acid (40 mg, 0.167 mmol) and 4-ethoxypyrimidin-5-amine (46.5 mg, 0.334 mmol) in DMF (2 mL) was added N,N-diisopropylethylamine (0.175 mL, 1.003 mmol) and HATU (127 mg, 0.334 mmol). The reaction mixture was stirred at rt for 2 h. The reaction mixture was transferred to a separatory funnel containing saturated aqueous NaHCO₃ solution (15 mL). The aqueous layer was extracted with ethyl acetate (3×15 mL). The combined organic layers were washed with brine (20 mL), dried over MgSO₄, filtered, and concentrated. The residue was purified by column chromatography on silica gel (80%→90% ethyl acetate in hexanes; 24 g column) to afford N-(4-ethoxypyrimidin-5-yl)-2-phenylimidazo[1,2-b]pyridazine-8-carboxamide (20 mg, 0.055 mmol, 33% yield) as a yellow solid: ¹H NMR (400 MHz, DMSO-d₆) δ 12.28 (s, 1H), 9.64 (s, 1H), 9.17 (s, 1H), 8.81 (d, J=4.8 Hz, 1H), 8.65 (s, 1H), 8.27-8.23 (m, 2H), 7.92 (d, J=4.8 Hz, 1H), 7.60-7.55 (m, 2H), 7.50-7.45 (m, 1H), 4.79 (q, J=7.0 Hz, 2H), 1.47 (t, J=7.0 Hz, 3H); LCMS (ESI) m/e 361.1 [(M+H)+, calcd for C₁₉H₁₇N₆O₂ 361.1]; HPLC (Method A): t$_R$=13.50 min; (Method B) t$_R$=12.55 min.

Example 38

2-Phenyl-N-(4-(2,2,2-trifluoroethoxy)pyrimidin-5-yl)imidazo[1,2-b]pyridazine-8-carboxamide

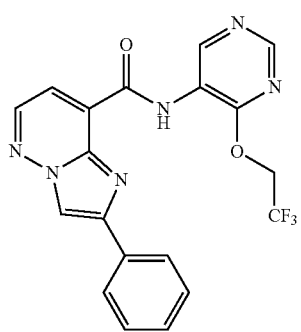 [SMILES: O=C(Nc1cncnc1OCC(F)(F)F)c1ccnn2cc(-c3ccccc3)nc12]

To a solution of 2-phenylimidazo[1,2-b]pyridazine-8-carboxylic acid (40 mg, 0.167 mmol) and 4-(2,2,2-trifluoroethoxy)pyrimidin-5-amine (64.6 mg, 0.334 mmol) in DMF (2 mL) was added N,N-diisopropylethylamine (0.175 mL, 1.003 mmol) and HATU (127 mg, 0.334 mmol). The reaction mixture was stirred at rt for 2 h. The reaction mixture was transferred to a separatory funnel containing saturated aqueous NaHCO₃ solution (15 mL). The aqueous layer was extracted with ethyl acetate (3×15 mL). The combined organic layers were washed with brine (20 mL), dried over MgSO₄, filtered, and concentrated. The residue was purified by column chromatography on silica gel (10%→40% ethyl acetate in hexanes; 25 g column) to afford 2-phenyl-N-(4-(2,2,2-trifluoroethoxy)pyrimidin-5-yl)imidazo[1,2-b]pyridazine-8-carboxamide (22 mg, 0.053 mmol, 32% yield) as a yellow solid: ¹H NMR (400 MHz, DMSO-d₆) δ 12.14 (s, 1H), 9.70 (s, 1H), 9.17 (s, 1H), 8.81 (d, J=4.8 Hz, 1H), 8.75 (s, 1H), 8.22-8.17 (m, 2H), 7.94 (d, J=4.8 Hz, 1H), 7.58-7.51 (m, 2H), 7.48-7.41 (m, 1H), 5.44 (q, J=8.8 Hz, 2H); LCMS (ESI) m/e 415.2 [(M+H)⁺, calcd for C₁₉H₁₄N₆O₂F₃ 415.1]; HPLC (Method A): t$_R$=15.99 min; (Method B) t$_R$=14.10 min.

Preparation of 3-((cyclopropylmethyl)amino)imidazo[1,2-b]pyridazine-8-carboxylic acid

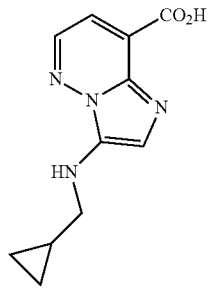 [SMILES: O=C(O)c1ccnn2c(NCC3CC3)cnc12]

Part A. Ethyl 3,6-dichloropyridazine-4-carboxylate

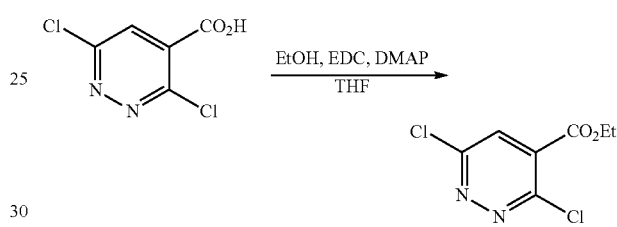

To a mixture of 3,6-dichloropyridazine-4-carboxylic acid (15.0 g, 78 mmol) in THF (150 mL) was added ethanol (18.15 mL, 311 mmol) and DMAP (0.950 g, 7.77 mmol). EDC (16.39 g, 85 mmol) was then added in portions over 1 min. The reaction was mildly exothermic. The reaction was stirred at room temperature for 16 h. The reaction mixture was transferred to a separatory funnel containing saturated aqueous NaHCO₃ solution (150 mL). The aqueous layer was extracted with ether (3×250 mL). The combined organic layers were washed with brine (100 mL), dried over MgSO₄, filtered, and concentrated. The residue was purified by column chromatography on silica gel (20%→40% ethyl acetate in hexanes; 300 g column) to afford ethyl 3,6-dichloropyridazine-4-carboxylate (13.2 g, 59.7 mmol, 77% yield) as a colorless oil: ¹H NMR (400 MHz, CDCl₃) δ 7.88 (s, 1H), 4.50 (q, J=7.0 Hz, 2H), 1.46 (t, J=7.2 Hz, 3H); LCMS (ESI) m/e 221.1 [(M+H)⁺, calcd for C₇H₇Cl₂N₂O₂ 221.0].

Part B. Ethyl 6-chloro-3-((4-methoxybenzyl)amino)pyridazine-4-carboxylate

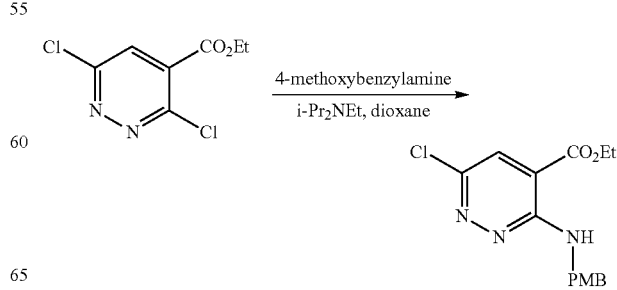

A mixture of ethyl 3,6-dichloropyridazine-4-carboxylate (2.00 g, 9.05 mmol), 4-methoxyphenyl)methanamine (1.241 g, 9.05 mmol) and N,N-diisopropylethylamine (4.74 mL, 27.1 mmol) in dioxane (20 mL) in a sealed tube was heated at 80° C. for 20 minutes. The solvent was evaporated and residue was purified by column chromatography on silica gel (20%→30% ethyl acetate in hexanes; 25 g column) to afford ethyl 6-chloro-3-((4-methoxybenzyl)amino) pyridazine-4-carboxylate (2.50 g, 7.77 mmol, 86% yield) as a green solid: $^1$H NMR (400 MHz, CDCl$_3$) δ 7.86 (br. s., 1H), 7.76 (s, 1H), 7.36 (d, J=8.8 Hz, 2H), 6.90 (d, J=8.8 Hz, 2H), 4.80 (d, J=5.3 Hz, 2H), 4.39 (q, J=7.1 Hz, 2H), 3.82 (s, 3H), 1.41 (t, J=7.0 Hz, 3H); LC/MS (ESI) m/e 322.1 [(M+H)$^+$, calcd for C$_{15}$H$_{17}$ClN$_3$O$_3$ 322.1].

Part C. Ethyl 3-amino-6-chloropyridazine-4-carboxylate

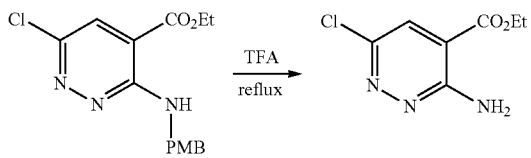

A mixture of ethyl 6-chloro-3-((4-methoxybenzyl)amino) pyridazine-4-carboxylate (2.50 g, 7.77 mmol) and TFA (11.97 ml, 155 mmol) was heated at reflux for 3 h. The reaction mixture was concentrated and transferred to a separatory funnel containing saturated aqueous NaHCO$_3$ solution (15 mL). The aqueous layer was extracted with ethyl acetate (3×20 mL). The combined organic layers were washed with brine (15 mL), dried over MgSO$_4$, filtered, and concentrated. The residue was purified by column chromatography on silica gel (60%→80% ethyl acetate in hexanes; 12 g column) to afford ethyl 3-amino-6-chloropyridazine-4-carboxylate (1.00 g, 4.96 mmol, 64% yield) as a green solid: $^1$H NMR (400 MHz, CDCl$_3$) δ 7.77 (s, 1H), 7.00 (s br, 2H), 4.40 (q, J=7.0 Hz, 2H), 1.40 (t, J=7.2 Hz, 3H); LCMS (ESI) m/e 202.0 [(M+H)$^+$, calcd for C$_7$H$_9$N$_3$O$_2$Cl 202.6].

Part D. Ethyl 6-chloroimidazo[1,2-b]pyridazine-8-carboxylate

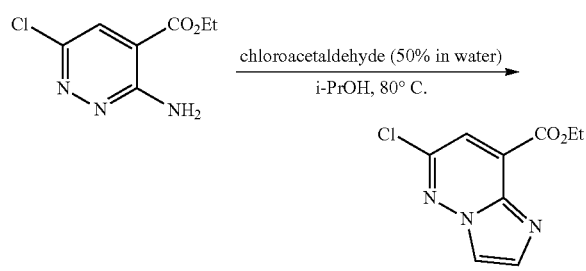

Chloroacetaldehyde (50% in H$_2$O) (5.04 mL, 39.7 mmol) was added to ethyl 3-amino-6-chloropyridazine-4-carboxylate (1.00 g, 4.96 mmol) in isopropanol (20 mL). The solution was heated at 80° C. for 4 h. The reaction mixture was concentrated to remove isopropanol. The resulting orange liquid was partitioned between ether (30 mL) and saturated aq. NaHCO$_3$ solution (20 mL). The organic layer was washed with water (20 mL) and brine (20 mL), dried over MgSO$_4$, filtered and concentrated. The residue was purified by column chromatography on silica gel (60%→80% ethyl acetate in hexanes; 25 g column) to afford ethyl 6-chloroimidazo[1,2-b]pyridazine-8-carboxylate (750 mg, 3.32 mmol, 67% yield) as a green solid: $^1$H NMR (400 MHz, METHANOL-d$_4$) δ 8.23 (d, J=1.5 Hz, 1H), 7.88 (d, J=1.3 Hz, 1H), 7.73 (s, 1H), 4.52 (q, J=7.0 Hz, 2H), 1.45 (t, J=7.2 Hz, 3H); LCMS (ESI) m/e 226.0 [(M+H)$^+$, calcd for C$_9$H$_9$N$_3$O$_2$Cl 226.0].

Part E. Ethyl 6-chloro-3-nitroimidazo[1,2-b]pyridazine-8-carboxylate

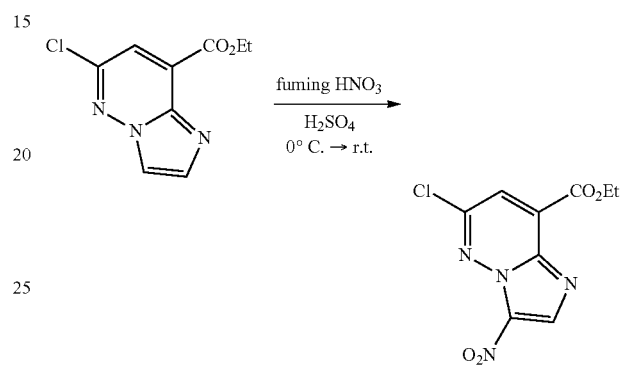

A 50 mL round bottom flask was charged with ethyl 6-chloroimidazo[1,2-b]pyridazine-8-carboxylate (600 mg, 2.66 mmol) and was cooled to 0° C. Sulfuric acid (3 mL, 56.3 mmol) was added to the flask followed by the addition of fuming nitric acid (3.57 mL, 80 mmol). The mixture was stirred at 0° C. for 30 min and then at room temperature for 5 h. The mixture was neutralized with sat. aqueous Na$_2$CO$_3$ solution. The mixture was transferred to a separatory funnel and was extracted with ethyl acetate (3×50 mL). The combined organic layers were washed with brine (50 mL), dried over MgSO$_4$, filtered, and concentrated to afford ethyl 6-chloro-3-nitroimidazo[1,2-b]pyridazine-8-carboxylate (480 mg, 1.774 mmol, 67% yield) as a yellow solid: $^1$H NMR (400 MHz, METHANOL-d$_4$) δ 8.74 (s, 1H), 8.12 (s, 1H), 4.55 (q, J=7.1 Hz, 2H), 1.46 (t, J=7.2 Hz, 3H); LCMS (ESI) m/e 271.0 [(M+H)$^+$, calcd for C$_9$H$_5$N$_4$O$_4$Cl 271.0].

Part F. Ethyl 3-aminoimidazo[1,2-b]pyridazine-8-carboxylate

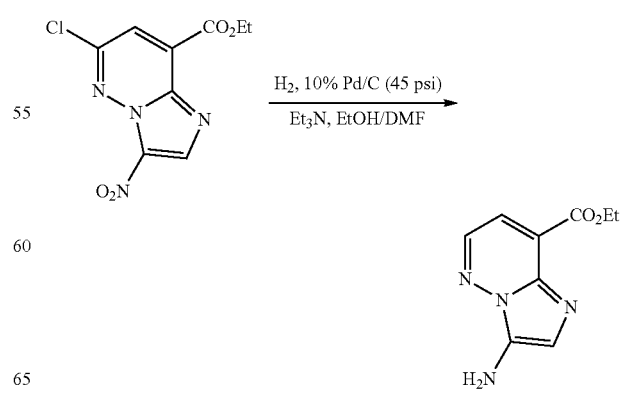

A mixture of ethyl 6-chloro-3-nitroimidazo[1,2-b]pyridazine-8-carboxylate (480 mg, 1.774 mmol), 10% palladium on carbon (378 mg, 0.355 mmol) and triethylamine (0.494 mL, 3.55 mmol) in EtOH (10 mL) and DMF (10.00 mL) was placed under a hydrogen atmosphere at 45 psi in a Parr shaker for 4 h. The catalyst was removed by filtration through a pad of Celite and the filtrate was concentrated. The residue was purified by column chromatography on silica gel (10% methanol in dichloromethane; 25 g column) to afford ethyl 3-aminoimidazo[1,2-b]pyridazine-8-carboxylate (300 mg, 1.455 mmol, 82% yield) as a dark red oil: $^1$H NMR (400 MHz, METHANOL-$d_4$) δ 8.52 (d, J=4.8 Hz, 1H), 7.44 (d, J=4.8 Hz, 1H), 7.24 (s, 1H), 4.50 (q, J=7.0 Hz, 2H), 1.44 (t, J=7.2 Hz, 3H); LCMS (ESI) m/e 207.1 [(M+H)$^+$, calcd for $C_9H_{11}N_4O_2$ 207.1].

Part G. Ethyl 3-((cyclopropylmethyl)amino)imidazo[1,2-b]pyridazine-8-carboxylate

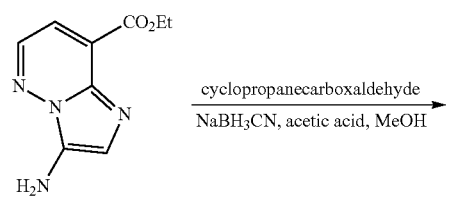

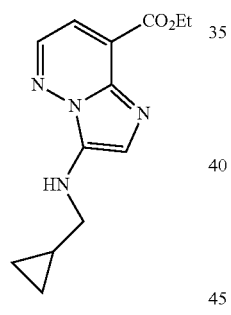

To a solution of ethyl 3-aminoimidazo[1,2-b]pyridazine-8-carboxylate (150 mg, 0.727 mmol) and acetic acid (0.083 mL, 1.455 mmol) in MeOH (5 mL) was added cyclopropanecarboxaldehyde (0.055 mL, 0.727 mmol). The mixture was stirred at room temperature for 1 h. Sodium cyanoborohydride (91 mg, 1.455 mmol) was added and the mixture was stirred for 2 h at room temperature. The mixture was concentrated and the residue was purified by column chromatography on silica gel (30%→80% ethyl acetate in hexanes; 12 g column) to afford ethyl 3-((cyclopropylmethyl)amino)imidazo[1,2-b]pyridazine-8-carboxylate (95 mg, 0.365 mmol, 50% yield) as a red solid: $^1$H NMR (400 MHz, CHLOROFORM-d) δ 8.35 (d, J=4.8 Hz, 1H), 7.36 (d, J=4.8 Hz, 1H), 7.29 (s, 1H), 4.55 (q, J=7.0 Hz, 2H), 3.19 (d, J=7.0 Hz, 2H), 1.46 (t, J=7.2 Hz, 3H), 1.28-1.12 (m, 1H), 0.64-0.56 (m, 2H), 0.34-0.28 (m, 2H); LCMS (ESI) m/e 261.2 [(M+H)$^+$, calcd for $C_{13}H_{17}N_4O_2$ 261.1].

Part H. 3-((Cyclopropylmethyl)amino)imidazo[1,2-b]pyridazine-8-carboxylic acid

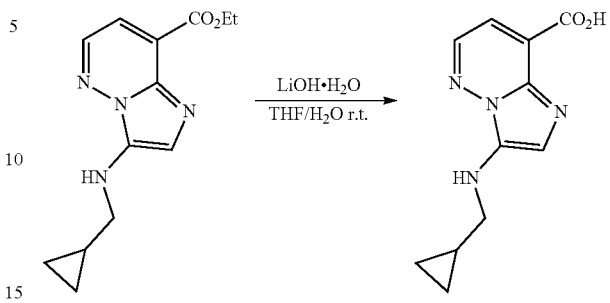

A mixture of ethyl 3-((cyclopropylmethyl)amino)imidazo[1,2-b]pyridazine-8-carboxylate (110 mg, 0.423 mmol) and lithium hydroxide monohydrate (70.9 mg, 1.690 mmol) in water (0.200 mL) and THF (5 mL) was stirred at room temperature for 2 h. The solvent was then concentrated to afford 3-((cyclopropylmethyl)amino)imidazo[1,2-b]pyridazine-8-carboxylic acid (180 mg, 0.388 mmol, 92% yield) as a red solid. The crude product was used directly in the next step. LCMS (ESI) m/e 233.1 [(M+H)$^+$, calcd for $C_{11}H_{13}N_4O_2$ 233.1].

Example 39

3-((Cyclopropylmethyl)amino)-N-(pyridin-3-yl)imidazo[1,2-b]pyridazine-8-carboxamide

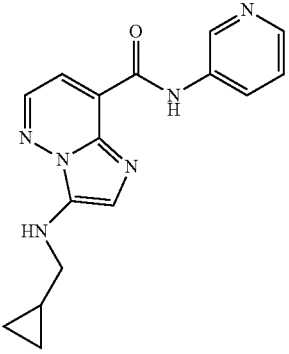 [SMILES: O=C(Nc1cccnc1)c1ccnn2c(NCC3CC3)cnc12]

To a mixture of 3-((cyclopropylmethyl)amino)imidazo[1,2-b]pyridazine-8-carboxylic acid (25 mg, 0.108 mmol), pyridin-3-amine (20.26 mg, 0.215 mmol), and N,N-diisopropylethylamine (0.056 mL, 0.323 mmol) in DMF (1 mL) was added HATU (61.4 mg, 0.161 mmol). The reaction mixture was stirred at room temperature for 4 h. The reaction mixture was transferred to a separatory funnel containing saturated aqueous NaHCO$_3$ solution (10 mL). The aqueous layer was extracted with methylene chloride (3×10 mL). The combined organic layers were washed with brine (10 mL), dried over MgSO$_4$, filtered, and concentrated. The residue was purified by reverse phase HPLC (Method A) to afford 3-((cyclopropylmethyl)amino)-N-(pyridin-3-yl)imidazo[1,2-b]pyridazine-8-carboxamide, 2 TFA (10 mg, 0.017 mmol, 16% yield) as a red solid: $^1$H NMR (400 MHz, DMSO-$d_6$) δ 11.96 (s, 1H), 8.96 (d, J=2.3 Hz, 1H), 8.69 (d, J=4.8 Hz, 1H), 8.42 (dd, J=4.8, 1.5 Hz, 1H), 8.28-8.25 (m, 1H), 7.56 (d, J=4.8 Hz, 1H), 7.50 (dd, J=7.9, 4.6 Hz, 1H), 7.38 (s, 1H), 6.05 (t, J=6.3 Hz, 1H), 3.17 (t, J=6.4 Hz, 2H), 1.19 (t, J=7.0

Hz, 1H), 0.51-0.46 (m, 2H), 0.33-0.29 (m, 2H); LCMS (ESI) m/e 309.2 [(M+H)⁺, calcd for $C_{16}H_{17}N_6O$ 309.1]; HPLC (Method A): $t_R$=6.12 min; (Method B) $t_R$=6.50 min.

Example 40

3-((Cyclopropylmethyl)amino)-N-(4-methylpyridin-3-yl)imidazo[1,2-b]pyridazine-8-carboxamide

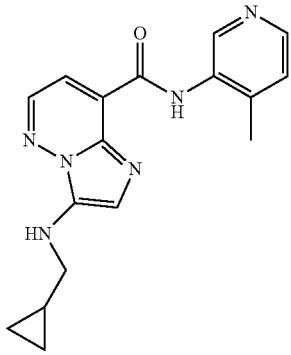 [SMILES: Cc1ccncc1NC(=O)c1ccnn2c(NCC3CC3)cnc12]

To a mixture of 3-((cyclopropylmethyl)amino)imidazo[1,2-b]pyridazine-8-carboxylic acid (25 mg, 0.108 mmol), 4-methylpyridin-3-amine (23.28 mg, 0.215 mmol), and N,N-diisopropylethylamine (0.056 mL, 0.323 mmol) in DMF (1 mL) was added HATU (61.4 mg, 0.161 mmol). The reaction mixture was stirred at room temperature for 4 h. The reaction mixture was transferred to a separatory funnel containing saturated aqueous NaHCO₃ solution (10 mL). The aqueous layer was extracted with methylene chloride (3×10 mL). The combined organic layers were washed with brine (10 mL), dried over MgSO₄, filtered, and concentrated. The residue was purified by reverse phase HPLC (Method A) to afford 3-((cyclopropylmethyl)amino)-N-(4-methylpyridin-3-yl)imidazo[1,2-b]pyridazine-8-carboxamide (10 mg, 0.030 mmol, 28% yield) as a red solid: ¹H NMR (400 MHz, CHLOROFORM-d) δ 11.87 (br. s., 1H), 9.48 (s, 1H), 8.49 (d, J=4.5 Hz, 1H), 8.36 (d, J=5.0 Hz, 1H), 7.75 (d, J=4.8 Hz, 1H), 7.29 (s, 1H), 7.22 (d, J=5.0 Hz, 1H), 7.18 (s, 1H), 3.22 (t, J=6.5 Hz, 2H), 2.55 (s, 3H), 1.29-1.20 (m, 1H), 0.69-0.62 (m, 2H), 0.38-0.31 (m, 2H); LCMS (ESI) m/e 323.2 [(M+H)⁺, calcd for $C_{17}H_{19}N_6O$ 323.2]; HPLC (Method A): $t_R$=7.47 min; (Method B) $t_R$=8.06 min.

Example 41

3-((Cyclopropylmethyl)amino)-N-(4-isopropoxypyridin-3-yl)imidazo[1,2-b]pyridazine-8-carboxamide

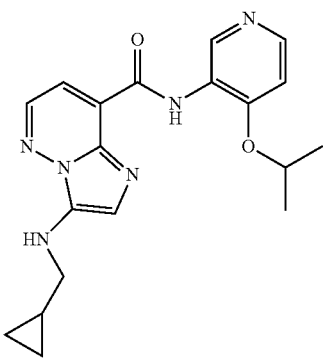 [SMILES: CC(C)Oc1ccncc1NC(=O)c1ccnn2c(NCC3CC3)cnc12]

To a mixture of 3-((cyclopropylmethyl)amino)imidazo[1,2-b]pyridazine-8-carboxylic acid (20 mg, 0.086 mmol), 4-isopropoxypyridin-3-amine, 2 HCl (38.8 mg, 0.172 mmol), and N,N-diisopropylethylamine (0.075 mL, 0.431 mmol) in DMF (1 mL) was added HATU (49.1 mg, 0.129 mmol). The reaction mixture was stirred at room temperature for 12 h. The mixture was concentrated and the residue was purified by reverse phase HPLC (Method A) to afford 3-((cyclopropylmethyl)amino)-N-(4-isopropoxypyridin-3-yl)imidazo[1,2-b]pyridazine-8-carboxamide, 2 TFA (24 mg, 0.040 mmol, 46% yield) as a red solid: ¹H NMR (400 MHz, DMSO-d₆) δ 12.82 (s, 1H), 9.71 (s, 1H), 8.71 (d, J=4.5 Hz, 1H), 8.68 (d, J=6.5 Hz, 1H), 7.81 (d, J=6.3 Hz, 1H), 7.62 (d, J=4.5 Hz, 1H), 7.38 (s, 1H), 5.25 (dt, J=12.0, 5.9 Hz, 1H), 3.18 (d, J=6.8 Hz, 2H), 1.57 (d, J=6.0 Hz, 6H), 1.25-1.13 (m, 1H), 0.52-0.46 (m, 2H), 0.34-0.28 (m, 2H); LCMS (ESI) m/e 367.3 [(M+H)⁺, calcd for $C_{19}H_{23}N_6O_2$ 367.2]; HPLC (Method A): $t_R$=9.52 min; (Method B) $t_R$=9.90 min.

Example 42

3-((Cyclopropylmethyl)amino)-N-(4-phenylpyridin-3-yl)imidazo[1,2-b]pyridazine-8-carboxamide

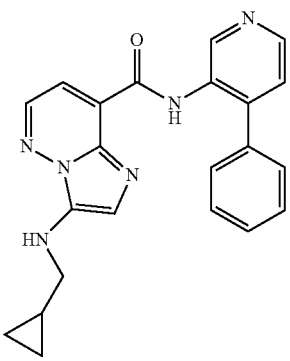 [SMILES: O=C(Nc1cnccc1-c1ccccc1)c1ccnn2c(NCC3CC3)cnc12]

To a mixture of 3-((cyclopropylmethyl)amino)imidazo[1,2-b]pyridazine-8-carboxylic acid (20 mg, 0.086 mmol), 4-phenylpyridin-3-amine, 2 HCl (41.9 mg, 0.172 mmol), and N,N-diisopropylethylamine (0.075 mL, 0.431 mmol) in DMF (1 mL) was added HATU (49.1 mg, 0.129 mmol). The reaction mixture was stirred at room temperature for 12 h. The mixture was concentrated and the residue was purified by reverse phase HPLC (Method A) to afford 3-((cyclopropylmethyl)amino)-N-(4-phenylpyridin-3-yl)imidazo[1,2-b]pyridazine-8-carboxamide, 2 TFA (15 mg, 0.023 mmol, 27% yield) as a red solid: ¹H NMR (400 MHz, DMSO-d₆) δ 11.87 (s, 1H), 9.59 (s, 1H), 8.65 (d, J=4.8 Hz, 1H), 8.56 (d, J=5.0 Hz, 1H), 7.63-7.48 (m, 8H), 6.87 (s, 1H), 3.09 (d, J=6.8 Hz, 2H), 0.90-0.81 (m, 1H), 0.53-0.40 (m, 2H), 0.32-0.22 (m, 2H); LCMS (ESI) m/e 385.2 [(M+H)⁺, calcd for $C_{22}H_{21}N_6O$ 385.2]; HPLC (Method A): $t_R$=9.76 min; (Method B) $t_R$=10.16 min.

Example 43

3-((Cyclopropylmethyl)amino)-N-(4-(4,4-difluoropiperidin-1-yl)pyridin-3-yl)imidazo[1,2-b]pyridazine-8-carboxamide

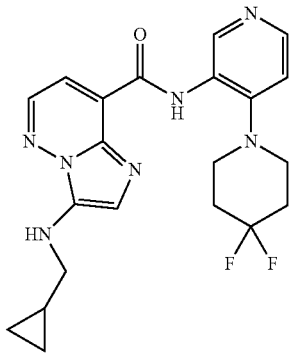 [SMILES: O=C(Nc1cnccc1N1CCC(F)(F)CC1)c1ccnn2c(NCC3CC3)cnc12]

To a solution of 3-((cyclopropylmethyl)amino)imidazo[1,2-b]pyridazine-8-carboxylic acid (30 mg, 0.129 mmol), 4-(4,4-difluoropiperidin-1-yl)pyridin-3-amine (55.1 mg, 0.258 mmol), and N,N-diisopropylethylamine (0.135 mL, 0.775 mmol) in DMF (1 mL) was added HATU (98 mg, 0.258 mmol). The reaction mixture was stirred at rt for 4 h. The mixture was transferred to a separatory funnel containing saturated aqueous NaHCO$_3$ solution (5 mL). The aqueous layer was extracted with ethyl acetate (3×10 mL). The combined organic layers were washed with brine (10 mL), dried over MgSO$_4$, filtered, and concentrated. The residue was purified by reverse phase HPLC (Method A) to afford 3-((cyclopropylmethyl)amino)-N-(4-(4,4-difluoropiperidin-1-yl)pyridin-3-yl)imidazo[1,2-b]pyridazine-8-carboxamide, 2 TFA (26 mg, 0.039 mmol, 30% yield) as a red oil: $^1$H NMR (400 MHz, DMSO-d$_6$) δ 12.00 (s, 1H), 9.34 (s, 1H), 8.79 (d, J=4.8 Hz, 1H), 8.73 (d, J=4.8 Hz, 1H), 8.52 (d, J=6.5 Hz, 1H), 7.64 (d, J=4.8 Hz, 1H), 7.62 (d, J=6.5 Hz, 1H), 7.35 (s, 1H), 3.53-3.48 (m, 4H), 3.17 (d, J=6.8 Hz, 2H), 2.32-2.18 (m, 4H), 1.22-1.13 (m, 1H), 0.52-0.45 (m, 2H), 0.33-0.28 (m, 2H); LCMS (ESI) m/e 428.2 [(M+H)$^+$, calcd for C$_{21}$H$_{24}$N$_7$OF$_2$ 428.2]; HPLC (Method A): t$_R$=9.10 min; (Method B) t$_R$=9.50 min.

Example 44

3-((Cyclopropylmethyl)amino)-N-(4-morpholinopyridin-3-yl)imidazo[1,2-b]pyridazine-8-carboxamide

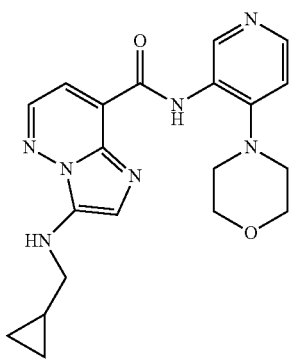 [SMILES: O=C(Nc1cnccc1N1CCOCC1)c1ccnn2c(NCC3CC3)cnc12]

To a solution of 3-((cyclopropylmethyl)amino)imidazo[1,2-b]pyridazine-8-carboxylic acid (30 mg, 0.129 mmol), 4-morpholinopyridin-3-amine (46.3 mg, 0.258 mmol), and N,N-diisopropylethylamine (0.135 mL, 0.775 mmol) in DMF (1 mL) was added HATU (98 mg, 0.258 mmol). The reaction mixture was stirred at rt for 4 h. The mixture was transferred to a separatory funnel containing saturated aqueous NaHCO$_3$ solution (5 mL). The aqueous layer was extracted with ethyl acetate (3×10 mL). The combined organic layers were washed with brine (10 mL), dried over MgSO$_4$, filtered, and concentrated. The residue was purified by reverse phase HPLC (Method A) to afford 3-((cyclopropylmethyl)amino)-N-(4-morpholinopyridin-3-yl)imidazo[1,2-b]pyridazine-8-carboxamide, 2 TFA (28 mg, 0.043 mmol, 33% yield) as a red oil: $^1$H NMR (400 MHz, DMSO-d$_6$) 12.01 (s, 1H), 9.34 (s, 1H), 8.72 (d, J=4.5 Hz, 1H), 8.49 (d, J=5.8 Hz, 1H), 7.62 (d, J=4.5 Hz, 1H), 7.51 (d, J=6.5 Hz, 1H), 7.47 (s, 1H), 3.91-3.81 (m, 4H), 3.40 (br. s., 4H), 3.18 (d, J=6.8 Hz, 2H), 1.22-1.12 (m, 1H), 0.54-0.43 (m, 2H), 0.35-0.25 (m, 2H); LCMS (ESI) m/e 394.3 [(M+H)+, calcd for C$_{20}$H$_{24}$N$_7$O$_2$ 394.2]; HPLC (Method A): t$_R$=7.69 min; (Method B) t$_R$=7.93 min.

Example 45

3-((Cyclopropylmethyl)amino)-N-(4-(2-methylmorpholino)pyridin-3-yl)imidazo[1,2-b]pyridazine-8-carboxamide

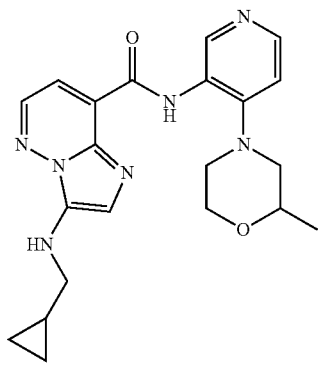 [SMILES: CC1CN(c2ccncc2NC(=O)c2ccnn3c(NCC4CC4)cnc23)CCO1]

To a solution of 3-((cyclopropylmethyl)amino)imidazo[1,2-b]pyridazine-8-carboxylic acid (30 mg, 0.129 mmol), 4-(2-methylmorpholino)pyridin-3-amine (49.9 mg, 0.258 mmol), and N,N-diisopropylethylamine (0.135 mL, 0.775 mmol) in DMF (1 mL) was added HATU (98 mg, 0.258 mmol). The reaction mixture was stirred at rt for 4 h. LCMS suggested the formation of the desired product. The reaction mixture was transferred to a separatory funnel containing saturated aqueous NaHCO$_3$ solution (5 mL). The aqueous layer was extracted with ethyl acetate (3×10 mL). The combined organic layers were washed with brine (10 mL), dried over MgSO$_4$, filtered, and concentrated. The residue was purified by reverse phase HPLC (Method A) to afford 3-((cyclopropylmethyl)amino)-N-(4-(2-methylmorpholino)pyridin-3-yl)imidazo[1,2-b]pyridazine-8-carboxamide, 2 TFA (29 mg, 0.043 mmol, 34% yield) as a red oil: $^1$H NMR (400 MHz, DMSO-d$_6$) δ 11.95 (s, 1H), 9.28 (s, 1H), 8.72 (d, J=4.8 Hz, 1H), 8.53-8.46 (m, 1H), 7.61 (d, J=4.5 Hz, 1H), 7.55 (d, J=6.8 Hz, 1H), 7.45 (s, 1H), 3.94-3.70 (m, 7H), 3.18 (d, J=6.8 Hz, 2H), 1.23-1.15 (m, 1H), 1.07 (d, J=6.3 Hz, 3H), 0.53-0.45 (m, 2H), 0.35-0.27 (m, 2H); LCMS (ESI) m/e 408.2 [(M+H)+, calcd for $C_{21}H_{26}N_7O_2$ 408.2]; HPLC (Method A): $t_R$=8.50 min; (Method B) $t_R$=8.35 min.

Example 46

3-(Cyclopropanecarboxamido)-N-(4-isopropoxypyridin-3-yl)imidazo[1,2-b]pyridazine-8-carboxamide

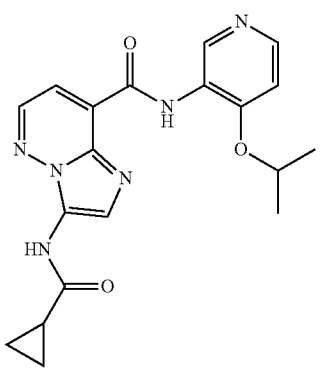 [SMILES: CC(C)Oc1ccncc1NC(=O)c1ccnn2c(NC(=O)C3CC3)cnc12]

Part A. Ethyl 3-(cyclopropanecarboxamido)imidazo[1,2-b]pyridazine-8-carboxylate

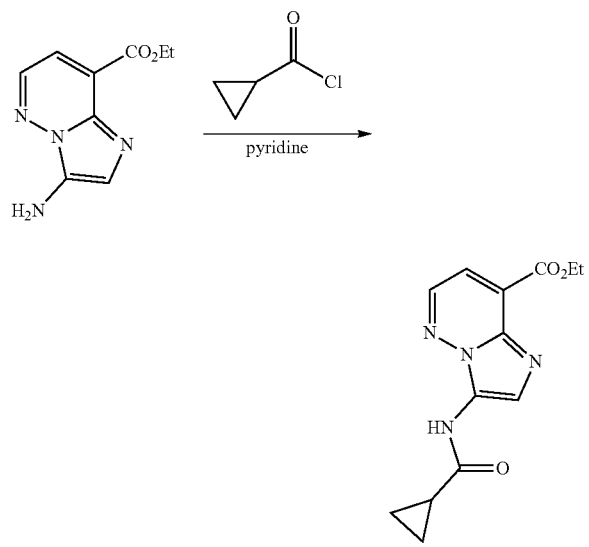

To a solution of ethyl 3-aminoimidazo[1,2-b]pyridazine-8-carboxylate (50 mg, 0.242 mmol) in pyridine (1 mL) at rt was added cyclopropanecarboxylic acid chloride (0.024 mL, 0.267 mmol). The reaction mixture was stirred at rt for 12 h. The mixture was concentrated and the residue was purified by column chromatography on silica gel (40%→60% ethyl acetate in hexanes; 12 g column) to afford ethyl 3-(cyclopropanecarboxamido)imidazo[1,2-b]pyridazine-8-carboxylate (15 mg, 0.055 mmol, 23% yield) as a red oil: LCMS (ESI) m/e 275.1 [(M+H)+, calcd for $C_{13}H_{15}N_4O_3$ 275.1].

Part B. 3-(Cyclopropanecarboxamido)imidazo[1,2-b]pyridazine-8-carboxylic acid

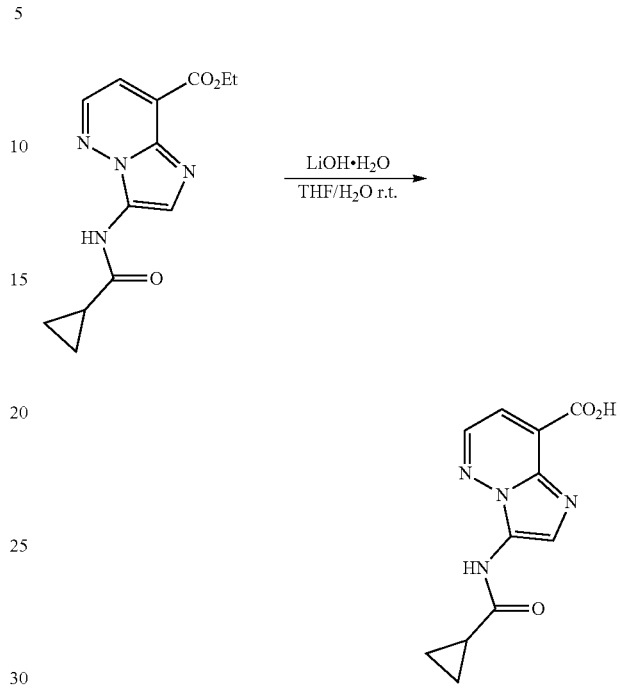

A mixture of ethyl 3-(cyclopropanecarboxamido)imidazo[1,2-b]pyridazine-8-carboxylate (15 mg, 0.055 mmol) and lithium hydroxide monohydrate (3.93 mg, 0.164 mmol) in THF (0.5 mL) and water (0.100 mL) was stirred at room temperature for 2 h. The mixture was concentrated to afford 3-(cyclopropanecarboxamido)imidazo[1,2-b]pyridazine-8-carboxylic acid (12 mg, 89% yield). The product was used directly in the next step. LCMS (ESI) m/e 247.1 [(M+H)+, calcd for $C_{11}H_{11}N_4O_3$ 247.2].

Part C. 3-(Cyclopropanecarboxamido)-N-(4-isopropoxypyridin-3-yl)imidazo[1,2-b]pyridazine-8-carboxamide

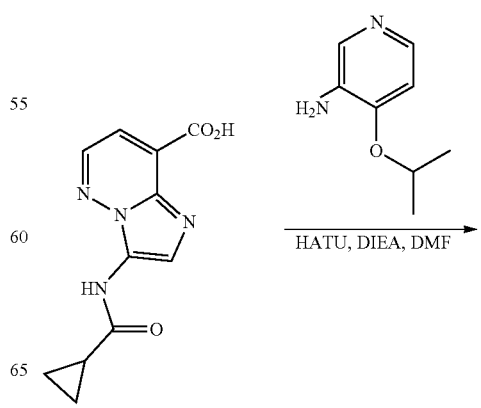

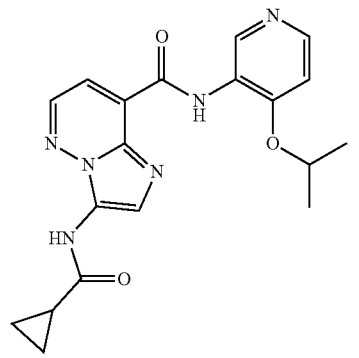

To a solution of 3-(cyclopropanecarboxamido)imidazo[1,2-b]pyridazine-8-carboxylic acid (15 mg, 0.061 mmol), 4-isopropoxypyridin-3-amine (18.54 mg, 0.122 mmol), and N,N-diisopropylethylamine (0.064 mL, 0.366 mmol) in DMF (1 mL) was added HATU (46.3 mg, 0.122 mmol). The reaction mixture was stirred at rt for 2 h. The mixture was concentrated and the residue was purified by reverse phase HPLC (Method A) to afford 3-(cyclopropanecarboxamido)-N-(4-isopropoxypyridin-3-yl)imidazo[1,2-b]pyridazine-8-carboxamide, 2 TFA (7 mg, 10.93 µmol, 18% yield) as a red oil: $^1$H NMR (500 MHz, METHANOL-$d_4$) 9.84 (s, 1H), 8.75 (d, J=4.6 Hz, 1H), 8.56 (dd, J=6.8, 1.0 Hz, 1H), 8.07 (s, 1H), 7.92 (d, J=4.6 Hz, 1H), 7.75 (d, J=6.7 Hz, 1H), 5.27 (dt, J=12.2, 6.0 Hz, 1H), 2.13-2.07 (m, 1H), 1.56 (d, J=3.8 Hz, 6H), 1.14-1.04 (m, 2H), 1.03-0.95 (m, 2H); LCMS (ESI) m/e 379.3 [(M−H)$^−$, calcd for $C_{19}H_{19}N_6O_3$ 379.2]; HPLC (Method A): $t_R$=8.95 min; (Method B) $t_R$=9.20 min.

Example 47

3-(Cyclobutanecarboxamido)-N-(4-isopropoxypyridin-3-yl)imidazo[1,2-b]pyridazine-8-carboxamide

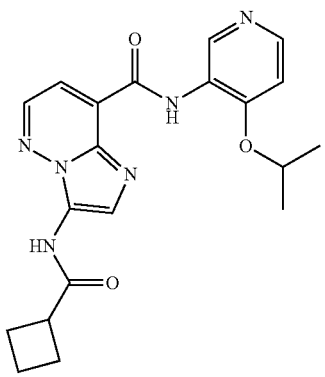 [SMILES: CC(C)Oc1ccncc1NC(=O)c1ccnn2c(NC(=O)C3CCC3)cnc12]

Part A. 3-Aminoimidazo[1,2-b]pyridazine-8-carboxylic acid

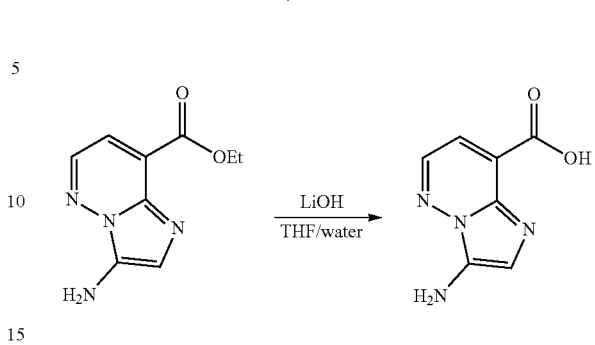

A mixture of ethyl 3-aminoimidazo[1,2-b]pyridazine-8-carboxylate (150 mg, 0.727 mmol) and LiOH (52.3 mg, 2.182 mmol) in tetrahydrofuran (2 mL) and water (0.100 mL) was stirred at rt for 2 h. The reaction mixture was concentrated to afford 3-aminoimidazo[1,2-b]pyridazine-8-carboxylic acid (150 mg, 0.842 mmol, 116% yield) as an off-white solid. The crude product was used directly in the next step. $^1$H NMR (400 MHz, DMSO-$d_6$) 8.50 (d, J=4.5 Hz, 1H), 7.31 (d, J=4.5 Hz, 1H), 6.98 (s, 1H), 5.49 (s, 2H); LCMS (ESI) m/e 179.1 [(M+H)$^+$, calcd for $C_7H_7N_4O_2$ 179.1].

Part B. 3-Amino-N-(4-isopropoxypyridin-3-yl)imidazo[1,2-b]pyridazine-8-carboxamide A mixture of 3-aminoimidazo[1,2-b]pyridazine-8-carboxylic acid (150 mg, 0.842 mmol), 4-isopropoxypyridin-3-amine (384 mg, 2.53 mmol), N,N-diisopropylethylamine (0.735 mL, 4.21 mmol) and HATU (640 mg, 1.684 mmol) in DMF (5 mL) was stirred at room temperature for 4 h. The reaction mixture was transferred to a separatory funnel containing saturated aqueous NaHCO$_3$ solution (10 mL). The aqueous layer was extracted with methylene chloride (3×10 mL). The combined organic layers were washed with brine (10 mL), dried over MgSO$_4$, filtered, and concentrated. The residue was purified by reverse phase HPLC (Method A) to afford 3-amino-N-(4-isopropoxypyridin-3-yl)imidazo[1,2-b]pyridazine-8-carboxamide, 3 TFA (150 mg, 0.229 mmol, 27% yield) as a red solid: $^1$H NMR (400 MHz, DMSO-d$_6$) 12.85 (s, 1H), 9.71 (d, J=1.0 Hz, 1H), 8.71 (d, J=4.5 Hz, 1H), 8.69 (dd, J=6.8, 1.0 Hz, 1H), 7.83 (d, J=6.8 Hz, 1H), 7.60 (d, J=4.5 Hz, 1H), 7.23 (s, 1H), 5.26 (dt, J=12.1, 6.1 Hz, 1H), 1.56 (d, J=6.0 Hz, 6H); LCMS (ESI) m/e 313.2 [(M+H)$^+$, calcd for C$_{15}$H$_{17}$N$_6$O$_2$ 313.1].

Part C. 3-(Cyclobutanecarboxamido)-N-(4-isopropoxypyridin-3-yl)imidazo[1,2-b]pyridazine-8-carboxamide

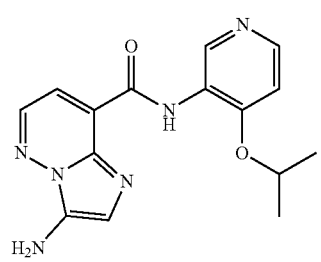
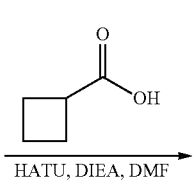
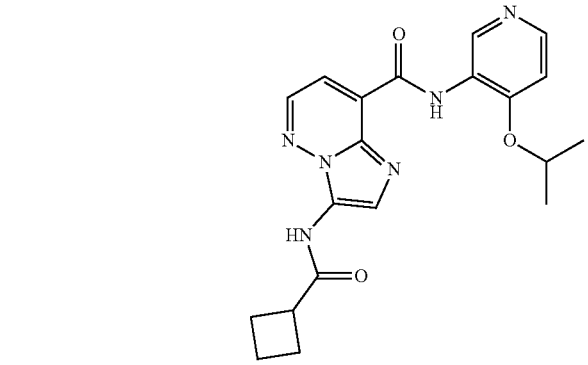

To a solution of 3-amino-N-(4-isopropoxypyridin-3-yl)imidazo[1,2-b]pyridazine-8-carboxamide, 3 TFA (60 mg, 0.092 mmol), cyclobutanecarboxylic acid (0.018 mL, 0.183 mmol), and N,N-diisopropylethylamine (0.096 mL, 0.550 mmol) in DMF (1 mL) a rt, was added HATU (69.7 mg, 0.183 mmol). The reaction mixture was stirred at rt for 4 h. The mixture was concentrated and the residue was purified by reverse phase HPLC (Method A) to afford 3-(cyclobutanecarboxamido)-N-(4-isopropoxypyridin-3-yl)imidazo[1,2-b]pyridazine-8-carboxamide, 2 TFA (10 mg, 0.015 mmol, 17% yield) as a red solid: $^1$H NMR (400 MHz, DMSO-d$_6$) 12.76 (s, 1H), 10.68 (s, 1H), 9.71 (s, 1H), 8.88 (d, J=4.5 Hz, 1H), 8.67 (d, J=6.3 Hz, 1H), 8.12 (s, 1H), 7.91 (d, J=4.5 Hz, 1H), 7.80 (d, J=6.8 Hz, 1H), 5.25 (quin, J=6.0 Hz, 1H), 2.36-2.11 (m, 5H), 2.07-1.94 (m, 1H), 1.92-1.79 (m, 1H), 1.57 (d, J=6.0 Hz, 6H); LCMS (ESI) m/e 395.3 [(M+H)$^+$, calcd for C$_{20}$H$_{23}$N$_6$O$_3$ 395.2]; HPLC (Method A): t$_R$=8.80 min; (Method B) t$_R$=8.34 min.

Preparation of the Amine Intermediates

The following amine intermediates used in the above Examples were prepared as described by Lou et al., in WO 2015/069594.

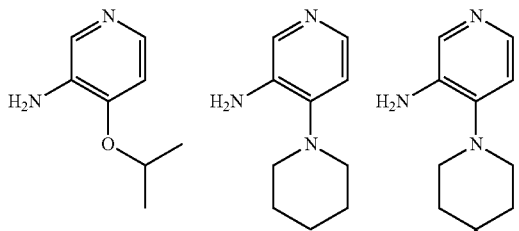
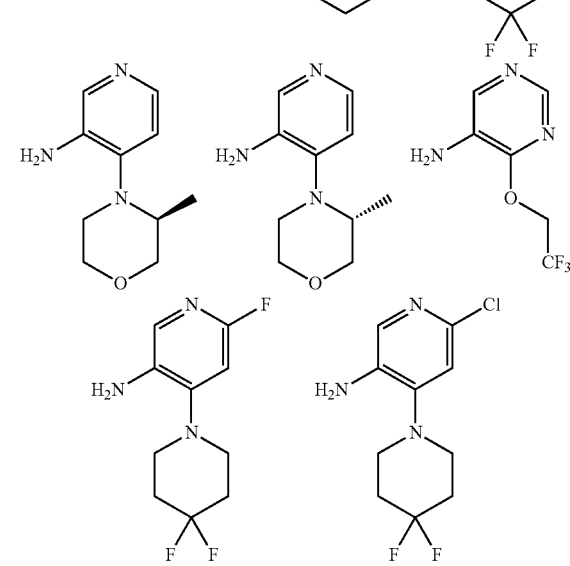

Additional amine intermediates used for the preparation of the above Examples were prepared as described below:

Preparation of 4-(2,2,2-trifluoroethoxy)pyridin-3-amine

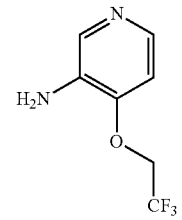 [SMILES: Nc1cnccc1OCC(F)(F)F]

Part A. 3-Nitro-4-(2,2,2-trifluoroethoxy)pyridine

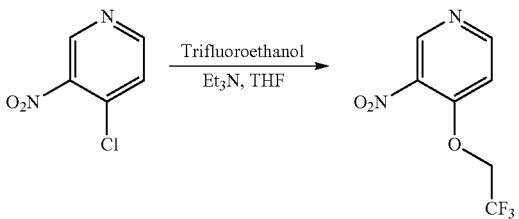 [SMILES: O=[N+]([O-])c1cnccc1Cl ; O=[N+]([O-])c1cnccc1OCC(F)(F)F]

A mixture of 4-chloro-3-nitropyridine (1.00 g, 6.31 mmol), 2,2,2-trifluoroethanol (3.15 g, 31.5 mmol) and triethylamine (2.64 mL, 18.92 mmol) in THF (10 mL) was stirred at reflux for 12 h. The reaction mixture was transferred to a separatory funnel containing water (25 mL). The aqueous layer was extracted with ethyl acetate (3×20 mL). The combined organic layers were washed with brine (15 mL), dried over MgSO$_4$, filtered, and concentrated to afford 3-nitro-4-(2,2,2-trifluoroethoxy)pyridine (1.3 g, 5.85 mmol, 93% yield) as a tan solid: $^1$H NMR (400 MHz, DMSO-d$_6$) δ 9.09 (s, 1H), 8.79 (d, J=6.0 Hz, 1H), 7.58 (d, J=6.0 Hz, 1H), 5.16 (q, J=8.7 Hz, 2H); LCMS (ESI) m/e 223.0 [(M+H)$^+$, calcd for C$_7$H$_6$N$_2$O$_3$F$_3$ 223.0].

Part B. 4-(2,2,2-Trifluoroethoxy)pyridin-3-amine

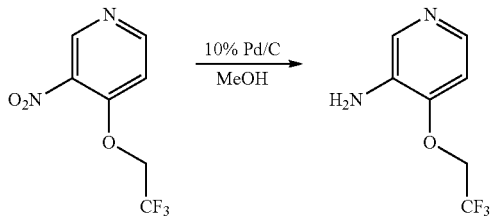 [SMILES: "MeOH" ; O=[N+]([O-])c1cnccc1OCC(F)(F)F ; Nc1cnccc1OCC(F)(F)F]

A mixture of 3-nitro-4-(2,2,2-trifluoroethoxy)pyridine (1.3 g, 5.85 mmol) and 10% palladium on carbon (0.623 g, 0.293 mmol) in methanol (20 mL) was stirred under H$_2$ at 1 atm for 2 h. The catalyst was removed by filtration through a pad of Celite. The mixture was concentrated to afford 4-(2,2,2-trifluoroethoxy)pyridin-3-amine (1.0 g, 5.20 mmol, 89% yield) as a red oil: $^1$H NMR (400 MHz, DMSO-d$_6$) δ 7.96 (s, 1H), 7.76 (d, J=5.5 Hz, 1H), 6.96 (d, J=5.3 Hz, 1H), 4.93 (s, 2H), 4.84 (q, J=8.9 Hz, 2H); LCMS (ESI) m/e 193.1 [(M+H)$^+$, calcd for C$_7$H$_5$N$_2$OF$_3$ 193.1].

Preparation of 4-phenylpyridin-3-amine

Part A. 3-Nitro-4-phenylpyridine

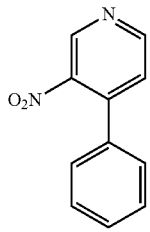

A mixture of 4-chloro-3-nitropyridine (500 mg, 3.15 mmol), phenylboronic acid (577 mg, 4.73 mmol) and Na$_2$CO$_3$ (2M) (3.94 mL, 7.88 mmol) in toluene (10 mL) and ethanol (2.00 mL) was degassed. Bis(triphenylphosphine)palladium(II) chloride (111 mg, 0.158 mmol) was added and the reaction mixture was heated to 100° C. for 4 h. The reaction mixture was transferred to a separatory funnel containing saturated aqueous NaHCO$_3$ solution (20 mL). The aqueous layer was extracted with ethyl acetate (3×20 mL). The combined organic layers were washed with brine (25 mL), dried over MgSO$_4$, filtered, and concentrated. The residue was purified by column chromatography on silica gel (30%→50% ethyl acetate in hexanes; 40 g column) to afford 3-nitro-4-phenylpyridine (600 mg, 3.00 mmol, 95% yield) as a tan solid: $^1$H NMR (400 MHz, DMSO-d$_6$) 9.19 (s, 1H), 8.92 (d, J=5.0 Hz, 1H), 7.69 (dd, J=5.0, 0.5 Hz, 1H), 7.58-7.51 (m, 3H), 7.48-7.41 (m, 2H); LCMS (APCI) m/e 201.1 [(M+H)$^+$, calcd for C$_{11}$H$_9$N$_2$O$_2$ 201.1].

Part B. 4-Phenylpyridin-3-amine

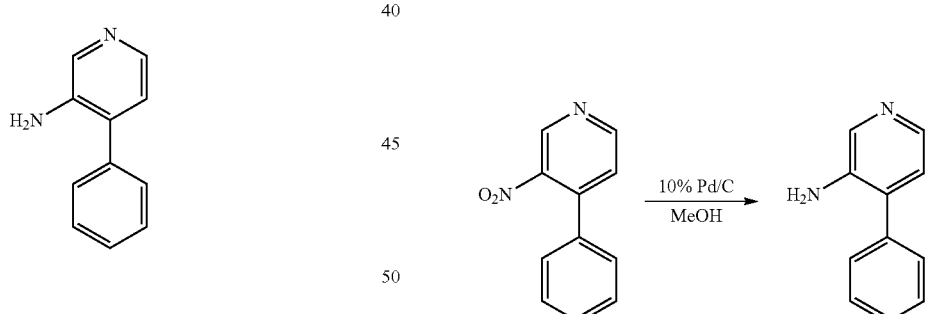

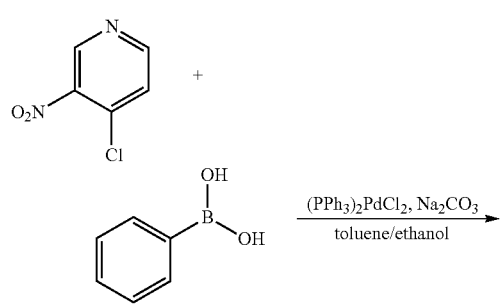

A mixture of 3-nitro-4-phenylpyridine (600 mg, 3.00 mmol) and 10% palladium on carbon (319 mg, 0.150 mmol) in methanol (20 mL) was stirred under H$_2$ at 1 atm for 3 h. The catalyst was removed by filtration through a pad of Celite. The mixture was concentrated to afford 4-phenylpyridin-3-amine (420 mg, 2.468 mmol, 82% yield) as an off-white solid: $^1$H NMR (400 MHz, DMSO-d$_6$) δ 8.11 (s, 1H), 7.85 (d, J=4.8 Hz, 1H), 7.54-7.47 (m, 4H), 7.45-7.38 (m, 1H), 7.00 (d, J=4.5 Hz, 1H), 5.10 (br. s., 2H); LCMS (ESI) m/e 171.1 [(M+H)$^+$, calcd for C$_{11}$H$_{11}$N$_2$ 171.1].

Preparation of 4-(4-fluorophenyl)pyridin-3-amine

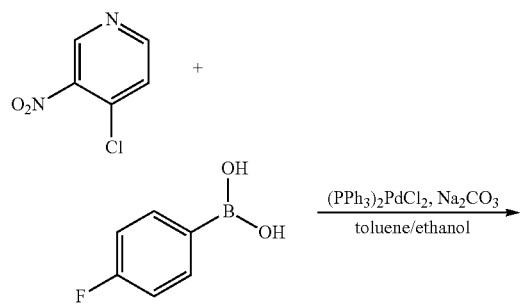

Part A. 4-(4-Fluorophenyl)-3-nitropyridine

A mixture of 4-chloro-3-nitropyridine (1.00 g, 6.31 mmol), (4-fluorophenyl)boronic acid (1.32 g, 9.46 mmol) and Na$_2$CO$_3$ (2M) (7.88 mL, 15.77 mmol) in toluene (20 mL) and ethanol (4.00 mL) was degassed. Bis(triphenylphosphine)palladium(II) chloride (0.221 g, 0.315 mmol) was added and the reaction mixture was heated to 100° C. for 4 h. The reaction mixture was transferred to a separatory funnel containing saturated aqueous NaHCO$_3$ solution (20 mL). The aqueous layer was extracted with ethyl acetate (3×20 mL). The combined organic layers were washed with brine (25 mL), dried over MgSO$_4$, filtered, and concentrated. The residue was purified by column chromatography on silica gel (30%→50% ethyl acetate in hexanes; 40 g column) to afford 4-(4-fluorophenyl)-3-nitropyridine (1.1 g, 5.04 mmol, 80% yield) as a colorless solid: $^1$H NMR (400 MHz, DMSO-d$_6$) δ 9.21 (s, 1H), 8.92 (d, J=5.3 Hz, 1H), 7.74-7.64 (m, 1H), 7.58-7.48 (m, 2H), 7.45-7.32 (m, 2H); LCMS (ESI) m/e 219.0 [(M+H)$^+$, calcd for C$_{11}$H$_5$N$_2$O$_2$F 219.1].

Part B. 4-(4-Fluorophenyl)pyridin-3-amine

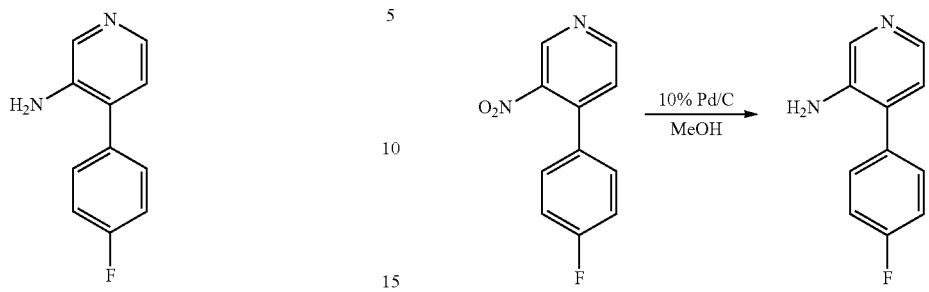

A mixture of 4-(4-fluorophenyl)-3-nitropyridine (1.1 g, 5.04 mmol) and 10% palladium on carbon (0.537 g, 0.252 mmol) in methanol (30 mL) was stirred under H$_2$ at 1 atm for 3 h. The catalyst was removed by filtration through a pad of Celite. The mixture was concentrated to afford 4-(4-fluorophenyl)pyridin-3-amine (865 mg, 4.60 mmol, 91% yield) as a colorless solid: $^1$H NMR (400 MHz, DMSO-d$_6$) δ 8.11 (s, 1H), 7.84 (d, J=5.0 Hz, 1H), 7.63-7.46 (m, 2H), 7.39-7.23 (m, 2H), 6.98 (d, J=4.8 Hz, 1H), 5.12 (s, 2H); LCMS (APCI) m/e 189.1 [(M+H)$^+$, calcd for C$_{11}$H$_{11}$N$_2$F 189.1].

Preparation of 4-(3-aminopyridin-4-yl)benzonitrile

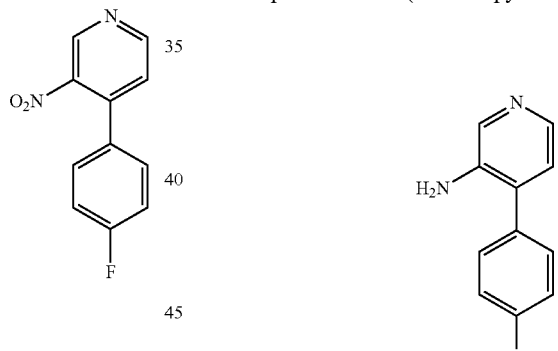

Part A. 4-(3-Nitropyridin-4-yl)benzonitrile

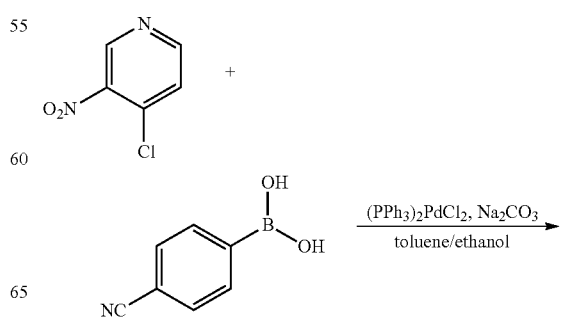

-continued

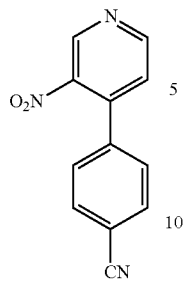

A mixture of 4-chloro-3-nitropyridine (600 mg, 3.78 mmol), 4-cyanophenylboronic acid (834 mg, 5.68 mmol), and Na$_2$CO$_3$ (2M) (4.73 mL, 9.46 mmol) in toluene (20 mL) and ethanol (4.00 mL) was degassed. Bis(triphenylphosphine)palladium(II) chloride (133 mg, 0.189 mmol) was added and the reaction mixture was heated to 100° C. for 4 h. The reaction mixture was transferred to a separatory funnel containing saturated aqueous NaHCO$_3$ solution (20 mL). The aqueous layer was extracted with ethyl acetate (3×20 mL). The combined organic layers were washed with brine (25 mL), dried over MgSO$_4$, filtered, and concentrated. The residue was purified by column chromatography on silica gel (30%→50% ethyl acetate in hexanes; 40 g column) to afford 4-(3-nitropyridin-4-yl)benzonitrile (450 mg, 1.998 mmol, 53% yield) as a tan solid: $^1$H NMR (400 MHz, DMSO-d$_6$) δ 9.30 (s, 1H), 8.98 (d, J=5.0 Hz, 1H), 8.21-7.92 (m, 2H), 7.85-7.52 (m, 3H); LCMS (ESI) m/e 226.0 [(M+H)$^+$, calcd for C$_{12}$H$_8$N$_3$O$_2$ 226.1].

Part B. 4-(3-Aminopyridin-4-yl)benzonitrile

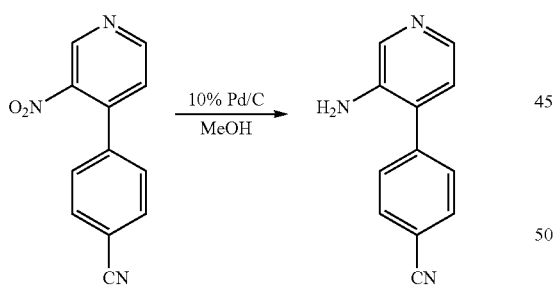

A mixture of 4-(3-nitropyridin-4-yl)benzonitrile (450 mg, 1.998 mmol) and 10% palladium on carbon (425 mg, 0.200 mmol) in methanol (15 mL) was stirred under H$_2$ at 1 atm for 3 h. The catalyst was removed by filtration through a pad of Celite. The mixture was concentrated and the residue was purified by column chromatography on silica gel (30%→70% ethyl acetate in hexanes; 25 g column) to afford 4-(3-aminopyridin-4-yl)benzonitrile (210 mg, 1.076 mmol, 54% yield) as a tan solid: $^1$H NMR (400 MHz, DMSO-d$_6$) δ 8.14 (s, 1H), 7.99-7.93 (m, 2H), 7.86 (d, J=5.0 Hz, 1H), 7.73-7.66 (m, 2H), 5.30 (s, 2H); LCMS (ESI) m/e 196.1 [(M+H)$^+$, calcd for C$_{12}$H$_{10}$N$_3$ 196.1].

Preparation of 1-(3-aminopyridin-4-yl)piperidine-4-carbonitrile

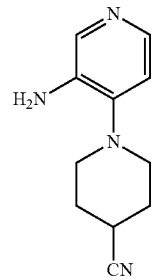 [SMILES: N#CC1CCN(c2ccncc2N)CC1]

Part A.
1-(3-Nitropyridin-4-yl)piperidine-4-carbonitrile

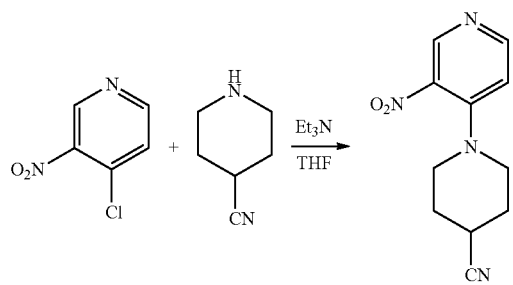

A mixture of 4-chloro-3-nitropyridine (2.00 g, 12.61 mmol), piperidine-4-carbonitrile (2.78 g, 25.2 mmol) and triethylamine (5.27 mL, 37.8 mmol) in THF (20 mL) was stirred at room temperature for 2 h. The solvent was evaporated and suspended in hexanes. The solid was filtered and dried to afford 1-(3-nitropyridin-4-yl)piperidine-4-carbonitrile (2.50 g, 10.76 mmol, 85% yield) as a yellow solid: $^1$H NMR (400 MHz, DMSO-d$_6$) δ 8.80 (s, 1H), 8.39 (d, J=6.0 Hz, 1H), 7.23 (d, J=6.3 Hz, 1H), 3.35-3.28 (m, 2H), 3.23-3.13 (m, 3H), 2.00 (ddt, J=13.2, 6.6, 3.5 Hz, 2H), 1.89-1.76 (m, 2H).

Part B.
1-(3-Aminopyridin-4-yl)piperidine-4-carbonitrile

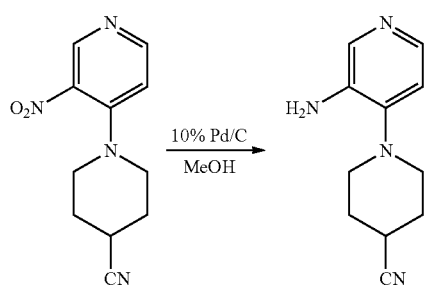

A mixture of 1-(3-nitropyridin-4-yl)piperidine-4-carbonitrile (2.50 g, 10.76 mmol) and 10% palladium on carbon (1.146 g, 10.76 mmol) in methanol (50 mL) was stirred under H$_2$ at 1 atm for 2 h. The catalyst was removed by filtration through a pad of Celite. The mixture was concentrated to afford 1-(3-aminopyridin-4-yl)piperidine-4-carbonitrile (2.1 g, 10.38 mmol, 96% yield) as a tan solid: $^1$H NMR (400 MHz, DMSO-d$_6$) δ 7.93 (s, 1H), 7.74 (d, J=5.3 Hz, 1H), 6.78 (d, J=5.3 Hz, 1H), 4.82 (s, 2H), 3.18 (d, J=4.5 Hz, 1H), 3.04 (d, J=4.3 Hz, 3H), 2.78 (br. s., 2H), 2.11-1.99 (m, 2H), 1.97-1.86 (m, 2H); LCMS (ESI) m/e 203.2 [(M+H)$^+$, calcd for C$_{11}$H$_{15}$N$_4$ 203.2].

Preparation of 4-(4-fluoropiperidin-1-yl)pyridin-3-amine

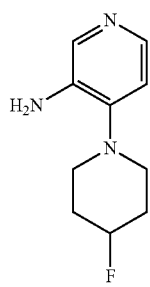

Part A. 4-(4-Fluoropiperidin-1-yl)-3-nitropyridine

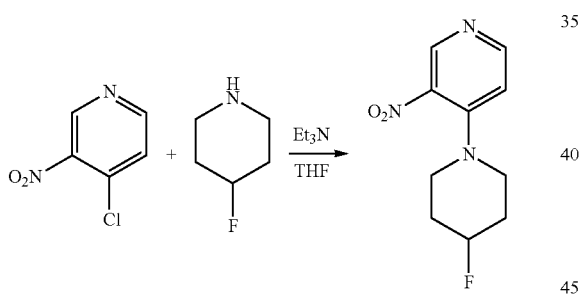

A mixture of 4-chloro-3-nitropyridine (1 g, 6.31 mmol), 4-fluoropiperidine (0.781 g, 7.57 mmol) and triethylamine (2.64 mL, 18.92 mmol) in THF (30 mL) was stirred at room temperature for 2 h. The reaction mixture was transferred to a separatory funnel containing saturated aqueous NaHCO$_3$ solution (20 mL). The aqueous layer was extracted with ethyl acetate (3×25 mL). The combined organic layers were washed with brine (20 mL), dried over MgSO$_4$, filtered, and concentrated. The residue was purified by column chromatography on silica gel (20%→50% ethyl acetate in hexanes; 40 g column) to afford 4-(4-fluoropiperidin-1-yl)-3-nitropyridine (750 mg, 3.33 mmol, 53% yield) as a yellow solid: $^1$H NMR (400 MHz, CHLOROFORM-d) δ 8.85-8.76 (m, 1H), 8.33 (d, J=6.0 Hz, 1H), 6.86 (d, J=5.8 Hz, 1H), 5.13-4.71 (m, 1H), 3.43-3.31 (m, 2H), 3.16 (dt, J=12.9, 4.7 Hz, 2H), 2.11-1.92 (m, 4H); LCMS (ESI) m/e 226.1 [(M+H)$^+$, calcd for C$_{10}$H$_{13}$N$_3$O$_2$F 226.1].

Part B. 4-(4-Fluoropiperidin-1-yl)pyridin-3-amine

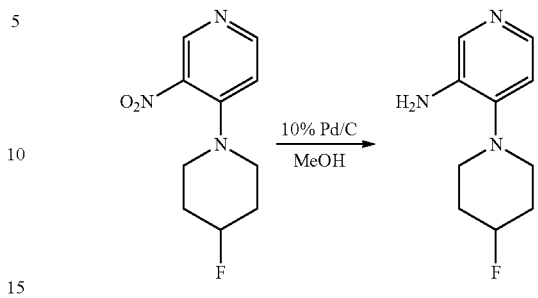

A mixture of 4-(4-fluoropiperidin-1-yl)-3-nitropyridine (750 mg, 3.33 mmol) and 10% palladium on carbon (354 mg, 0.167 mmol) in methanol (20 mL) was stirred under H$_2$ at 1 atm for 2 h. The catalyst was removed by filtration through a pad of Celite. The mixture was concentrated to afford 4-(4-fluoropiperidin-1-yl)pyridin-3-amine (600 mg, 3.07 mmol, 92% yield) as a tan solid: $^1$H NMR (400 MHz, DMSO-d$_6$) δ 7.93 (s, 1H), 7.80 (d, J=5.5 Hz, 1H), 6.89 (d, J=5.5 Hz, 1H), 5.01 (br. s., 2H), 4.96-4.74 (m, 1H), 3.09 (t, J=9.5 Hz, 2H), 2.91 (ddd, J=11.6, 7.2, 3.8 Hz, 2H), 2.13-1.97 (m, 2H), 1.91 (dddd, J=13.5, 10.3, 7.1, 3.5 Hz, 2H); LCMS (ESI) m/e 196.2 [(M+H)$^+$, calcd for C$_{10}$H$_{15}$N$_3$F 196.1].

Preparation of 4-morpholinopyridin-3-amine

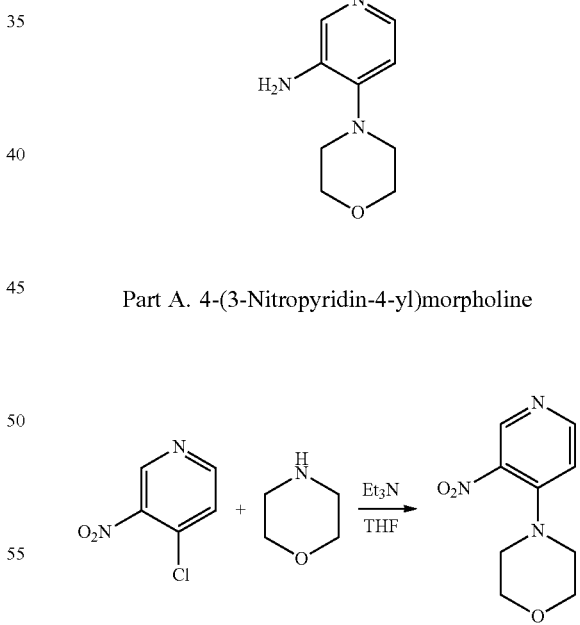

Part A. 4-(3-Nitropyridin-4-yl)morpholine

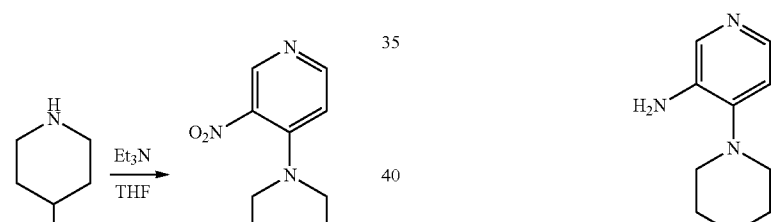

A mixture of 4-chloro-3-nitropyridine (5.00 g, 31.5 mmol), morpholine (5.50 mL, 63.1 mmol) and triethylamine (13.19 mL, 95 mmol) in THF (50 mL) was stirred at room temperature for 2 h. The mixture was concentrated and the residue was suspended in hexanes. The solid was collected by filtration and was dried to afford 4-(3-nitropyridin-4-yl)morpholine (6.00 g, 28.7 mmol, 91% yield) as a yellow solid: $^1$H NMR (400 MHz, DMSO-d$_6$) δ 8.79 (s, 1H), 8.41

(d, J=6.0 Hz, 1H), 7.22 (d, J=6.0 Hz, 1H), 3.74-3.65 (m, 4H), 3.27-3.18 (m, 4H); LCMS (ESI) m/e 210.1 [(M+H)$^+$, calcd for C$_9$H$_{12}$N$_3$O$_3$ 210.1].

Part B. 4-Morpholinopyridin-3-amine

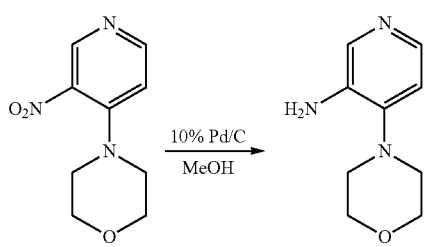

A mixture of 4-(3-nitropyridin-4-yl)morpholine (6.00 g, 28.7 mmol) and 10% palladium on carbon (1.526 g, 1.434 mmol) in MeOH (50 mL) was stirred under H$_2$ at 1 atm for 3 h. The catalyst was removed by filtration through a pad of Celite. The mixture was concentrated and the residue was purified by column chromatography on silica gel (10% methanol in methylene chloride; 160 g column) to afford 4-morpholinopyridin-3-amine (4.30 g, 23.99 mmol, 84% yield) as an off-white solid: $^1$H NMR (400 MHz, DMSO-d$_6$) δ 7.94 (s, 1H), 7.76 (d, J=5.3 Hz, 1H), 6.78 (d, J=5.3 Hz, 1H), 4.84 (s, 2H), 3.82-3.70 (m, 4H), 2.94-2.85 (m, 4H); LCMS (ESI) m/e 180.1 [(M+H)$^+$, calcd for C$_9$H$_{14}$N$_3$O 180.1].

Preparation of 4-(2-methylmorpholino)pyridin-3-amine

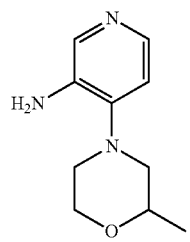

Part A. 2-Methyl-4-(3-nitropyridin-4-yl)morpholine

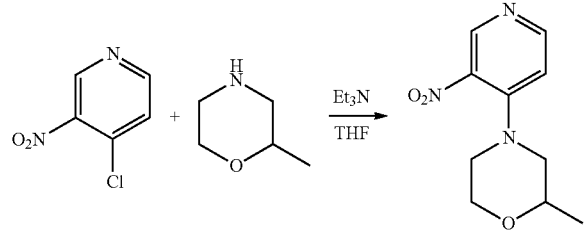

A mixture of 4-chloro-3-nitropyridine (2.00 g, 12.61 mmol), 2-methylmorpholine (1.718 mL, 15.14 mmol), and triethylamine (5.27 mL, 37.8 mmol) in THF (30 mL) was stirred at room temperature for 2 h. The solvent was evaporated and the residue was purified by column chromatography on silica gel (30-40% ethyl acetate in hexanes, 40 g column) to afford 2-methyl-4-(3-nitropyridin-4-yl)morpholine (2.00 g, 8.96 mmol, 71% yield) as a yellow solid: $^1$H NMR (400 MHz, DMSO-d$_6$) δ 8.79 (s, 1H), 8.39 (d, J=6.0 Hz, 1H), 7.23 (d, J=6.3 Hz, 1H), 3.91-3.82 (m, 1H), 3.70-3.52 (m, 2H), 3.41-3.32 (m, 1H), 3.25 (dd, J=12.9, 1.9 Hz, 1H), 3.16-3.05 (m, 1H), 2.81 (dd, J=12.9, 10.2 Hz, 1H), 1.12 (d, J=6.3 Hz, 3H); LCMS (ESI) m/e 224.2 [(M+H)$^+$, calcd for C$_{10}$H$_{14}$N$_3$O$_3$ 224.2].

Part B. 4-(2-Methylmorpholino)pyridin-3-amine

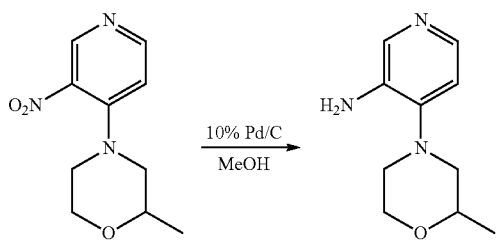 [SMILES: "MeOH" ; CC1CN(c2ccncc2[N+](=O)[O-])CCO1 ; "10% Pd/C" ; CC1CN(c2ccncc2N)CCO1]

A mixture of 2-methyl-4-(3-nitropyridin-4-yl)morpholine (2.0 g, 8.96 mmol) and 10% palladium on carbon (0.953 g, 0.448 mmol) in methanol (20 mL) was stirred under H$_2$ at 1 atm for 2 h. The catalyst was removed by filtration through a pad of Celite. The mixture was concentrated to afford 4-(2-methylmorpholino)pyridin-3-amine (740 mg, 3.83 mmol, 43% yield) as a tan solid: $^1$H NMR (400 MHz, DMSO-d$_6$) δ 7.93 (s, 1H), 7.75 (d, J=5.3 Hz, 1H), 6.77 (d, J=5.3 Hz, 1H), 4.82 (s, 2H), 3.91-3.81 (m, 1H), 3.81-3.51 (m, 2H), 3.24-2.98 (m, 2H), 2.58 (td, J=11.5, 3.0 Hz, 1H), 2.29 (t, J=10.8 Hz, 1H), 1.11 (d, J=6.3 Hz, 3H); LCMS (ESI) m/e 194.1 [(M+H)$^+$, calcd for C$_{10}$H$_{16}$N$_3$O 194.1].

Preparation of 4-ethoxypyridin-3-amine

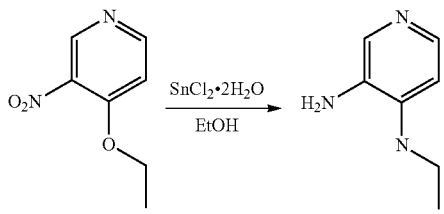

A mixture of 4-ethoxy-3-nitropyridine, HCl (1 g, 4.89 mmol) and tin(II) chloride dihydrate (2.78 g, 14.66 mmol) in ethanol (20 mL) was heated at reflux for 3 h. Saturated aqueous NaHCO$_3$ solution (30 mL) was added and the mixture was filtered through a pad of Celite. The filtrate was concentrated to afford 4-ethoxypyridin-3-amine, 2 HCl (320 mg, 1.516 mmol, 31% yield) as a tan solid: $^1$H NMR (400 MHz, DMSO-d$_6$) δ 8.52-8.40 (m, 1H), 8.17 (s, 1H), 7.95 (d, J=5.5 Hz, 1H), 7.84 (s, 1H), 6.87 (d, J=5.5 Hz, 1H), 4.10 (q, J=7.0 Hz, 2H), 1.37-1.32 (m, 3H); LCMS (ESI) m/e 139.1 [(M+H)$^+$, calcd for C$_7$H$_{11}$N$_2$O 139.2].

Preparation of 4-ethoxypyrimidin-5-amine

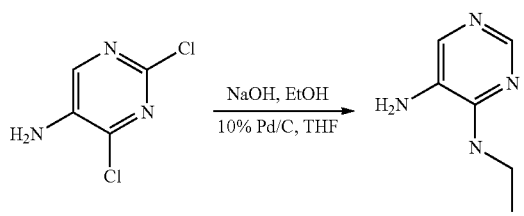

A mixture of 2,4-dichloropyrimidin-5-amine (400 mg, 2.439 mmol), ethanol (12.200 g, 265 mmol), NaOH (195 mg, 4.88 mmol) and 10% palladium on carbon (260 mg, 0.122 mmol) in THF (4 mL) was stirred under a hydrogen atmosphere at room temperature for 24 h. The mixture was concentrated and the residue was purified by column chromatography on silica gel (40%→70% ethyl acetate in hexanes; 25 g column) to afford 4-ethoxypyrimidin-5-amine (140 mg, 1.006 mmol, 41% yield) as a yellow solid: $^1$H NMR (400 MHz, DMSO-$d_6$) δ 8.03 (s, 1H), 7.85 (s, 1H), 5.07 (s, 2H), 4.39 (q, J=7.0 Hz, 2H), 1.35 (t, J=7.0 Hz, 3H); LCMS (ESI) m/e 140.1 [(M+H)+, calcd for $C_6H_{10}N_3O$ 140.1].

Preparation of
6-fluoro-4-(2-methylmorpholino)pyridin-3-amine

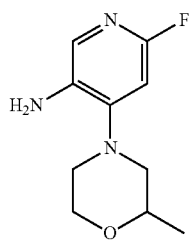

Part A. 2,4-Difluoro-5-nitropyridine

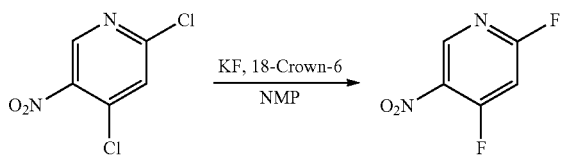

A mixture of 2,4-dichloro-5-nitropyridine (450 mg, 2.332 mmol), potassium fluoride (406 mg, 7.00 mmol), and 18-Crown-6 (99 mg, 0.373 mmol) in NMP (2 mL) was heated at 100° C. under nitrogen for 2 h. The reaction mixture was transferred to a separatory funnel containing water (5 mL) and ether (50 mL). The layers were separated and the organic layer was washed with water (2×5 mL), brine (5 mL), dried over MgSO$_4$, filtered, and concentrated. The residue was purified by column chromatography on silica gel (10%→20% ethyl acetate in hexanes; 40 g column) to afford 2,4-difluoro-5-nitropyridine (177 mg, 1.106 mmol, 47% yield) as a colorless solid: $^1$H NMR (400 MHz, CDCl$_3$)

δ 9.07 (d, J=9.5 Hz, 1H), 6.95 (dd, J=9.4, 2.4 Hz, 1H); $^{19}$F NMR (376 MHz, CDCl$_3$) δ -52.17 (d, J=27.7 Hz, 1F), -98.12 (dt, J=29.5, 8.7 Hz, 1F).

Part B. 4-(2-Fluoro-5-nitropyridin-4-yl)-2-methylmorpholine

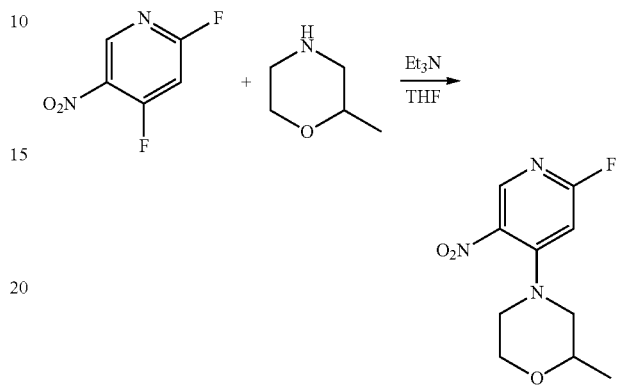

To a solution of 2,4-difluoro-5-nitropyridine (335 mg, 2.093 mmol) in THF (10 mL) at -40° C., was added via cannula 2-methylmorpholine (80 mg, 0.791 mmol) dissolved in THF (1 mL) followed by Et$_3$N (0.583 mL, 4.19 mmol). The cloudy yellow mixture was stirred at -40° C. for 1 h and was allowed to warm to 0° C. After stirring an additional 2 h, TLC (50% ethyl acetate in hexanes) showed a more polar spot with a small amount of starting material remaining. The mixture was concentrated. The product was purified by column chromatography on silica gel (20%→50% ethyl acetate in hexanes; 25 g column) to afford 4-(2-fluoro-5-nitropyridin-4-yl)-2-methylmorpholine (264 mg, 1.094 mmol, 52% yield) as a yellow oil: $^1$H NMR (400 MHz, CDCl$_3$) δ 8.63 (s, 1H), 6.42 (s, 1H), 4.04-3.95 (m, 1H), 3.89-3.76 (m, 2H), 3.26-3.17 (m, 3H), 2.87 (dd, J=12.8, 10.0 Hz, 1H), 1.24 (d, J=6.3 Hz, 3H); $^{19}$F NMR (376 MHz, CDCl$_3$) δ -61.49 (s, 1F); LC/MS (ESI) m/e 242.1 [(M+H)$^+$, calcd for $C_{10}H_{13}FN_3O_3$ 242.1].

Part C.
6-Fluoro-4-(2-methylmorpholino)pyridin-3-amine

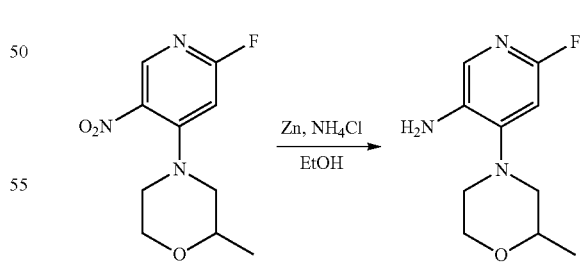

To a solution of 4-(2-fluoro-5-nitropyridin-4-yl)-2-methylmorpholine (244 mg, 1.012 mmol) in ethanol (8 mL) was added ammonium chloride (433 mg, 8.09 mmol) and zinc (powder) (661 mg, 10.12 mmol). The reaction mixture was heated at 50° C. for 2 h. The mixture was filtered through a pad of Celite and was concentrated. The reaction mixture was transferred to a separatory funnel containing saturated aqueous NaHCO$_3$ solution (15 mL). The aqueous layer was extracted with dichloromethane (3×20 mL). The combined organic layers were washed with brine (15 mL), dried over MgSO₄, filtered, and concentrated to give 6-fluoro-4-(2-methylmorpholino)pyridin-3-amine (224 mg, 93% yield): $^1$H NMR (400 MHz, CDCl$_3$) δ 7.61 (s, 1H), 6.43 (d, J=0.8 Hz, 1H), 4.05-3.98 (m, 1H), 3.88-3.74 (m, 2H), 3.58 (br. s., 2H), 3.35-3.21 (m, 2H), 2.79 (td, J=11.6, 3.1 Hz, 1H), 2.46 (dd, J=11.8, 10.0 Hz, 1H), 1.25 (d, J=6.3 Hz, 3H); LC/MS (ESI) m/e 212.2 [(M+H)⁺, calcd for C₁₀H₁₅FN₃O 212.1].

Preparation of 7-(3-nitropyridin-4-yl)-2-oxa-7-azaspiro[3.5]nonane

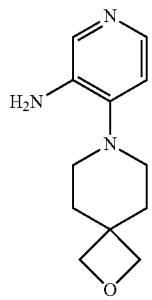 [SMILES: Nc1cnccc1N1CCC2(CC1)COC2]

Part A. 7-(3-Nitropyridin-4-yl)-2-oxa-7-azaspiro [3.5]nonane

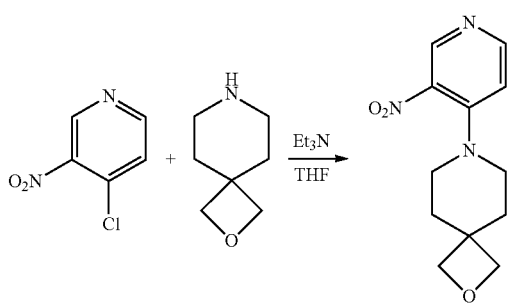

Triethylamine (0.330 mL, 2.365 mmol) was added to a mixture of 4-chloro-3-nitropyridine (125 mg, 0.788 mmol) and 2-oxa-7-azaspiro[3.5]nonane (100 mg, 0.788 mmol) in THF (1.5 mL) and the mixture was stirred at room temperature for 2.5 h. The reaction mixture was then heated at 50° C. for 30 min. No further reaction took place. The mixture was cooled to room temperature and was concentrated. The residue was purified by column chromatography on silica gel (2%→7% methanol in CH₂Cl₂; 12 g column) to afford 7-(3-nitropyridin-4-yl)-2-oxa-7-azaspiro[3.5]nonane (153 mg, 0.614 mmol, 78% yield) as a yellow oil: $^1$H NMR (400 MHz, CHLOROFORM-d) δ 8.86 (s, 1H), 8.38 (d, J=6.0 Hz, 1H), 6.88 (d, J=6.0 Hz, 1H), 4.52 (s, 4H), 3.21-3.12 (m, 4H), 2.09-2.02 (m, 4H); LC/MS (ESI) m/e 250.1 [(M+H)⁺, calcd for C₁₂H₁₆N₃O₃ 250.1].

Part B. 7-(3-Nitropyridin-4-yl)-2-oxa-7-azaspiro [3.5]nonane

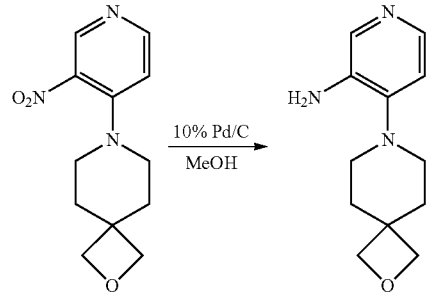

A mixture of 7-(3-nitropyridin-4-yl)-2-oxa-7-azaspiro [3.5]nonane (150 mg, 0.602 mmol) and 10% palladium on carbon (128 mg, 0.060 mmol) in MeOH (3 mL) was stirred under a hydrogen balloon for 2.5 h. The mixture was filtered through a pad of Celite and was concentrated. The residue was purified by column chromatography on silica gel (4%→8% methanol in CH₂Cl₂; 25 g column) to afford 4-(2-oxa-7-azaspiro[3.5]nonan-7-yl)pyridin-3-amine (93 mg, 0.424 mmol, 71% yield) as a colorless oil: $^1$H NMR (400 MHz, CHLOROFORM-d) δ 8.05 (s, 1H), 7.99 (d, J=5.0 Hz, 1H), 6.77 (d, J=5.3 Hz, 1H), 4.51 (s, 4H), 2.89 (br. s., 4H), 2.04 (t, J=5.0 Hz, 4H); LC/MS (ESI) m/e 220.2 [(M+H)+, calcd for C₁₂H₁₈N₃O 220.1].

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of formula I

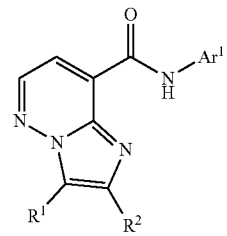

where:
R¹ is hydrogen or N(R³)(R⁴);
R² is hydrogen, alkyl, cycloalkyl, or cycloalkenyl;
or R² is pyridinyl or phenyl and is substituted with 0-3 substituents selected from cyano, halo, alkyl, haloalkyl, alkoxy, and haloalkoxy;
R³ is hydrogen, alkyl, (cycloalkyl)alkyl, cycloalkyl, alkylcarbonyl, or cycloalkylcarbonyl;
R⁴ is hydrogen;
Ar¹ is 3-pyridinyl, 3-pyridazinyl, 4-pyridazinyl, 5-pyrimidinyl, or 2-pyrazinyl, and is substituted with 0-3 substituents selected from halo, alkyl, haloalkyl, alkoxy, haloalkoxy, alkylsulfonyl, $N(R^3)(R^4)$, or $Ar^2$; and $Ar^2$ is phenyl substituted with 0-3 substituents selected from cyano, halo, alkyl, haloalkyl, alkoxy, haloalkoxy;

or a pharmaceutically acceptable salt thereof.

2. A compound of claim 1 where $R^1$ is $N(R^3)(R^4)$ and $R^2$ is hydrogen.

3. A compound of claim 1 where $R^1$ is hydrogen and $R^2$ is not hydrogen.

4. A compound of claim 1 where $Ar^1$ is 3-pyridinyl substituted with 0-3 substituents selected from the group consisting of halo, alkyl, haloalkyl, alkoxy, and haloalkoxy.

5. A compound of claim 1 where $Ar^1$ is 5-pyrimidinyl substituted with 0-3 substituents selected from the group consisting of halo, alkyl, haloalkyl, alkoxy, and haloalkoxy.

6. A compound of claim 1 where $Ar^2$ is phenyl substituted with 0-3 substituents selected from the group consisting of cyano, halo, alkyl, haloalkyl, alkoxy, and haloalkoxy.

7. A pharmaceutical composition comprising a compound of claim 1 or a pharmaceutically acceptable salt thereof and a pharmaceutically acceptable carrier.

* * * * *